United States Patent
Gharib et al.

(10) Patent No.: US 11,877,860 B2
(45) Date of Patent: *Jan. 23, 2024

(54) SYSTEMS AND METHODS FOR PERFORMING NEUROPHYSIOLOGIC MONITORING DURING SPINE SURGERY

(71) Applicant: NuVasive, Inc., San Diego, CA (US)

(72) Inventors: James E. Gharib, San Diego, CA (US); Eric Finley, San Diego, CA (US); Adam Azzara, San Diego, CA (US); Dmitry Novikov, San Diego, CA (US); William Taylor, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,318

(22) Filed: Nov. 6, 2014

(65) Prior Publication Data
US 2015/0230749 A1    Aug. 20, 2015

Related U.S. Application Data

(63) Continuation-in-part of application No. 14/073,772, filed on Nov. 6, 2013, now Pat. No. 11,259,737.
(Continued)

(51) Int. Cl.
*A61B 5/00* (2006.01)
*A61B 17/02* (2006.01)
(Continued)

(52) U.S. Cl.
CPC ............ *A61B 5/4566* (2013.01); *A61B 5/316* (2021.01); *A61B 5/389* (2021.01); *A61B 5/4836* (2013.01);
(Continued)

(58) Field of Classification Search
CPC ..... A61B 5/0488; A61B 5/0492; A61B 5/407; A61B 5/4082; A61B 5/4566;
(Continued)

(56) References Cited

U.S. PATENT DOCUMENTS

| 208,227 A | 9/1878 | Dorr |
| 972,983 A | 10/1910 | Arthur |

(Continued)

FOREIGN PATENT DOCUMENTS

| CN | 101930947 | 12/2010 |
| CN | 101939049 | 1/2011 |

(Continued)

OTHER PUBLICATIONS

Courtine, G., et al., "Modulation of multisegmental monosynaptic responses in a variety of leg muscles during walking and running in humans", The Journal of Physiology, Apr. 2007, vol. 582, Edition 3, pp. 1125-1139.*

(Continued)

*Primary Examiner* — Devin B Henson
*Assistant Examiner* — H. Q. Nguyen

(57) ABSTRACT

The present invention relates to a system and related methods for performing neurophysiologic assessments during surgical procedures. A method includes the steps of delivering a first transcutaneous, trans-abdominal stimulation signal to a spinal nerve root superior to a surgical target site; and determining a first neuromuscular response data set, based on transmission of said first transcutaneous, trans-abdominal stimulation signal, of a muscle located inferior to said surgical target site.

20 Claims, 37 Drawing Sheets

Related U.S. Application Data

(60) Provisional application No. 61/722,923, filed on Nov. 6, 2012.

(51) Int. Cl.
  *A61B 5/316* (2021.01)
  *A61B 5/389* (2021.01)
  *A61B 17/00* (2006.01)

(52) U.S. Cl.
  CPC .......... *A61B 5/4893* (2013.01); *A61B 5/7246* (2013.01); *A61B 17/025* (2013.01); *A61B 17/0206* (2013.01); *A61B 17/0218* (2013.01); *A61B 5/743* (2013.01); *A61B 2017/00039* (2013.01); *A61B 2017/00115* (2013.01); *A61B 2017/00199* (2013.01); *A61B 2017/00929* (2013.01); *A61B 2017/0256* (2013.01); *A61B 2017/0262* (2013.01); *A61B 2505/05* (2013.01); *A61B 2560/0468* (2013.01)

(58) Field of Classification Search
  CPC .......... A61B 5/6823; A61B 2560/0468; A61B 2017/0256; A61B 2017/0262; A61B 5/4893
  See application file for complete search history.

(56) References Cited

U.S. PATENT DOCUMENTS

| | | |
|---|---|---|
| 1,328,624 A | 1/1920 | Graham |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Coyler |
| 3,785,368 A | 1/1974 | McCarthy et al. |
| 3,830,226 A | 8/1974 | Staub |
| 3,851,641 A | 12/1974 | Toole et al. |
| 3,957,036 A | 5/1976 | Norman |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,252,130 A | 2/1981 | Le Pivert |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,627,441 A | 12/1986 | Martin |
| 4,633,889 A | 1/1987 | Talalla et al. |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,196,015 A | 3/1993 | Neubardt |
| 5,220,920 A | 6/1993 | Gharib |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutson et al. |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,389,069 A | 2/1995 | Weaver |
| 5,450,845 A | 9/1995 | Axelgaard |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,579,781 A | 12/1996 | Cooke |
| 5,593,429 A | 1/1997 | Ruff |
| 5,599,279 A | 2/1997 | Slotman |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer |
| 5,741,253 A | 4/1998 | Michelson |
| 5,758,643 A | 6/1998 | Wong et al. |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron et al. |
| 5,797,854 A | 8/1998 | Hedgecock |
| 5,806,522 A | 9/1998 | Katims |
| 5,807,272 A | 9/1998 | Kun et al. |
| 5,814,073 A | 9/1998 | Bonutti |
| 5,830,150 A | 11/1998 | Palmer et al. |
| 5,830,151 A | 11/1998 | Hadzic et al. |
| 5,851,191 A | 12/1998 | Gozani et al. |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,928,159 A | 7/1999 | Eggers et al. |
| 5,935,131 A | 8/1999 | Bonutti |
| 5,938,688 A | 8/1999 | Schiff |
| 5,947,964 A | 9/1999 | Eggers et al. |
| 5,976,094 A | 11/1999 | Gozani |
| 6,004,262 A | 12/1999 | Putz et al. |
| 6,011,985 A | 1/2000 | Athan |
| 6,026,323 A | 2/2000 | Skladnev et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,128,576 A | 10/2000 | Nishimoto |
| 6,132,386 A | 10/2000 | Gozani et al. |
| 6,132,387 A | 10/2000 | Gozani et al. |

(56) References Cited

U.S. PATENT DOCUMENTS

| | | |
|---|---|---|
| 6,135,965 A | 10/2000 | Turner et al. |
| 6,139,493 A | 10/2000 | Koros et al. |
| 6,146,335 A | 11/2000 | Gozani |
| 6,161,047 A | 12/2000 | King et al. |
| 6,181,961 B1 | 1/2001 | Prass |
| 6,206,826 B1 | 3/2001 | Mathews et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,337,994 B1 | 1/2002 | Stoianovici et al. |
| 6,393,325 B1 | 5/2002 | Mann et al. |
| 6,407,335 B1 | 6/2002 | Franklin-Lees et al. |
| 6,416,480 B1 | 7/2002 | Nenov |
| 6,425,859 B1 | 7/2002 | Foley et al. |
| 6,425,901 B1 | 7/2002 | Zhu et al. |
| 6,451,015 B1 | 9/2002 | Rittman et al. |
| 6,466,817 B1 * | 10/2002 | Kaula ............... A61B 5/04001 600/546 |
| 6,500,128 B2 | 12/2002 | Marino |
| 6,535,759 B1 | 3/2003 | Epstein et al. |
| 6,564,078 B1 | 5/2003 | Marino et al. |
| 6,579,244 B2 | 6/2003 | Goodwin |
| 6,593,528 B2 | 7/2003 | Franklin-Lees et al. |
| 6,719,692 B2 | 4/2004 | Kleffner et al. |
| 6,760,616 B2 | 7/2004 | Hoey et al. |
| 6,796,985 B2 | 9/2004 | Bolger et al. |
| 6,819,956 B2 | 11/2004 | DiLorenzo |
| 6,829,508 B2 | 12/2004 | Schulman et al. |
| 6,830,051 B1 | 12/2004 | Lesniak et al. |
| 6,849,047 B2 | 2/2005 | Goodwin |
| 6,855,105 B2 | 2/2005 | Jackson, III |
| 6,895,280 B2 | 5/2005 | Meadows et al. |
| 6,902,569 B2 | 6/2005 | Parmer et al. |
| 6,926,728 B2 | 8/2005 | Zucherman et al. |
| 6,929,606 B2 | 8/2005 | Ritland |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| D533,875 S | 12/2006 | Miles et al. |
| 7,177,677 B2 | 2/2007 | Kaula et al. |
| 7,207,949 B2 | 4/2007 | Miles et al. |
| 7,216,001 B2 | 5/2007 | Hacker et al. |
| 7,255,680 B1 | 8/2007 | Gharib |
| 7,470,236 B1 | 12/2008 | Kelleher et al. |
| 7,522,953 B2 | 4/2009 | Kaula et al. |
| 7,582,058 B1 | 9/2009 | Miles et al. |
| 7,657,308 B2 | 2/2010 | Miles et al. |
| 7,664,544 B2 | 2/2010 | Miles et al. |
| 7,691,057 B2 | 4/2010 | Miles et al. |
| 7,706,843 B2 | 4/2010 | Kaplan |
| 7,819,801 B2 | 10/2010 | Miles et al. |
| 7,857,813 B2 | 12/2010 | Schmitz et al. |
| 7,878,981 B2 | 2/2011 | Strother et al. |
| 7,887,538 B2 | 2/2011 | Bleich et al. |
| 7,896,815 B2 | 3/2011 | Thrope et al. |
| 7,905,840 B2 | 3/2011 | Pimenta et al. |
| 7,938,830 B2 | 5/2011 | Saadat et al. |
| 7,963,927 B2 | 6/2011 | Kelleher et al. |
| 8,068,912 B2 | 11/2011 | Kaula et al. |
| 11,259,737 B2 | 3/2022 | Taylor |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0123780 A1 | 9/2002 | Grill et al. |
| 2002/0134570 A1 | 9/2002 | Franklin-Lees et al. |
| 2002/0161415 A1 | 10/2002 | Cohen et al. |
| 2002/0193843 A1 | 12/2002 | Hill |
| 2003/0032966 A1 | 2/2003 | Foley et al. |
| 2003/0105503 A1 | 6/2003 | Marino |
| 2004/0199084 A1 | 10/2004 | Kelleher et al. |
| 2004/0203490 A1 | 10/2004 | Kaplan |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0149035 A1 | 7/2005 | Pimenta et al. |
| 2005/0159785 A1 | 7/2005 | Rueter |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0166157 A1 | 7/2006 | Rahman et al. |
| 2006/0224078 A1 | 10/2006 | Hoey et al. |
| 2007/0016097 A1 | 1/2007 | Farquhar et al. |
| 2007/0021682 A1 | 1/2007 | Gharib et al. |
| 2007/0100212 A1 * | 5/2007 | Pimenta ............... A61B 5/742 600/210 |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0167574 A1 | 7/2008 | Farquhar et al. |
| 2008/0208287 A1 * | 8/2008 | Palermo ............... A61N 1/20 607/3 |
| 2008/0221473 A1 | 9/2008 | Calancie et al. |
| 2009/0018399 A1 | 1/2009 | Martinelli |
| 2009/0018610 A1 | 1/2009 | Gharib et al. |
| 2009/0054804 A1 * | 2/2009 | Gharib ............... A61B 5/04001 600/554 |
| 2009/0105604 A1 | 4/2009 | Bertagnoli et al. |
| 2009/0124860 A1 | 5/2009 | Miles et al. |
| 2009/0177112 A1 * | 7/2009 | Gharib ............... A61B 5/0488 600/554 |
| 2009/0192403 A1 | 7/2009 | Gharib et al. |
| 2009/0204016 A1 | 8/2009 | Gharib et al. |
| 2009/0204176 A1 | 8/2009 | Miles et al. |
| 2009/0209879 A1 | 8/2009 | Kaula et al. |
| 2009/0259108 A1 | 10/2009 | Miles et al. |
| 2010/0010367 A1 | 1/2010 | Foley et al. |
| 2010/0036384 A1 | 2/2010 | Gorek et al. |
| 2010/0069783 A1 | 3/2010 | Miles et al. |
| 2010/0076335 A1 | 3/2010 | Gharib et al. |
| 2010/0094093 A1 | 4/2010 | Miles et al. |
| 2010/0105986 A1 | 4/2010 | Miles et al. |
| 2010/0105987 A1 | 4/2010 | Miles et al. |
| 2010/0113884 A1 | 5/2010 | Miles et al. |
| 2010/0130827 A1 | 5/2010 | Pimenta et al. |
| 2010/0137690 A1 | 6/2010 | Miles et al. |
| 2010/0152603 A1 | 6/2010 | Miles et al. |
| 2010/0152604 A1 | 6/2010 | Kaula et al. |
| 2010/0160738 A1 | 6/2010 | Miles et al. |
| 2010/0174146 A1 | 7/2010 | Miles et al. |
| 2010/0174147 A1 | 7/2010 | Miles et al. |
| 2010/0174148 A1 | 7/2010 | Miles et al. |
| 2010/0249644 A1 | 9/2010 | Miles et al. |
| 2010/0273738 A1 | 10/2010 | Valcke et al. |
| 2010/0286554 A1 * | 11/2010 | Davis ............... A61B 5/04001 600/554 |
| 2010/0286784 A1 * | 11/2010 | Curran ............... A61F 2/4425 623/17.16 |
| 2010/0312103 A1 | 12/2010 | Gorek et al. |
| 2011/0098761 A1 | 4/2011 | Wittenberger |
| 2012/0109233 A1 | 5/2012 | Lee |
| 2012/0226186 A1 | 9/2012 | Baars et al. |
| 2012/0259156 A1 * | 10/2012 | Freeman ............... A61B 5/11 600/14 |
| 2013/0076157 A1 * | 3/2013 | Stein ............... A61B 5/1036 307/116 |

(56) References Cited

U.S. PATENT DOCUMENTS

| | | | |
|---|---|---|---|
| 2013/0245490 A1* | 9/2013 | Strother | A61N 1/36017 |
| | | | 600/554 |
| 2014/0316484 A1 | 10/2014 | Edgerton et al. | |
| 2015/0088030 A1* | 3/2015 | Taylor | A61B 5/0488 |
| | | | 600/554 |
| 2022/0142555 A1 | 5/2022 | Taylor | |

FOREIGN PATENT DOCUMENTS

| | | |
|---|---|---|
| JP | 2003-534866 A | 11/2003 |
| JP | 2006512983 A | 4/2006 |
| JP | 2012-505707 | 3/2012 |
| JP | 2012505707 A | 3/2012 |
| JP | 2012526614 A | 11/2012 |
| WO | 2008/124079 A1 | 10/2008 |
| WO | 2008124079 | 10/2008 |
| WO | 2010/044880 A1 | 4/2010 |
| WO | 2010044880 | 4/2010 |
| WO | WO 2013/071309 | 5/2013 |

OTHER PUBLICATIONS

Ladenbauer et al; "Stimulation of the Human Lumbar Spinal Cord with Implanted and Surface Electrodes: A computer Simulation Study," 2010, IEEE Transactions on Neural Systems and Rehabilitation Engineering, vol. 18 Issue: 6, p. 637-645. (Year: 2010).*

"Electromyography System," International Search Report from International Application No. PCT/US00/32329, dated Apr. 27, 2001, 9 pages.

"Nerve Proximity and Status Detection System and Method," International Search Report from International Application No. PCT/US01/18606, dated Oct. 18, 2001, 6 pages.

"Relative Nerve Movement and Status Detection System and Method," International Search Report from International Application No. PCT/US01/18579, dated Jan. 15, 2002, 6 pages.

"System and Method for Determining Nerve Proximity Direction and Pathology During Surgery," International Search Report from International Application No. PCT/US02/22247, dated Mar. 27, 2003, 4 pages.

"System and Methods for Determining Nerve Direction to a Surgical Instrument," International Search Report from International Application No. PCT/US03/02056, dated Aug. 12, 2003, 5 pages.

"Systems and Methods for Performing Percutaneous Pedicle Integrity Assessments," International Search Report from International Application No. PCT/US02/35047, dated Aug. 11, 2003, 5 pages.

"Systems and Methods for Performing Surgery Procedures and Assessments," International Search Report from International Application No. PCT/US02/30617, dated Jun. 5, 2003, 4 pages.

"Systems and Methods for Performing Neurophysiologic Assessments During Spine Surgery," International Search Report from International Application No. PCT/US06/03966, dated Oct. 23, 2006, 5 pages.

"Multi-Channel Stimulation Threshold Detection Algorithm for Use in Neurophysiology Monitoring," International Search Report from International Application No. PCT/US06/37013, dated Mar. 19, 2007, 6 pages.

"Neurophysiologic Monitoring System," International Search Report and the Written Opinion from International Application No. PCT/US08/04427, dated Jul. 28, 2008, 6 pages.

"Systems and Methods for Performing Neurophysiologic Monitoring During Spine Surgery," International Search Report and Written Opinion from International Application No. PCT/US/64449, dated Feb. 4, 2015, 8 pages.

"Neurovision SE Nerve Locator/Monitor," RLN Systems Inc. Operator's Manual, 1999, 22 pages.

Calancie et al., "Stimulus-Evoked EMG Monitoring During Transpedicular Lumbosacral Spine Instrumentation," Spine, 1994, 19(24): 2780-2786.

Holland et al., "Higher Electrical Stimulus Intensities are Required to Activate Chronically Compressed Nerve Roots. Implications for Intraoperative Electromyographic Pedicle Screw Testing," Spine, 1998, 23(2): 224-227.

Ladenbauer et al., "Stimulation of the Human Lumbar Spinal Cord With Implanted and Surface Electrodes: A Computer Simulation Study," (2010) IEEE Transactions 18(6): 637-645.

Minassian et al., "Human lumbar cord circuitries can be activated by extrinsic tonic input to generate locomotor-like activity," (2007) Human Movement Science 26(2): 275-295.

Minassian et al., "Neuromodulation of lower limb motor control in restorative neurology," (2012) Clinical Neurology and Neurosurgery 114:489-497.

Minassian et al., "Posterior Root-Muscle Reflexes Elicited by Transcutaneous Stimulation of the Human Lumbosacral Cord", (2007) Muscle Nerve 35:327-336.

Swash and Snooks, "Slowed motor conduction in lumbosacral nerve roots in cauda equina lesions: a new diagnostic technique,", (1986) J Neurol Neurosurg Psychiatry 49:808-816.

Gonzalez et al., "Intraoperative Neurophysiological Monitoring during Spine Surgery: A Review," Neurosurg Focus. (2009) 27(4):E6.

Bednarik, et al., "The Value of Somatosensory- and Motor-Evoked Potentials in Predicting and Monitoring the Effect of Therapy in Spondylotic Cervical Myelopathy," Spine 1999, 24(15):1593-1598.

Calancie, et al., ""Threshold-level" multipulse transcranial electrical stimulation of motor cortex for intraoperative monitoring of spinal motor tracts: description of method and comparison to somatosensory evoked potential monitoring," J Neurosurg 1998, 88:457-470.

Calancie, et al., "Threshold-level repetitive transcranial electrical stimulation for intraoperative monitoring of central motor conduction," J Neurosurg (Spine 1) 2011, 95:161-168.

Calancie and Molano, "Alarm Criteria for Motor-Evoked Potentials," Spine 2008 33(4):406-414.

Deletis, et al., "Neurophysiological mechanisms underlying motor evoked potentials in anesthetized humans. Part 1. Recovery time of corticospinal tract direct waves elicited by pairs of transcranial electrical stimuli," Clin Neurophysiol 2001, 112:438-444.

Deletis, et al., "Neurophysiological mechanisms underlying motor evoked potentials in anesthetized humans. Part 2. Relationship between epidurally and muscle recorded MEPs in man," Clin Neurophysiol 2001, 112:445-452.

Ginsburg, et al., "Postoperative paraplegia with preserved intraoperative somatosensory evoked potentials," J Neurosurg 1985, 63:296-300.

Gokaslan, et al., "Intraoperative Monitoring of Spinal Cord Function Using Motor Evoked Potentials via Transcutaneous Epidural Electrode During Anterior Cervical Spinal Surgery," J Spinal Disord 1997, 10(4):299-303.

Kombos, et al., "Monitoring of intraoperative motor evoked potentials to increase the safety of surgery in and around the motor cortex," J Neurosurg 2001, 95:608-614.

Langeloo, et al., "A New Application of TCE-MEP: Spinal Cord Monitoring in Patients With Severe Neuromuscular Weakness Undergoing Corrective Spine Surgery," J Spinal Disord 2001, 14(5):445-448.

Langeloo, et al., "Transcranial Electrical Motor-Evoked Potential Monitoring During Surgery for Spinal Deformity," Spine 2003, 28(10) 1043-1050.

MacDonald, "Safety of Intraoperative Transcranial Electrical Stimulation Motor Evoked Potential Monitoring," J Clin Neurophys 2002, 19(5):416-429.

Osburn, et al., "TCeMEPs offer Safe, Reliable Monitoring of Spinal Cord Motor Pathway Function during Cervical Procedures Performed for Post-traumatic Spine Injury," 17th Annual Meeting of the American Society of Neurophysiological Monitoring Abstract Presentations, 2006.

Watanabe, et al., "Transcranial electrical stimulation through screw electrodes for intraoperative monitoring of motor evoked potentials," J Neurosurg 2004, 100:155-160.

(56) References Cited

OTHER PUBLICATIONS

Wiedemayer, et al., "False negative findings in intraoperative SEP monitoring: analysis of 658 neurosurgical cases and review of published reports," J Neurol Neurosurg Psychiatry 2004, 75:280-286.
Balzer, et al., "Simultaneous Somatosensory Evoked Potential and Electromyographic Recordings during Lumbosacral Decompression and Instrumentation Technique Application," Neurosurgery 1998, 42:1318-1325.
Banoczi, "Update on Anesthetic and Metabolic Effects During Intraoperative Neurophysiological Monitoring (IONM)," Am J END Technol 2005, 45:225-239.
Chawla, et al., "Somatosensory Evoked Potentials: Clinical Applications," eMedicine Neurology, 2008, http://emedicine.medscape.com/article/1139393-overview.
Dawson, et al., "Spinal Cord Monitoring. Results of the Scoliosis Research Society and the European Spinal Deformity Society Survey," Spine 1991, 16(8) Supplement: S361-S364.
Deutsch, et al., "Somatosensory evoked potential monitoring in anterior thoracic vertebrectomy," J Neurosurg (Spine2) 2000, 92:155-161.
Devlin and Schwartz, "Intraoperative Neurophysiologic Monitoring During Spinal Surgery," J Am Acad Orthop Surg 2007, 15(9):549-560.
Gunnarsson, et al., "Real-Time Continuous Intraoperative Electromyographic and Somatosensory Evoked Potential Recordings in Spinal Surgery: Correlation of Clinical and Electrophysiologic Findings in a Prospective, Consecutive Series of 213 Cases," Spine 2004, 29(6):677-684.
Jones, et al., "Two cases of quadriparesis following anterior cervical discectomy, with normal perioperative somatosensory evoked potentials," J Neurol Neurosurg Psychiatry 2003, 74:273-276.
Kamel, et al., "The Use of Somatosensory Evoked Potentials to Determine the Relationship Between Patient Positioning and Impending Upper Extremity Nerve Injury During Spine Surgery: A Retrospective analysis," International Anesthesia Research Society 2006, 102:1538-1542.
Kombos, et al., "Impact of Somatosensory Evoked Potential Monitoring on Cervical Surgery," J Clin Neurophys 2003, 20(2): 122-128.
Kraft, et al., "Somatosensory Evoked Potentials: Clinical Uses," Muscle Nerve 1998, 21:252-258.
Legatt and Soliman, "Somatosensory Evoked Potentials: General Principles," eMedicine Neurology, 2006, http://emedicine.medscape.com/article/1139906-overview.
More, et al., "Cortical Evoked Potential Monitoring During Spinal Surgery: Sensitivity, Specificity, Reliability, and Criteria for Alarm," J Spinal Disord 1988, 1(1):75-80.
Nash, et al., "Spinal Cord Monitoring During Operative Treatment of the Spine," Clin Orthop Relat Res 1977, 126:100-105.
Nuwer, et al., "Somatosensory evoked potential spinal cord monitoring reduces neurologic deficits after scoliosis surgery: results of a large multicenter survey," Electroencephalogr Clin Neurophysiol 1995, 96:6-11.
Padberg, et al., "Somatosensory- and Motor-Evoked Potential Monitoring Without a Wake-Up Test During Idiopathic Scoliosis Surgery: An Accepted Standard of Care," Spine 1998, 23(12):1392-1400.
Pelosi, et al., "Combined monitoring or motor and somatosensory evoked potentials in orthopaedic spinal surgery," Clin Neurophysiol 2002, 113:1082-1091.
Sloan and Heyer, "Anesthesia for Intraoperative Neurophysiologic Monitoring of the Spinal Cord," J Clin Neurophys 2002, 19(5):430-443.
Toleikis, "Intraoperative Monitoring Using Somatosensory Evoked Potentials," J Clin Monit Comput 2005, 19:241-258.
Wiedemayer, et al., "The impact of neurophysiological intraoperative monitoring on surgical decisions: a critical analysis of 423 cases," J Neurosurg 2002, 96:255-262.
Zornow and Drummond, "Intraoperative Somatosensory Evoked Responses Recorded During Onset of the Anterior Spinal Artery Syndrome," J Clin Monit 1989, 5:243-245.
Osburn, "A Guide to the Performance of Transcranial Electrical Motor Evoked Potentials. Part 1. Basic Concepts, Recording Parameters, Special Consideration, and Application," Am J END Technol 2006, 46:98-158.
Deletis et al., "Intraoperative neurophysiological monitoring of the spinal cord during spinal cord and spine surgery: A review focus on the corticospinal tracts", Clinical Neurophsiology, Elsevier Science, vol. 119, No. 2, pp. 248-264, Dec. 22, 2007.
Gregoire Courtine et al., Modulation of multisegmental monosynaptic responses in a variety of leg muscles during walking and running in humans, The Journal of Physiology, 2007, vol. 582, Edition 3, pp. 1125-1139.
Chinese 1st Office Action in Application 201480061648, dated Jun. 28, 2018, 5 pgs.
Chinese 2nd Office Action and Search Report in Application 201480061648, dated Mar. 27, 2019, 8 pgs.
Chinese 3rd Office Action in Application 201480061648, dated Aug. 16, 2019, 9 pgs.
Chinese 4th Office Action in Application 201480061648, dated Feb. 3, 2020, 7 pgs.
Chinese 5th Office Action in Application 201480061648, dated Feb. 1, 2021, 6 pgs.
Chinese 6th Office Action and Search Report in Application 201480061648, dated Jul. 19, 2021, 8 pgs.
European Communication pursuant to Article 94(3) EPC in Application 14859965.7, dated Jun. 19, 2017, 3 pgs.
European Communication pursuant to Article 94(3) EPC in Application 14859965.7, dated Jul. 2, 2020, 5 pgs.
European Extended Search Report in Application 14859965.7, dated May 29, 2017, 4 pgs.
Japanese Decision of Refusal and Dismissal of Amendment in application 2016552487, dated Mar. 3, 2020, 3 pgs.
Japanese Decision of Refusal in Application 2020-115395, dated Mar. 22, 2022, 3 pgs.
Japanese Notice of Reasons for Refusal in application 2016552487, dated Jun. 25, 2019, 3 pgs.
Japanese Notice of Refusal and Search Report in application 2016552487, dated Oct. 30, 2018, 18 pgs.
Japanese Notice of Refusal and Search Report in Application 2020-115395, dated Aug. 17, 2021, 14 pgs.
PCT International Preliminary Report on Patentability in Application PCT/US2014/064449, dated May 19, 2016, 6 pages.
Australian 1st Exam Report in Application 2014346688, dated Jul. 26, 2018, 3 pages.
Australian 1st Exam Report in Application 2019250269, dated Aug. 12, 2020, 4 pages.
Australian 1st Exam Report in Application 2021203764, dated Jul. 20, 2022, 3 pages.
Japanese Refusal in Application 2020115395, dated Mar. 22, 2022, 3 pages.
Japanese Refusal in Application 2020115395, dated Aug. 17, 2021, 3 pages.
Japanese Search Report in Application 2020115395, dated Jul. 21, 2021, 11 pages.
European Summons to attend oral proceedings in Application 14859965.7, dated Apr. 26, 2023, 7 pgs.

* cited by examiner

Single Pulse Stimulation Signal

Multipulse Stimulation Signal

Legend
# = Actual Recruit
# = Inferred Recruit
# = Actual Nonrecruit
# = Inferred Nonrecruit

SYSTEMS AND METHODS FOR PERFORMING NEUROPHYSIOLOGIC MONITORING DURING SPINE SURGERY

CROSS-REFERENCES TO RELATED APPLICATIONS

This U.S. patent application is a continuation-in-part of commonly owned and copending U.S. patent application Ser. No. 14/073,772 entitled "Systems and Methods for Performing Neurophysiologic Monitoring During Spine Surgery", and filed on Nov. 6, 2013 which claims the benefit of priority under 35 U.S.C. 119(e) from U.S. Provisional Application Ser. No. 61/722,923 filed Nov. 6, 2012, the complete disclosures of which are hereby incorporated by reference into this application as if set forth fully herein.

FIELD

The present invention relates to a system and methods generally aimed at surgery. More particularly, the present invention is directed at a system and related methods for performing neurophysiologic assessments during surgical procedures.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease or trauma, such as ruptured or slipped discs, degenerative disc disease, fractured vertebrae, and the like. Patients that suffer from such conditions usually experience extreme and debilitating pain as well as diminished nerve function.

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques are gaining favor due to the fact that they involve accessing the surgical target site via incisions of substantially smaller size with greatly reduced tissue displacement requirements. This, in turn, reduces the pain, morbidity, and cost associated with such procedures. One such minimally invasive approach, a lateral trans-psoas approach to the spine, developed by NuVasive®, Inc., San Diego, CA (XLIF®) has demonstrated great success in reducing patient morbidity, shortening the duration of hospitalization, and speeding recovery time if it is employed.

To create the lateral access corridor to the lumbar spine, the patient is positioned on his or her spine and a surgical access system is advanced through an incision, into the retroperitoneal space, and then through the psoas muscle until the target spinal site (for example, a disc space between a pair of adjacent vertebral bodies) is reached. The surgical access system may include a sequential dilation assembly of increasing diameter and a tissue retraction assembly. The sequential dilation assembly is advanced to the surgical target site and the retractor assembly is then advanced to the target site over the sequential dilation system. Stimulating electrodes may be provided on the distal tip of one or more different components of the surgical access system. Neurophysiologic monitoring may be performed while advancing one or more components of the dilation and retraction assemblies to the target site to detect the presence of, and thereby avoid, nerves lying in the trans-psoas path to the target site.

Once the retractor assembly has been docked at a target site however, a nerve may become compromised due to a variety of factors including, but not limited to, compression of the nerve due to inadvertent contact with the retractor blade and patient positioning on the surgical table. Stimulating within the surgical site provides information regarding the health and status of nearby nerves within the surgical site during maintenance of the lateral access corridor. However, the portion of a nerve that is compressed or otherwise affected may not lie within the surgical site such that information regarding the health and status of a greater portion of the motor neural pathway is desirable. Other methods of stimulating the motor neural pathway (e.g., transcranial electric motor evoked potential monitoring (MEP)) use multi-pulse trains of stimuli with high stimulus intensities and depolarize all nerves along the corticospinal pathway and result in muscle activity of many muscles of the head, upper extremities, torso, and lower extremities. This whole-body stimulation can sometimes lead to large amounts of patient movement during the procedure. It is generally preferable to conduct neurophysiologic monitoring with the least amount of stimulation intensity (and patient movement) as possible. MEP monitoring is also disadvantageous for monitoring the lower motor neural pathway in that requires the use of total intravenous anesthesia (TIVA). TIVA requires close monitoring and is also more expensive than other anesthetic regimens. Furthermore, information regarding each specific nerve root is also desirable because it provides specific information regarding the health and/or status of each nerve root comprising the lumbar plexus. Therefore, a need exists for systems and methods of performing neurophysiologic monitoring on a greater portion of the motor neural pathway, lower amounts of stimulation intensity, shorter pulses, well-received anesthetic requirements, greater specificity of the at-risk nerve roots and earlier indications of potential post-operative complications such that mitigating actions may be taken.

SUMMARY OF THE INVENTION

The present invention includes systems and methods to evaluate the health and status of the lower motor neural pathway before, during and after the establishment of an operative corridor through (or near) any of a variety of tissues having such neural structures which, if contacted or impinged, may otherwise result in neural impairment for the patient. It is expressly noted that, although described herein largely in terms of use in lateral lumbar spinal surgery, the system and methods of the present disclosure are suitable for use in any number of additional spinal surgeries including posterior, posterolateral, anterior, anterolateral lumbar spinal surgeries as well as thoracic and thoracolumbar spinal surgeries. Indeed, the invention of the present disclosure is suitable for use in any number of additional surgical procedures wherein tissue having significant neural structures must be passed through (or near) in order to establish an operative corridor.

According to another broad aspect, the present invention includes a control unit, a patient module, and a plurality of surgical accessories adapted to couple to the patient module. The control unit includes a power supply and is programmed to receive user commands, activate stimulation in a plurality of predetermined modes, process signal data according to defined algorithms, display received parameters and processed data, and monitor system status. The patient module is in communication with the control unit. The patient module is within the sterile field. The patient module includes signal conditioning circuitry, stimulator drive circuitry, and signal conditioning circuitry required to perform said stimulation in said predetermined modes. The patient module includes a processor programmed to perform a plurality of predetermined functions including at least two of neuromuscular pathway assessment, non-evoked monitoring, static pedicle integrity testing, dynamic pedicle integrity testing, nerve proximity detection, manual motor evoked potential monitoring, automatic motor evoked potential monitoring, transcutaneous nerve root testing, manual somatosensory evoked potential monitoring, automatic somatosensory evoked potential monitoring, and surgical correction planning and assessment.

According to still another broad aspect, the present invention includes a processing unit programmed to perform a plurality of predetermined functions using said instrument including at least two of neuromuscular pathway assessment, static pedicle integrity testing, dynamic pedicle integrity testing, nerve proximity detection, transcutaneous nerve root testing, non-evoked monitoring, motor evoked potential monitoring, somatosensory evoked potential monitoring, and surgical correction planning and assessment. The processing system has a pre-established profile for at least one of said predetermined functions so as to facilitate the initiation of said at least one predetermined function.

According to another broad aspect of the present disclosure, there is provided a method for performing transcutaneous, trans-abdominal stimulation of the lumbar motor neural pathways superior and inferior to a surgical target site.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination. It is also expressly noted that, although described herein largely in terms of use in lateral surgery in the lumbar spine, the system and methods of the present disclosure may also be employed in any number of other spine surgery procedures including posterior, poster-lateral, anterior, and anterolateral lumbar, thoracic, and/or cervical spine procedures, all without departing from the present disclosure. The systems and methods described herein boast a variety of inventive features and components that warrant patent protection, both individually and in combination.

Figure 1:
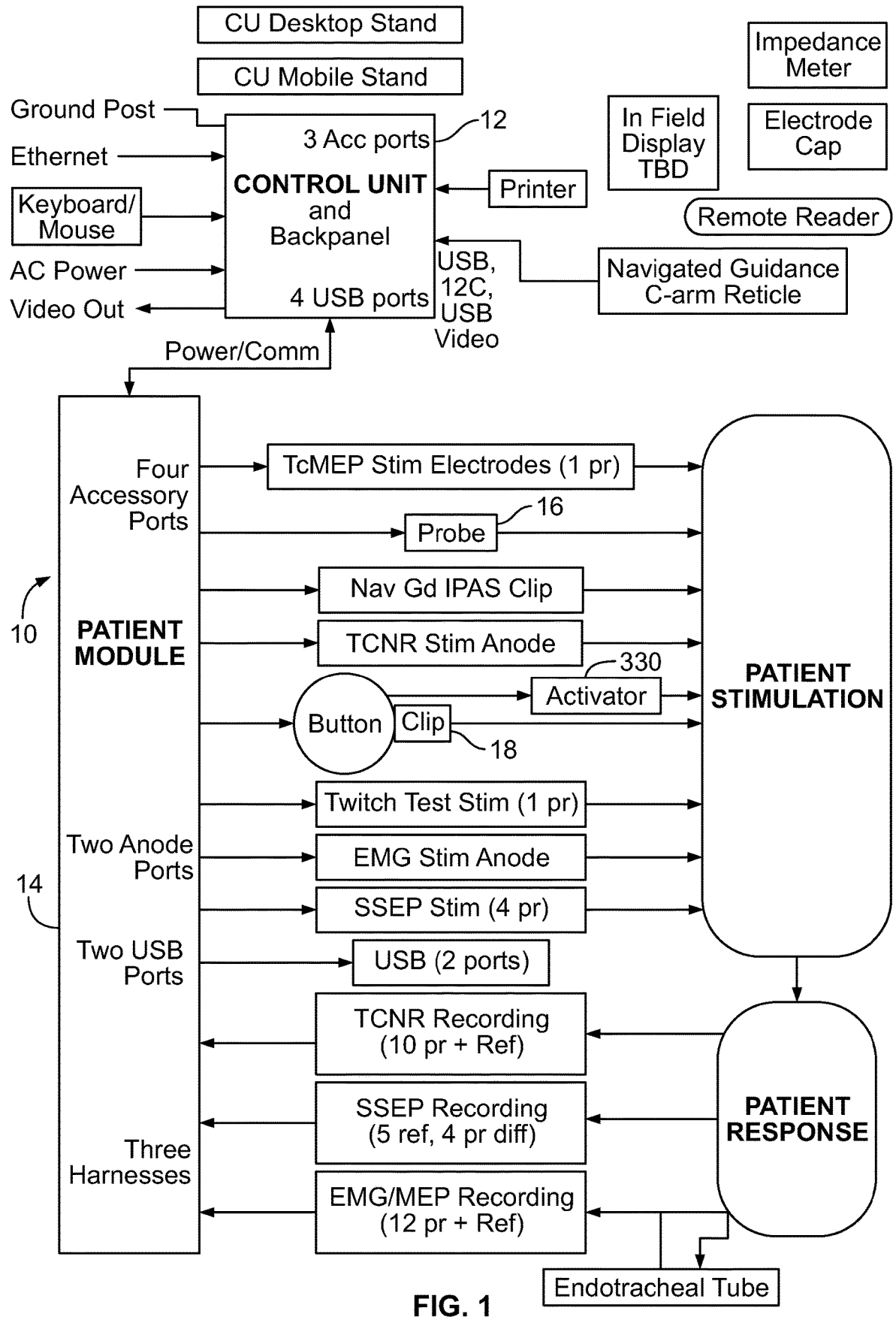
FIG. 1 is a block diagram of an example neurophysiologic monitoring system capable of conducting multiple nerve and spinal cord monitoring functions including but not necessarily limited to neuromuscular pathway, bone integrity, nerve detection, nerve pathology (evoked or free-run EMG), lower motor pathway, MEP, and SSEP assessments.
Figure 2:
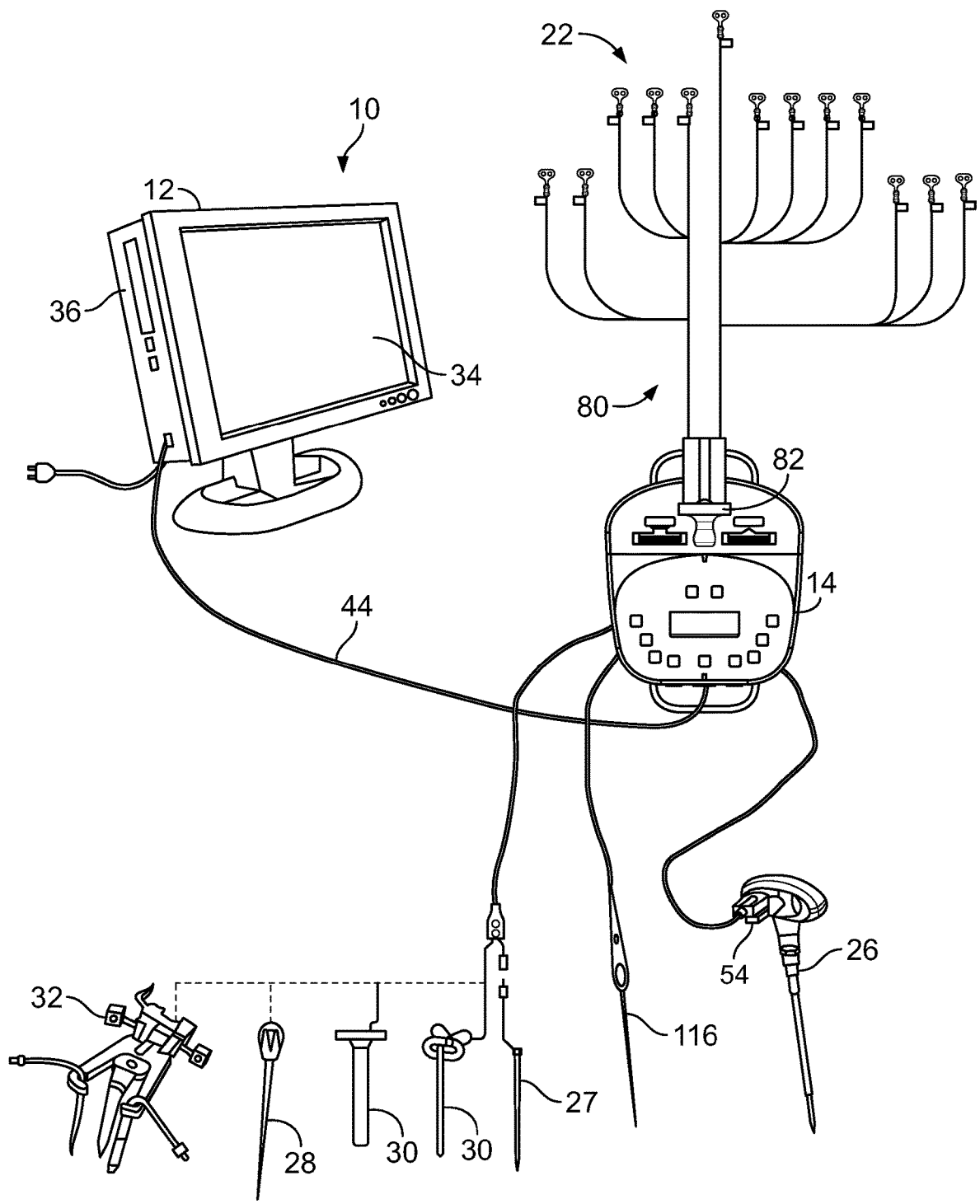
FIG. 2 is a perspective view showing examples of several components of the system of FIG. 1.

A neurophysiologic monitoring system 10 is described herein and is capable of performing a number of neurophysiological and/or guidance assessments at the direction of the surgeon (and/or other members of the surgical team). By way of example only, FIGS. 1-2 illustrate the basic components of the system 10. The system comprises a control unit 12 (including a main display 34 preferably equipped with a graphical user interface (GUI) and a processing unit 36 that collectively contain the essential processing capabilities for controlling the system 10), a patient module 14, a stimulation accessory (e.g. a stimulation probe 16, stimulation clip 18 for connection to various surgical instruments, an inline stimulation hub 20, and stimulation electrodes 22), and a plurality of recording electrodes 24 for detecting electrical potentials.

The stimulation accessories may be in the form of various prove devices that are themselves inserted into the stimulation site, clips that attach and deliver stimulation signals to standard instruments that are used at various times throughout a procedure . . . and surface electrodes. The stimulation clip 18 may be used to connect any of a variety of surgical instruments to the system 10, including, but not necessarily limited to a pedicle access needle 26, k-wire 27, tap 28, dilator(s) 30, tissue retractor 32, etc. One or more secondary feedback devices (e.g. secondary display 46 in FIG. 20-21) may also be provided for additional expression of output to a user and/or receiving input from the user.

In one embodiment, the system 10 may be configured to execute any of the functional modes including, but not necessarily limited to, neuromuscular pathway assessment ("Twitch Test"), non-evoked monitoring ("Free-run EMG"), static pedicle integrity testing ("Basic Stimulated EMG"), dynamic pedicle integrity testing ("Dynamic Stimulated EMG"), nerve proximity detection ("XLIF®"), motor evoked potential monitoring ("MEP Manual" and "MEP Automatic"), transcutaneous nerve root testing ("TCNR Alert" and "TCNR Threshold"), somatosensory evoked potential monitoring ("SSEP Manual" and "SSEP Automatic"), and surgical correction planning and assessment. The system 10 may also be configured for performance in any of the lumbar, thoracolumbar, and cervical regions of the spine.

Figure 3:
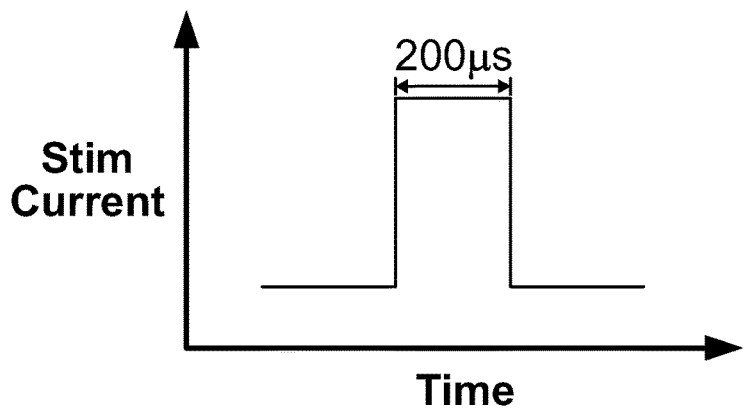
FIG. 3 is a graph illustrating a plot of a single pulse stimulation current signal capable of producing a neuromuscular response (EMG) of the type shown in FIG. 5.
Figure 4:
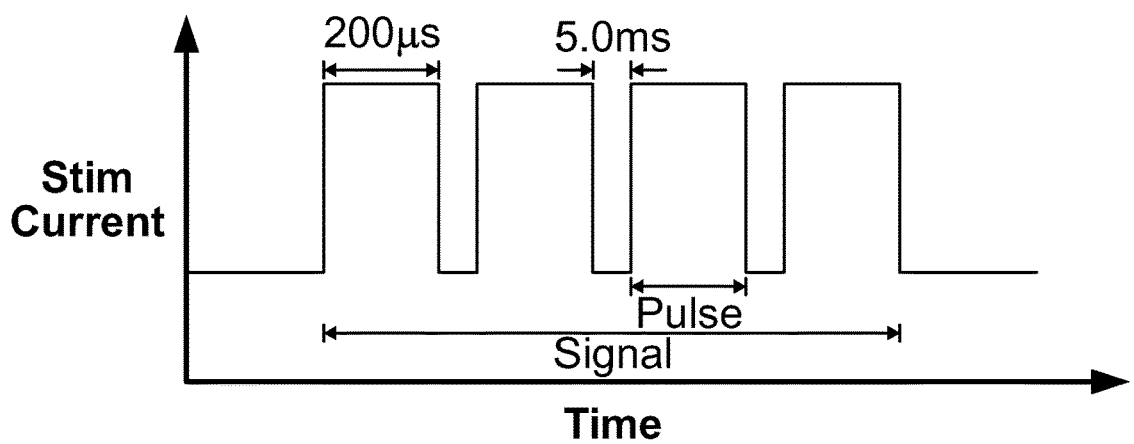
FIG. 4 is a graph illustrating [a] plot of a stimulation current signal comprising a train of pulses capable of producing a neuromuscular response (EMG) of the type shown in FIG. 5.
Figure 5:
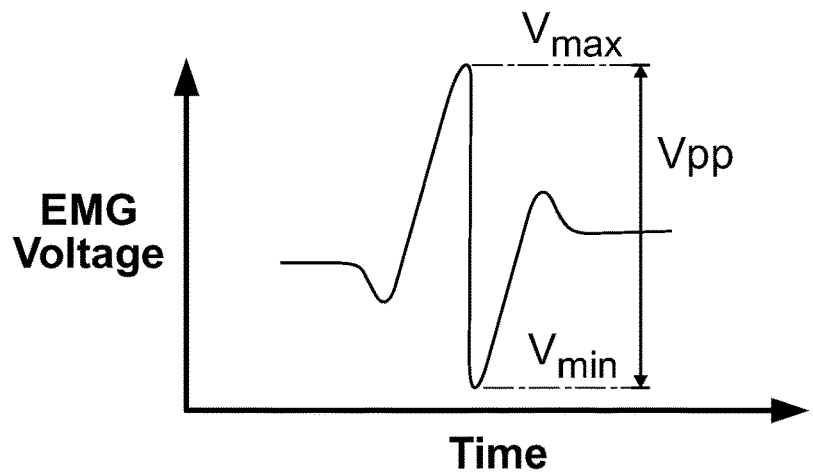
FIG. 5 is a graph illustrating a plot of the neuromuscular response of a given myotome over time based on a stimulation signal (such as shown in either FIG. 4 or FIG. 5)

The basis for performing many of these functional modes (e.g. Twitch Test, Basic Stimulated EMG, Dynamic Stimulated EMG, XILF, MEP Manual, MEP Automatic, TCNR Alert, and TCNR Threshold) is the assessment of evoked responses of the various muscles myotomes monitored by the system 10 in relation to a stimulation signal transmitted by the system 10 (via patient module 14). The assessment of the evoked responses can be any suitable means of sensing physical motion of a muscle, for example via mechanomyography (MMG) which in one embodiment entails using an accelerometer or other similar device for detecting mechanical movement of a muscle or via electromyography (EMG) which is described in detail herein. This is illustrated in FIGS. 3-5, wherein FIG. 5 illustrates the resulting EMG waveform of a monitored myotome in response to one of the example stimulation signals represented in FIG. 3 and FIG. 4. The EMG responses provide a quantitative measure of the nerve depolarization caused by the electrical stimulus. One way to characterize the EMG response is by a peak-to-peak voltage of $V_{pp}=V_{max}-V_{min}$, as shown in FIG. 5. Nerve tissues have characteristic threshold current levels ($I_{thresh}$) at which they will depolarize and result in a detectable muscle activity. Below this threshold current level, a stimulation signal will not evoke a significant EMG response. According to one embodiment, a significant EMG response may be defined as having a $V_{pp}$ of approximately 100 uV. Thus, the lowest stimulation current necessary to evoke an EMG response of the threshold voltage ($V_{thresh}$), 100 uV in this example, may be called $I_{thresh}$. The greater the degree of electrical communication between a stimulation signal and a nerve, the lower $I_{thresh}$ will be. Conversely, the lower the degree of electrical communication between a stimulation signal and a nerve, the greater $I_{thresh}$ will be. Thus determining $I_{thresh}$, and/or monitoring changes in $I_{thresh}$ over time, may provide valuable information when nerve tissues are at risk during a surgical procedure, as will be discussed in more detail below. By way of example, an excessively high $I_{thresh}$ or an increase over a previous measurement during MEP testing may indicate a problem in the spinal cord or other portion of the motor pathway inhibiting transmission (communication) of the stimulation signal to the nerve. Meanwhile, during the Basic Stimulated EMG or Dynamic Stimulated EMG modes and the XLIF mode, a low $I_{thresh}$ value may indicate a breach in the pedicle allowing the electrical signal to transmit through the pedicle, or the close proximity of a nerve to the stimulation source, respectively. Armed with the useful information conveyed by $I_{thresh}$, the surgeon may detect a problem or potential problem early and then act to avoid and/or mitigate the problem. The neurophysiology system 10 may quickly and accurately determine $I_{thresh}$ under the direction and operation of the surgeon (if desired) and convey the useful information $I_{thresh}$ contains in a simple and easily comprehensible manner for interpretation by the surgeon.

Before further addressing the various functional modes of the surgical system 10, the hardware components and features of the system 10 will be describe in further detail. The control unit 12 of the system 10, illustrated by way of example only in FIG. 6, includes a main display 34 and a processing unit 36, which collectively contain the essential processing capabilities for controlling the system 10. The main display 34 is preferably equipped with a graphical user interface (GUI) capable of graphically communicating information to the user and receiving instructions from the user. The processing unit 36 contains computer hardware and software that commands the stimulation source (e.g. patient module 14, FIGS. 7-9), receives digital and/or analog signals and other information from the patient module 14, processes EMG and SSEP response signals, and displays the processed data to the user via the display 34. The primary functions of the software within the control unit 12 include receiving user commands via the touch screen main display 34, activating stimulation in the appropriate mode (Twitch Test, Basic Stimulated EMG, Dynamic Stimulated EMG, XLIF, MEP Manual, MEP Automatic, TCNR Alert, TCNR Threshold, SSEP Manual, and SSEP Automatic), processing signal data according to defined algorithms, displaying received parameters and processed data, and monitoring system status. According to one example embodiment, the main display 34 may comprise a 15" LCD display equipped with suitable touch screen technology and the processing unit 36 may comprise a 2 GHz. The processing unit 36 shown in FIG. 6 further includes a powered USB port 38 for connection to the patient module 14, a media drive 40 (e.g. CD, CD-RW, DVD, DVD-RW, etc. . . . ), a network port, wireless network card, and a plurality of additional ports 42 (e.g. USB, IEEE 1394, infrared, etc. . . . ) for attaching additional accessories, such as for example only, navigated guidance sensors, auxiliary stimulation anodes, and external devices (e.g. printer, keyboard, mouse, etc. . . . ). Preferably, during use the control unit 12 sits near the surgical table but outside the surgical field, such as for example, on a table top or a mobile stand. It will be appreciated, however, that if properly draped and protected, the control unit 12 may be located within the surgical (sterile) field.

Figure 6:
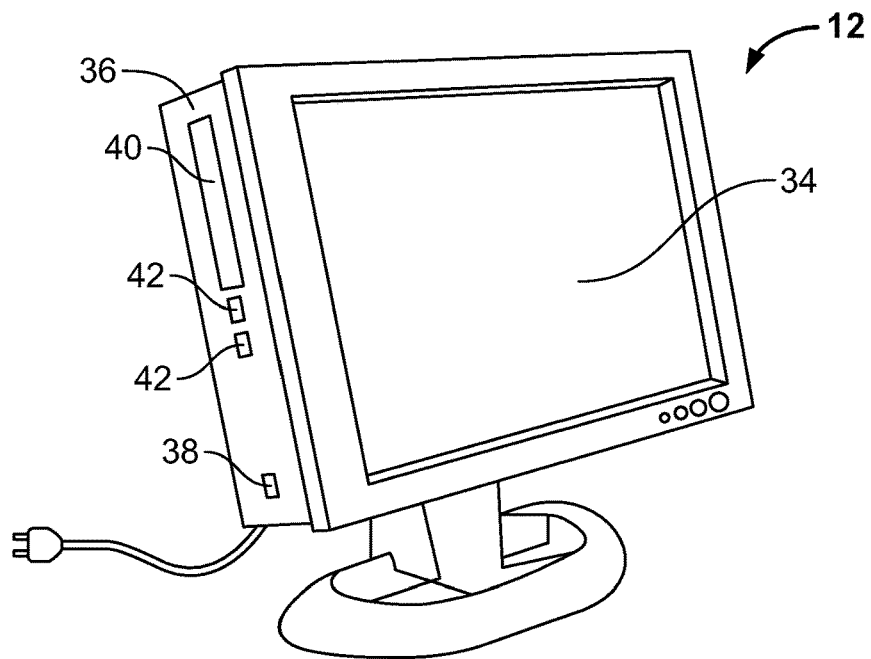
FIG. 6 is a perspective view of an example of a control unit forming part of the system of FIG. 1.

The patient module 14, shown by way of example only in FIGS. 4-6, is communicatively linked to the control unit 12. In this embodiment the patient module 14 is communicatively linked with and receives power from the control unit 12 via a USB data cable 44. However, it will be appreciated that the patient module 14 may be supplied with its own power source and other known data cables, as well as wireless technology, may be utilized to establish communication between the patient module 14 and control unit 12. The patient module 14 contains a digital communications interface to communicate with the control unit 12, as well as the electrical connections to all recording and stimulation electrodes, signal conditioning circuitry, stimulator drive and steering circuitry, and signal conditioning circuitry required to perform all of the functional modes of the system 10, including but not necessarily limited to Twitch Test, Free-run EMG, Basic Stimulated EMG, Dynamic Stimulated EMG, XLIF, MEP Manual and MEP Automatic, TCNR Alert, TCNR Threshold, SSEP Manual, and SSEP Automatic. In one example, the patient module 14 includes thirty-two recording channels and eleven stimulation channels. A display (e.g. an LCD screen) may be provided on the face of the patient module 14, and may be utilized for showing simple status readouts (for example, results of a power on test, the electrode harnesses attached, and impedance data, etc. . . . ) or more procedure related data (for example, a stimulation threshold result, current stimulation level, selected function, etc. . . . ). The patient module 14 may be positioned near the patient in the sterile field during surgery. By way of example, the patient module 14 may be attached to bed rail with the aid of a hook 48 attached to, or forming a part of, the patient module 14 casing.

Figure 7:
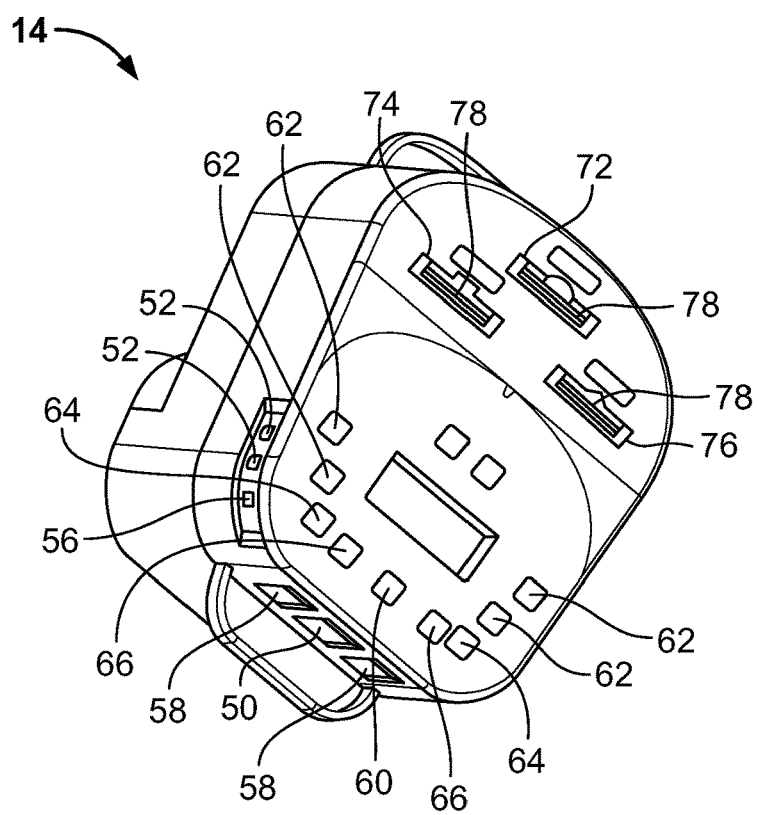
FIGS. 7-9 are perspective, top, and side views, respectively, of an example of a patient module forming part of the system of FIG. 1.
Figure 8:
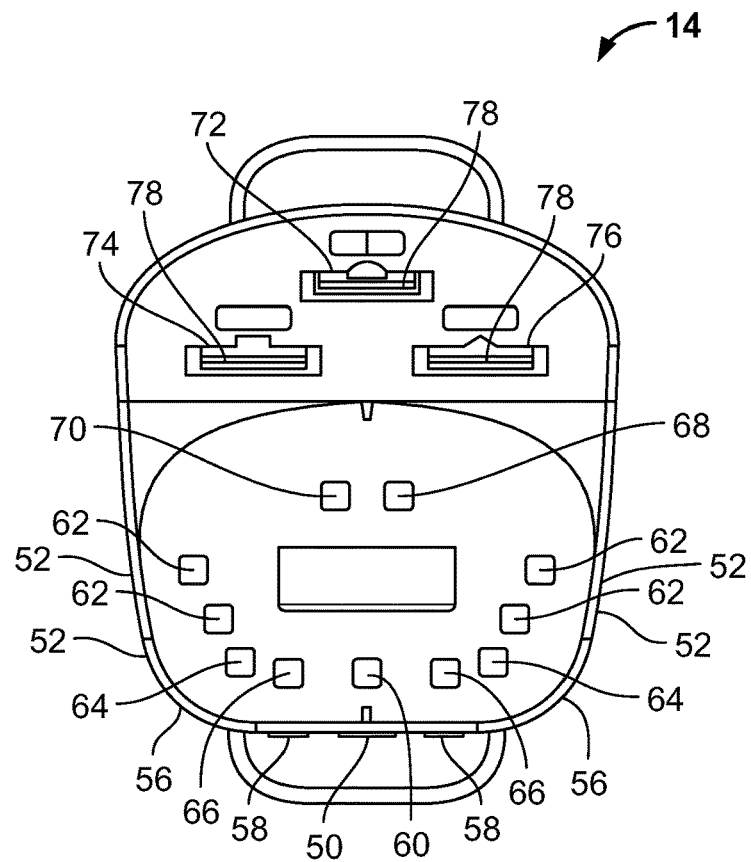
Figure 9:
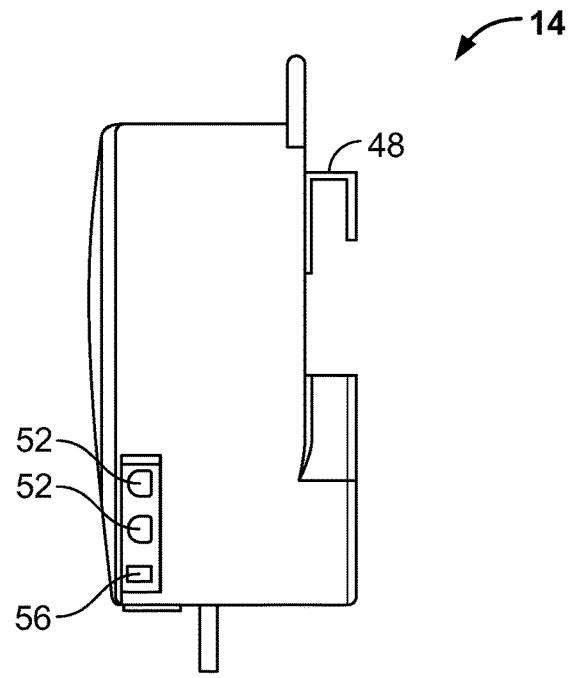

With reference to FIGS. 7-9, patient module 14 comprises a multitude of ports and indicators for connecting and verifying connections between the patient module 14 and other system components. A control unit port 50 is provided for data and power communication with the control unit 12, via USB data cable 44 as previously described. There are four accessory ports 52 provided for connecting up to the same number of surgical accessories, including, but not necessarily limited to, stimulation probe 16, stimulation clip 18, inline stimulation hub 20, and navigated guidance sensor (or tilt sensor) 54. The accessory ports 52 include a stimulation cathode and transmit digital communication signals, tri-color LED drive signals, button status signals, identification signals, and power between the patient module 14 and the attached accessory. A pair of anode ports 56, preferably comprising 2 wire DIN connectors, may be used to attach auxiliary stimulation anodes should it become desirable or necessary to do so during a procedure. A pair of USB ports 58 are connected as a USB hub to the control unit 12 and may be used to make any number of connections, such as for example only, a portable storage drive.

As soon as a device is plugged into any one of ports 50, 52, 56, or 58, the system 10 automatically performs a circuit continuity check to ensure the associated device will work properly. Each device forms a separate closed circuit with the patient module such that the devices may be checked independent of each other. If one device is not working properly the device may be identified individually while the remaining devices continue indicate their valid status. An indicator LED is provided for each port to convey the results of the continuity check to the user. Thus, according to the example embodiment of FIGS. 7-9, the patient module 14 includes one control unit indicator 60, four accessory indicators 62, two anode indicators 64, and two USB indicators 66. According to a preferred embodiment, if the system detects an incomplete circuit during the continuity check, the appropriate indicator will turn red alerting the user that the device might not work properly. On the other hand, if a complete circuit is detected, the indicator will appear green signifying that the device should work as desired. Additional indicator LEDs are provided to indicate the status of the system and the MEP stimulation. The system indicator 68 will appear green when the system is ready and red when the system is not ready. The MEP stim indicator 70 lights up when the patient module is ready to deliver and MEP stimulation signal. In one embodiment, the MEP stim indicator 68 appears yellow to indicate a ready status.

To connect the array of recording electrodes 24 and stimulation electrodes 22 utilized by the system 10, the patient module 14 also includes a plurality of electrode harness ports. In the embodiment shown, the patient module 14 includes an EMG/MEP harness port 72, SSEP harness port 74, an Auxiliary harness port 76 (for expansion and/or custom harnesses; e.g. a TCNR harness). Each harness port 72, 74, and 76 includes a shaped socket 78 that corresponds to a matching shaped connector 82 on the appropriate electrode harness 80. In addition, the system 10 may preferably employ a color code system wherein each modality (e.g. EMG, EMG/MEP, and SSEP) has a unique color associated with it. By way of example only and as shown herein, EMG monitoring (including, screw tests, detection, and nerve retractor) may be associated with the color green, MEP monitoring with the color blue, and SSEP monitoring may be associated with the color orange. Thus, each harness port 72, 74, 76 is marked with the appropriate color which will also correspond to the appropriate harness 80. Utilizing the combination of the dedicated color code and the shaped socket/connector interface simplifies the setup of the system, reduces errors, and can greatly minimize the amount of pre-operative preparation necessary. The patient module 14, and especially the configuration of quantity and layout of the various ports and indicators, has been described according to one example embodiment of the present invention. It should be appreciated, however, that the patient module 14 could be configured with any number of different arrangements without departing from the scope of the invention.

Figure 10:
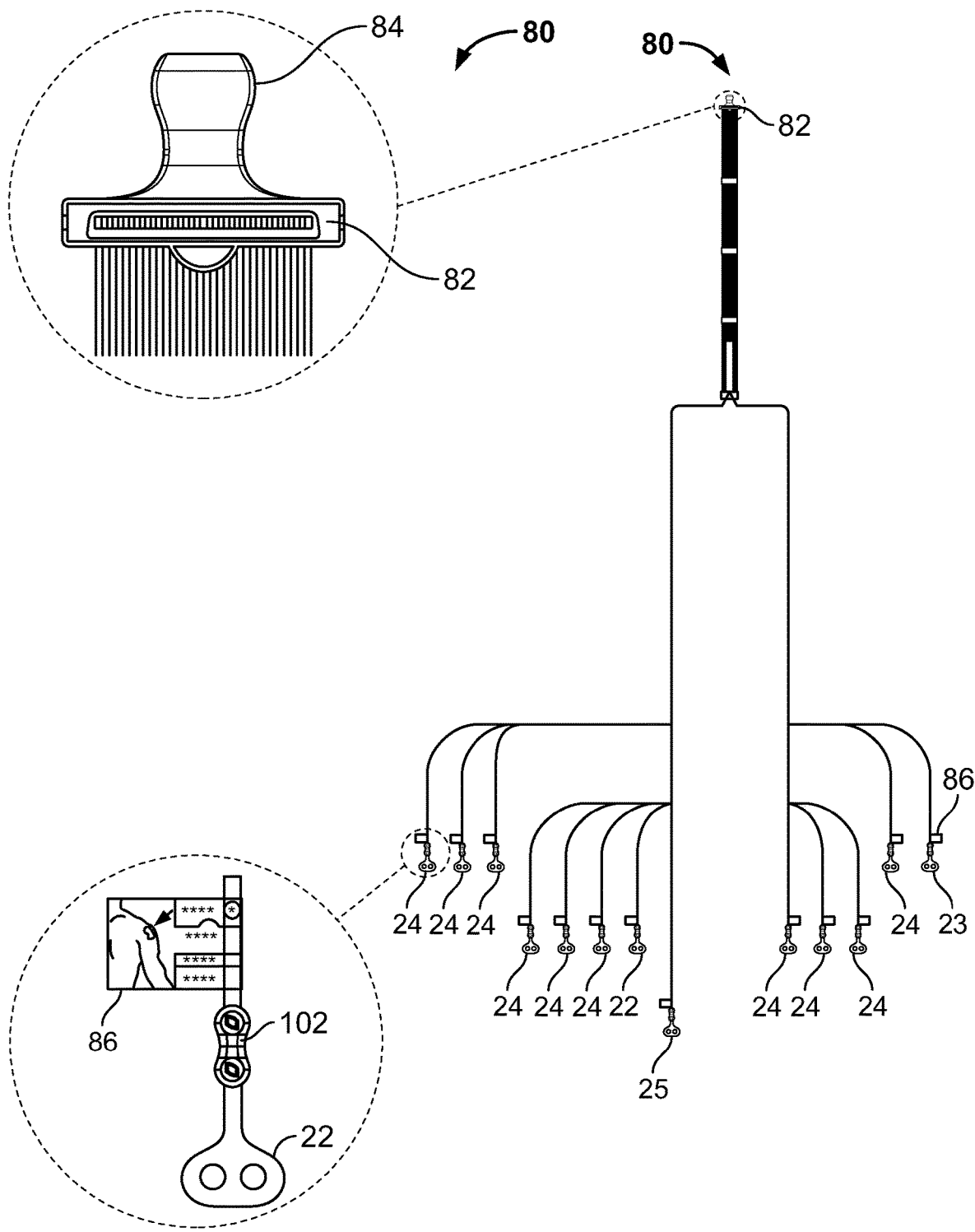
FIG. 10 is a top view of an electrode harness forming part of the system of FIG. 1.

As mentioned above, to simplify setup of the system 10, all of the recording electrodes 24 and stimulation electrodes 22 that are required to perform one of the various functional modes (including a common electrode 23 providing a ground reference to pre-amplifiers in the patient module 14, and an anode electrode 25 providing a return path for the stimulation current) are bundled together and provided in single electrode harness 80, as illustrated, by way of example only, in FIG. 10. Depending on the desired function or functions to be used during a particular procedure, different groupings of recoding electrodes 24 and stimulation electrodes 22 may be required. By way of example, the SSEP function requires more stimulating electrodes 22 than either the EMG or MEP functions, but also requires fewer recording electrodes than either of the EMG and MEP functions. To account for the differing electrode needs of the various functional modes, the system 10 may employ different harnesses 80 tailored for the desired modes. According to one embodiment, three different electrode harnesses 80 may be provided for use with the system 10, an EMG harness, an EMG/MEP harness, and an SSEP harness.

Figure 11A:
FIGS. 11A-11C are side views of various examples of harness ports forming part of the system of FIG. 1.
Figure 11B:
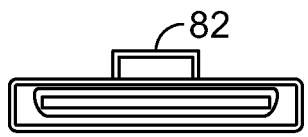
Figure 11C:
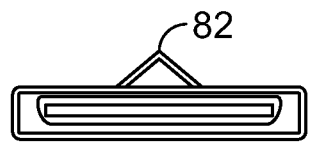

At one end of the harness 80 is the shaped connector 82. As described above, the shaped connector 82 interfaces with the shaped socket 72, 74, or 76 (depending on the functions harness 80 is provided for). Each harness 80 utilizes a shaped connector 82 that corresponds to the appropriate shaped socket 72, 74, 76 on the patient module 14. If the shapes of the socket and connector do not match the harness 80, connection to the patient module 14 cannot be established. According to one embodiment, the EMG and the EMG/MEP harnesses both plug into the EMG/MEP harness port 72 and thus they both utilize the same shaped connector 82. By way of example only, FIGS. 11A-11C illustrate the various shape profiles used by the different harness ports 72, 74, 76 and connectors 82. FIG. 11A illustrates the half circular shape associated with the EMG and EMG/MEP harness and port 72. FIG. 11B illustrates the rectangular shape utilized by the SSEP harness and port 74. Finally, FIG. 11C illustrates the triangular shape utilized by the Auxiliary harness and port 76. Each harness connector 82 includes a digital identification signal that identifies the type of harness 80 to the patient module 14. At the opposite end of the electrode harness 80 are a plurality of electrode connectors 102 linked to the harness connector 82 via a wire lead. Using the electrode connector 102, any of a variety of known electrodes may be used, such as by way of example only, surface dry gel electrodes, surface wet gel electrodes, and needle electrodes.

Figure 13A:
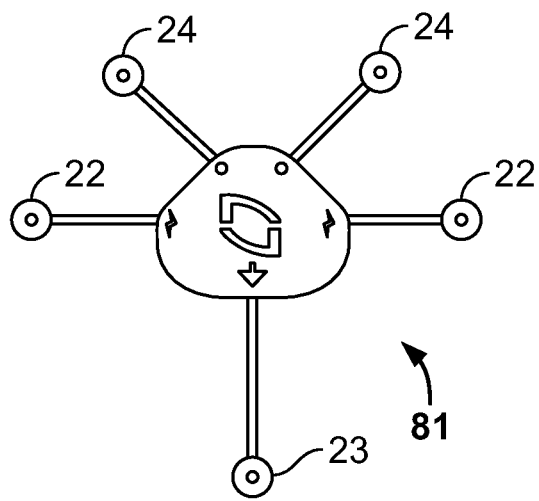
FIGS. 13A-13B are top views of examples of electrode caps forming part of the system of FIG. 1.
Figure 13B:
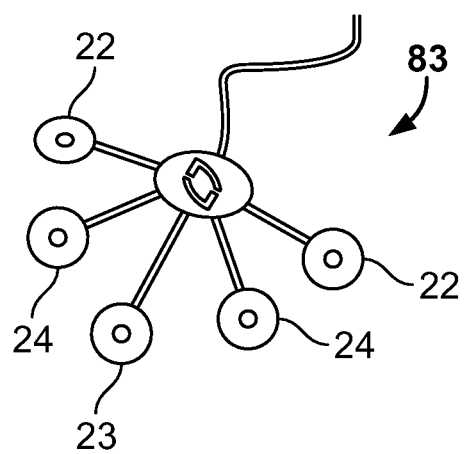

To facilitate easy placement of scalp electrodes used during MEP and SSEP modes, an electrode cap 81, depicted by way of example only in FIG. 13A may be used. The electrode cap 81 includes two recording electrodes 23 for SSEP monitoring, two stimulation electrodes 22 for MEP stimulation delivery, and an anode 23. Graphic indicators may be used on the electrode cap 81 to delineate the different electrodes. By way of example, lightning bolts may be used to indicate a stimulation electrode, a circle within a circle may be used to indicate recording electrodes, and a stepped arrow may be used to indicate the anode electrode. The anode electrode wire is colored white to further distinguish it from the other electrodes and is significantly longer that the other electrode wires to allow placement of the anode electrode on the patient's shoulder. The shape of the electrode cap 81 may also be designed to simplify placement. By way of example only, the cap 81 has a pointed end that may point directly toward the patient's nose when the cap 81 is centered on the head in the right orientation. A single wire may connect the electrode cap 81 to the patient module 14 or electrode harness 80, thereby decreasing the wire population around the upper regions of the patient. Alternatively, the cap 81 may be equipped with a power supply and a wireless antenna for communicating with the system 10. FIG. 13B illustrates another example embodiment of an electrode cap 83 similar to cap 81. Rather than using graphic indicators to differentiate the electrodes, colored wires may be employed. By way of example, the stimulation electrodes 22 are colored yellow, the recording electrodes 24 are gray, and the anode electrode 23 is white. The anode electrode is seen here configured for placement on the patient's forehead. According to an alternate embodiment, the electrode cap (not shown) may comprise a strap or set of straps configured to be worn on the head of the patient. The appropriate scalp recording and stimulation sites may be indicated on the straps. By way of example, the electrode cap may be imbued with holes overlying each of the scalp recording sites (for SSEP) and scalp stimulation sites (for MEP). According to a further example embodiment, the border around each hole may be color coded to match the color of an electrode lead wire designated for that site. In this instance, the recording and stimulation electrodes designated for the scalp are preferably one of a needle electrode and a corkscrew electrode that can be placed in the scalp through the holes in the cap.

As will be explained in greater detail below, the electrodes of different sizes and configurations may be preferable for the TCNR mode than for MEP, EMG, and SSEP modes. According to some implementations, the posterior cathode is a single use cathode electrode that has a circular shape (radially symmetric) to simplify positioning (superficially on the dorsal midline, approximately over the conus medullaris at the L1-L2 spinal level). The full contact surface is a conductive adhesive hydrogel to eliminate the need for skin prep. The connecting lead is made of insulated radiolucent carbon wire to avoid obscuring fluoroscopic images. The terminating 1.5 mm female DIN connector is color coded purple to maintain correct polarity corresponding with the mating harness connector. The anterior anode is a single use anode electrode has a square shape (radially symmetric) with a relatively large surface area to simplify positioning (superficially on the abdominal midline below the umbilicus) and increase the positioning location tolerance. The full contact surface is a conductive adhesive hydrogel to eliminate the need for skin prep. The connecting lead is made of insulated radiolucent carbon wire to avoid obscuring fluoroscopic images. The terminating 1.5 mm female DIN connector is color coded yellow maintain correct polarity corresponding with the mating harness connector.

Figure 12:
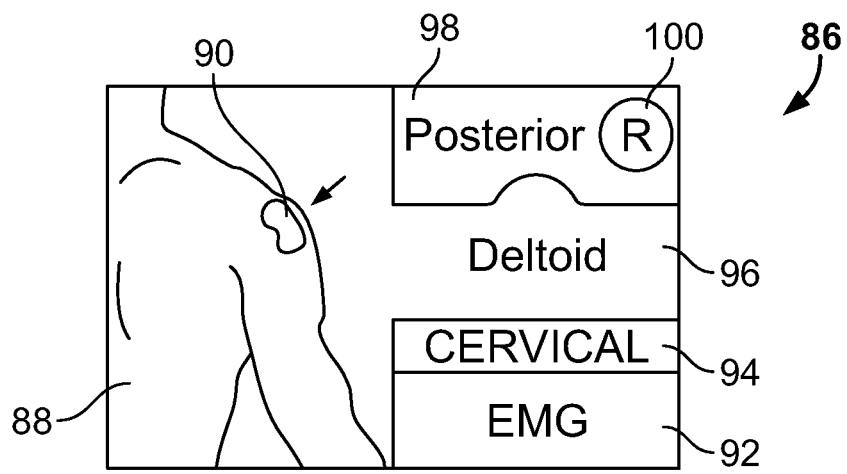
FIG. 12 is a plan view of an example of a label affixed to an electrode connector forming part of the system of FIG. 1.

In addition to or instead of color coding the electrode lead wires to designated intended placement, the end of each wire lead next to the electrode connector 102 may be tagged with a label 86 that shows or describes the proper positioning of the electrode on the patient. The label 86 preferably demonstrates proper electrode placement graphically and textually. As shown in FIG. 12, the label may include a graphic image showing the relevant body portion 88 and the precise electrode position 90. Textually, the label 86 may indicate the side 100 and muscle (or anatomic location) 96 for placement, the function of the electrode (e.g. stimulation, recording channel, anode, and reference—not shown), the patient surface (e.g. anterior or posterior), the spinal region 94, and the type of monitoring 92 (e.g. EMG, MEP, SSEP, by way of example, only). According to one embodiment (set forth by way of example only), the electrode harnesses 80 are designed such that the various electrodes may be positioned about the patient (and preferably labeled accordingly) as described in Table 1 for Lumbar EMG, Table 2 for Cervical EMG, Table 3 for Lumbar/Thoracolumbar EMG and MEP, Table 4 for Cervical EMG and MEP, Table 5 for TCNR, and Table 6 for SSEP:

TABLE 1

Lumbar EMG

| Electrode Type | Electrode Placement | Spinal Level |
| --- | --- | --- |
| Ground | Upper Outer Thigh | — |
| Anode | Latissimus Dorsi | — |
| Stimulation | Knee | — |
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |
| Recording | Right Biceps Femoris | L5, S1, S2 |

TABLE 1-continued

Lumbar EMG

| Electrode Type | Electrode Placement | Spinal Level |
| --- | --- | --- |
| Recording | Right Vastus Medialis | L2, L3, L4 |
| Recording | Right Gastroc. Medialis | S1, S2 |
| Recording | Right Tibialis Anterior | L4, L5 |

TABLE 2

Cervical EMG

| Electrode Type | Electrode Placement | Spinal Level |
| --- | --- | --- |
| Ground | Shoulder | — |
| Anode | Mastoid | — |
| Stimulation | Inside Elbow | — |
| Recording | Left Triceps | C7, C8 |
| Recording | Left Flexor Carpi Radialis | C6, C7, C8 |
| Recording | Left Deltoid | C5, C6 |
| Recording | Left Trapezius | C3, C4 |
| Recording | Left Vocal Cord | RLN |
| Recording | Right Vocal Cord | RLN |
| Recording | Right Trapezius | C3, C4 |
| Recording | Right Deltoid | C5, C6 |
| Recording | Right Flexor Carpi Radialis | C6, C7, C8 |
| Recording | Right Triceps | C7, C8 |

TABLE 3

Lumbar/Thoracolumbar EMG + MEP

| Electrode Type | Electrode Placement | Spinal Level |
| --- | --- | --- |
| Ground | Upper Outer Thigh | — |
| Anode | Latissimus Dorsi | — |
| Stimulation | Knee | — |
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |
| Recording | Left APB-ADM | C6, C7, C8, T1 |
| Recording | Right APB-ADM | C6, C7, C8, T1 |
| Recording | Right Biceps Femoris | L5, S1, S2 |
| Recording | Right Vastus Medialis | L2, L3, L4 |
| Recording | Right Gastroc. Medialis | S1, S2 |
| Recording | Right Tibialis Anterior | L4, L5 |

TABLE 4

Cervical EMG + MEP

| Electrode Type | Electrode Placement | Spinal Level |
| --- | --- | --- |
| Ground | Shoulder | — |
| Anode | Mastoid | — |
| Stimulation | Inside Elbow | — |
| Recording | Left Tibialis Anterior | L4, L5 |
| Recording | Left Flexor Carpi Radialis | C6, C7, C8 |
| Recording | Left Deltoid | C5, C6 |
| Recording | Left Trapezius | C3, C4 |
| Recording | Left APB-ADM | C6, C7, C8, T1 |
| Recording | Left Vocal Cord | RLN |
| Recording | Right Vocal Cord | RLN |
| Recording | Right APB-ADM | C6, C7, C8, T1 |
| Recording | Right Trapezius | C3, C4 |
| Recording | Right Deltoid | C5, C6 |
| Recording | Right Flexor Carpi Radialis | C6, C7, C8 |
| Recording | Right Tibialis Anterior | L4, L5 |

TABLE 5

Transcutaneous Nerve Root Stimulation

| Electrode Type | Electrode Placement | Spinal Level |
|---|---|---|
| Ground | Hip | — |
| Anode | Mid-back | — |
| Stimulation | L1-L2 cathode | — |
| Stimulation | Umbilicus anode | — |
| Recording | Left Adductor Magnus | L2, L3, L4 |
| Recording | Left Vastus Lateralis | L3, L4 |
| Recording | Left Tibialis Anterior | L4, L5 |
| Recording | Left Biceps Femoris | L5, S1, S2 |
| Recording | Right Adductor Magnus | L2, L3, L4 |
| Recording | Right Vastus Lateralis | L3, L4 |
| Recording | Right Vastus Medialis | L2, L3, L4 |
| Recording | Right Tibialis Anterior | L4, L5 |
| Recording | Right Biceps Femoris | L5, S1, S2 |

TABLE 6

SSEP

| Electrode Type | Electrode Placement | Spinal Level |
|---|---|---|
| Ground | Shoulder | — |
| Stimulation | Left Post Tibial Nerve | — |
| Stimulation | Left Ulnar Nerve | — |
| Stimulation | Right Post Tibial Nerve | — |
| Stimulation | Right Ulnar Nerve | — |
| Recording | Left Popliteal Fossa | — |
| Recording | Left Erb's Point | — |
| Recording | Left Scalp Cp3 | — |
| Recording | Right Popliteal Fossa | — |
| Recording | Right Erb's Point | — |
| Recording | Right Scalp Cp4 | — |
| Recording | Center Scalp Fpz | — |
| Recording | Center Scalp Cz | — |
| Recording | Center Cervical Spine | — |

Figure 14A:
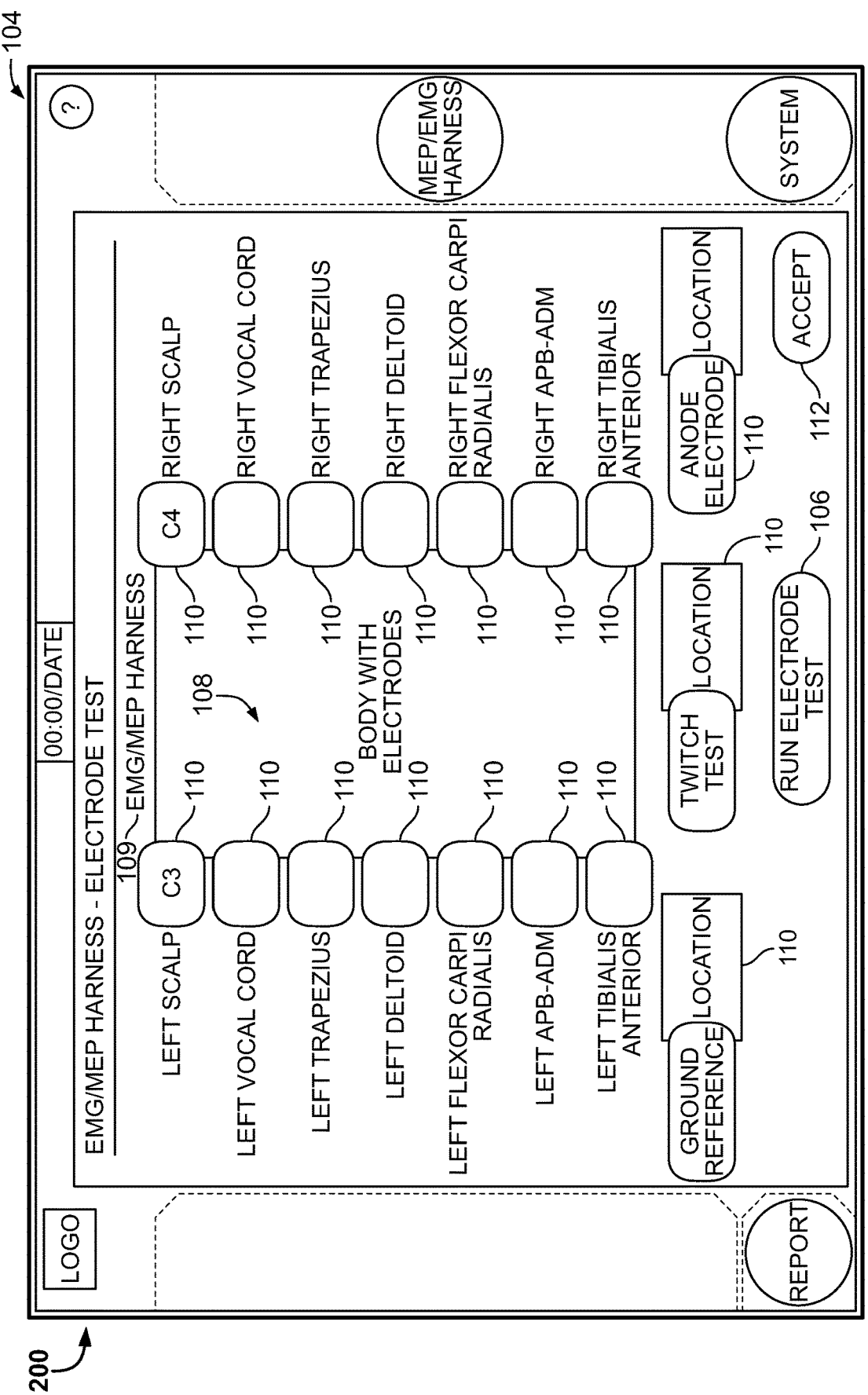
FIGS. 14A-14B are screenshots of an example embodiment of an electrode test screen forming part of the system of FIG. 1.
Figure 14B:
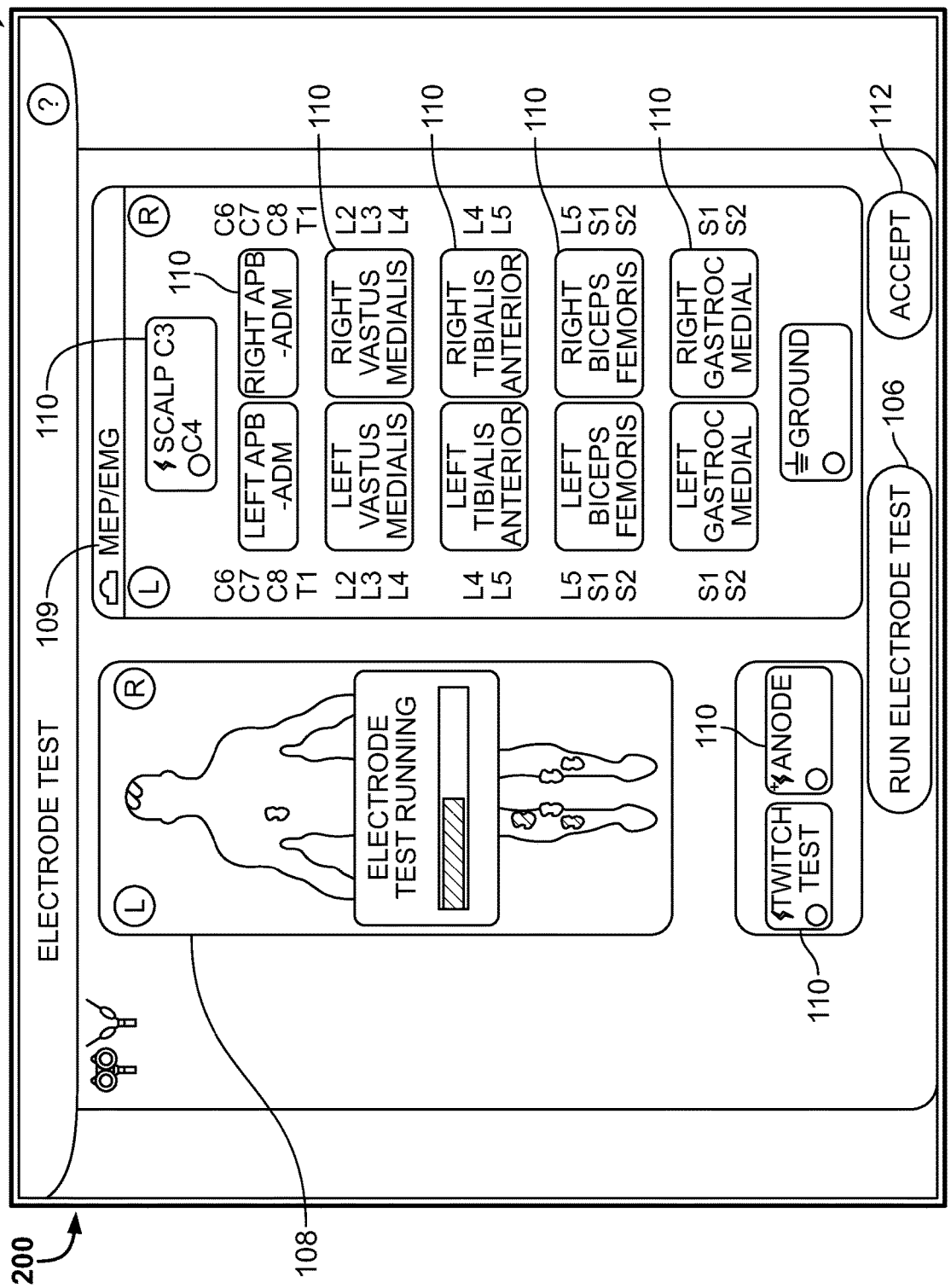

The patient module 14 is configured such that the system 10 may conduct an impedance test under the direction of the control unit 12 of all electrodes once the system is set up and the electrode harness is connected and applied to the patient. After choosing the appropriate spinal site upon program startup (described below), the user is directed to an electrode test. FIGS. 14A-14B illustrate, by way of example only, a graphical implementation capturing the features of an electrode test[s] as implemented on an electrode test screen 104. The electrode test screen 104 includes a human figure depiction with positioned electrodes 108. A harness indicator 109 displays which harness is in use. For each electrode on the harness 80 in use there is a channel button 110. This includes the common 25 and anode 23 electrodes which are both independently checked for impedance. To accomplish this, the anode 23 and common 25 are both provided as dual electrodes. At least one of the anode leads on the anode electrode is reversible. During the impedance check, the reversible anode lead switches to a cathode such that the impedance between the leads can be measured. When the impedance test is complete, the reversible lead switches back to an anode. The channel button 110 may be labeled with the muscle or coverage area of the corresponding electrode. Selecting the channel button 110 will disable the channel. Disabled channels will not be tested for impedance and they will not be monitored for responses or errors unless reactivated. Upon selection of a start button 106 ("Run Electrode Test"), the system tests each electrode individually to determine the impedance value. If the impedance is determined to be within acceptable limits, the channel button 110 and electrode depiction on the human FIG. 108 turn green. If the impedance value for any electrode is not determined to be acceptable, the associated channel button 110 and electrode depiction turn red, alerting the user. Once the test is complete, selecting the "Accept" button 112 will open the main monitoring screen 200 of the system 10.

Figure 15:
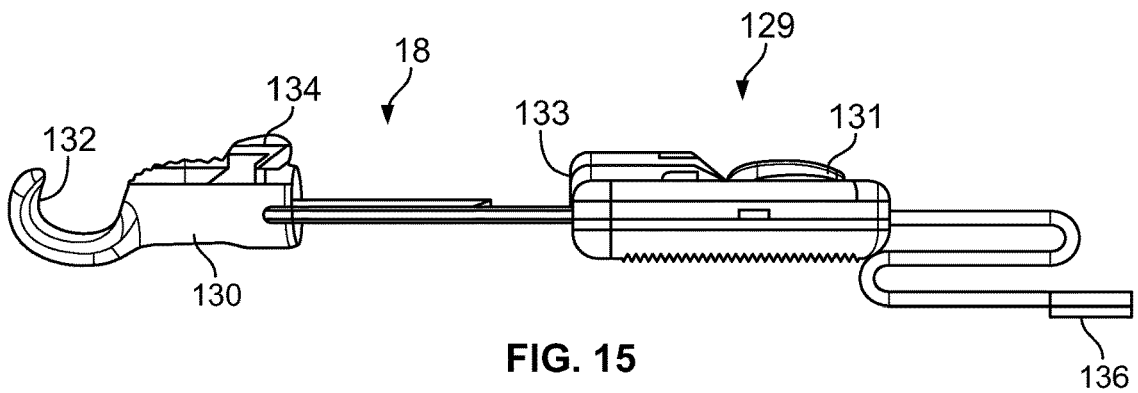
FIG. 15 is a perspective view of one embodiment of a stimulator forming part of the system of FIG. 1.
Figure 16:
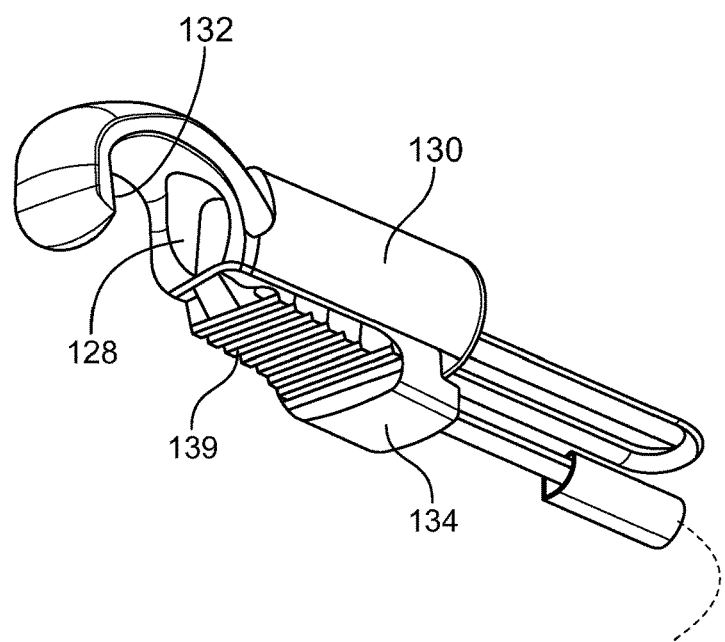
FIG. 16 is a perspective view of a second embodiment of a stimulator forming part of the system of FIG. 1.
Figure 17:
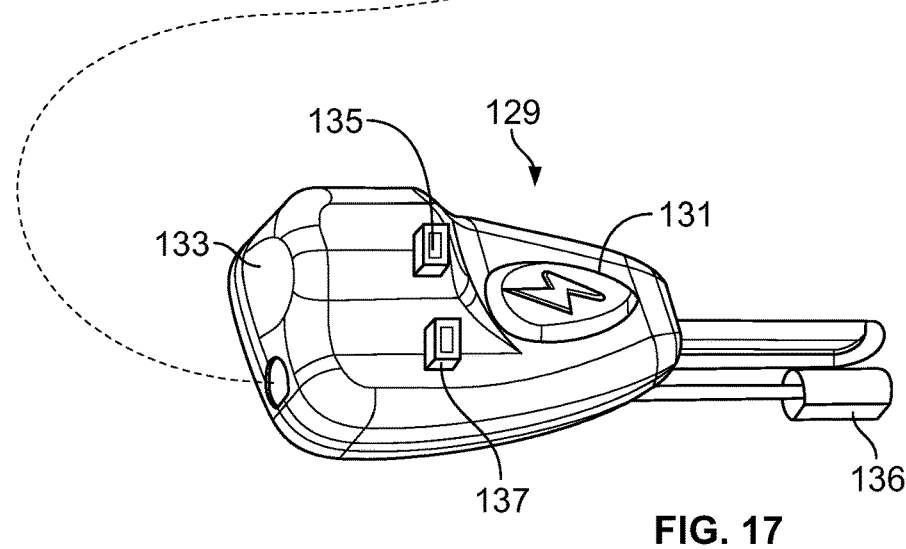
FIG. 17 is a perspective view of the stimulators of FIGS. 15 and 16 coupled together for use.

The system 10 may utilize various stimulation accessories to deliver stimulation signals to a stimulation target site such as over the patient's conus medullaris, a hole formed or being formed in a pedicle, and/or tissue surrounding an access corridor. FIGS. 15-17 illustrate an example embodiment of a stimulation accessory in the form of a stimulation clip 18 that permits the system 10 to deliver stimulation signals through various surgical instruments already used during the surgical procedure. By way of example only, the coupling device 18 may connect the system 10 with instruments including, but not necessarily limited to, a pedicle access needle 26, a tap 28, dilator 30, tissue retractor 32, and k-wire 27. The stimulation clip 18 utilizes a spring-loaded plunger 128 to hold the surgical tool and transmit the stimulation signal thereto. The plunger 128 is composed of a conductive material such as metal. A nonconductive housing 130 partially encases the plunger 128 about its center. Extending from the housing 130 is an endplate 132 that hooks the surgical instrument. A spring (not shown) is disposed within the housing 130 such that in a natural or "closed" state, the plunger 128 is situated in close proximity to the endplate 132. Exerting a compressive force on the spring (such as by pulling on the thumb grip 134) causes a gap between the end plate 132 and the plunger 128 to widen to an "open" position (shown in FIGS. 15-17 thereby allowing insertion of a surgical tool between the endplate 132 and plunger 128. Releasing the thumb grip 134 allows the spring to return to a "closed" position, causing the plunger 132 to move laterally back towards the endplate such that a force is exerted upon the surgical instrument and thereby holding it in place between the endplate 132 and the plunger 128. The clip 18 further includes a button module 129 containing an activation button 131 for initiating stimulation. The button module 129 is set apart from the body of the clip 18 and they are linked by an integrated wire. An accessory port 133 is located next to the button 131 on the button module 129, thus minimizing the number of wires connecting back to the patient module 14 and outside the sterile field. Clip 18 is equipped with three LEDs 135, 137, and 139. LED 135 is associated with the accessory port 133 and LED 137 is associated with the clip 18 to indicate which of the two is stimulating. The LEDs 137 and 137 may appear purple when stimulation is active. When a stimulation result is determined, the associated LED 135 or 137 may appear either red (if the result meets a predetermined potentially unsafe value), green (if the result meets a predetermined safe value), or yellow (if the result is in between the safe and potentially unsafe values). A third LED 139 is contained within the thumb grip 134, which will appear red, yellow, or green depending on the threshold result. The clip 18 connects to one of the accessory ports 62 on the patient module 14 via a connector 136. The connector 136 includes an identification signal that identifies it to the patient module.

Figure 18A:
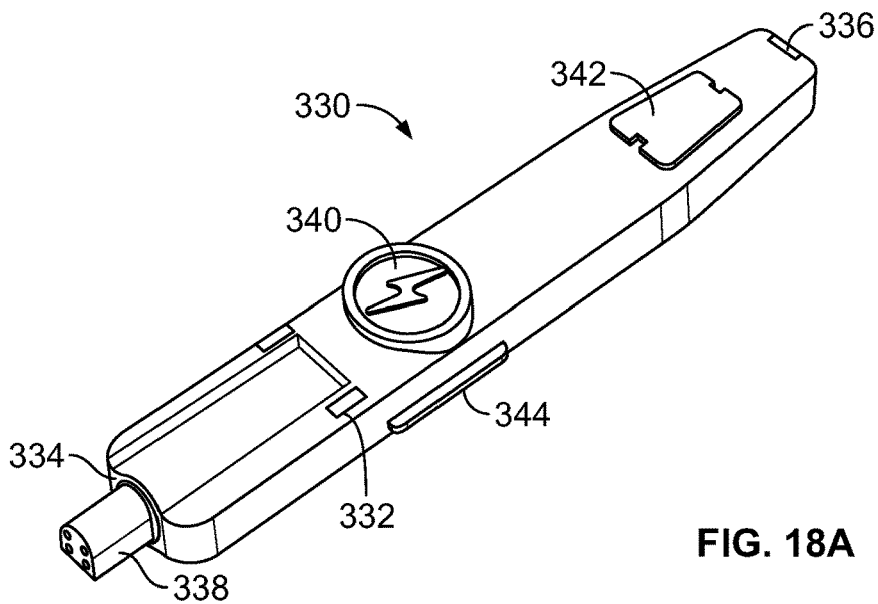
FIGS. 18A-18B are perspective views third and fourth embodiments a stimulators forming part of the system of FIG. 1.
Figure 18B:
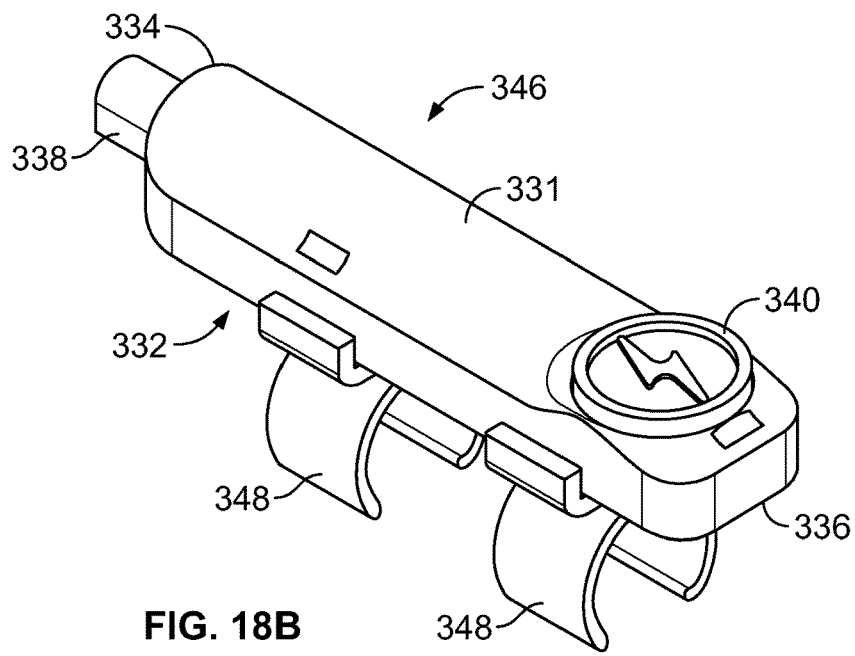
Figure 19:
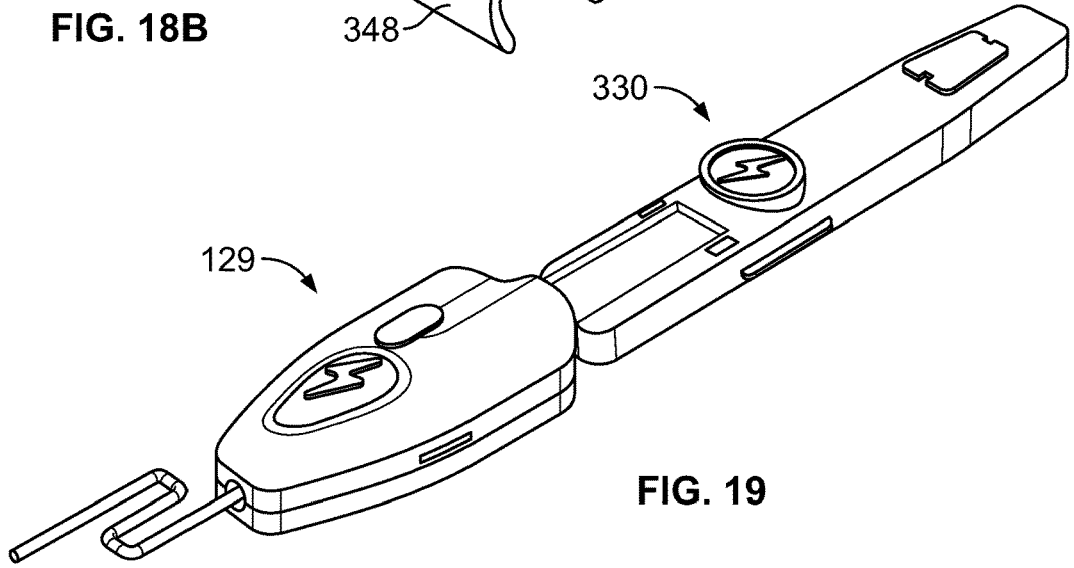
FIG. 19 is a perspective view of the stimulators of FIGS. 18A and 16 coupled together for use.

FIG. 18A illustrates a second example of embodiment of a stimulation accessory in the form of an in-field activator 330. The activator 330 is preferably a single-use sterile device and may be designed [as] a stand-alone device designed to interface with the patient module 14 independently or may be part of an assembly as will be explained below. According to one embodiment, the activator 330 may plug into an accessory port 133 of the stimulation clip 18 of FIGS. 15-17 above to provide user control and status indication of the TCNR mode from inside the sterile field during het surgical procedure. FIG. 19 shows the activator 330 plugged into accessory port 133 for in-field use. It is contemplated that the activator 330 is compatible with module 129 such that the activator 330 and clip 18 may be jointly connected to the system 10 via module 129 without the need for additional components, additional wires, and the like. The activator 330 includes a top 331, a bottom 332, a housing 333, a first end 334, a second end 336, a connection plug 338 emanating from said first end 334, a stimulation button 334 and a multi-color LED indicator 342 disposed between ends 334, 336. The connection plug 338 is sized and dimensioned to fit within the accessory port 133. Activator 330 may include one or more securing clips 348 (FIG. 18B) for securing the activator 330 to a surgical implement, such as, for example, an articulating arm or a retractor (not shown). The activator 330/stimulation clip 18 assembly may be connected to one of the accessory ports 62 on the patient module 14 via a connector 136. The connector 136 includes an identification signal that identifies it to the patient module. Upon connection of the activator 330, the system 10 software will enable TCNR mode, placing the icon for the mode on the test selection tab 204, as well as enabling configuration and other settings within the profiles and set up screens.

The activator button 340 allows a user from the sterile field to both navigate to the TCNR mode and initiate trans-abdominal, transcutaneous stimulation in TCNR modes with a single button press. By way of example only, the activator 330 may allow a user to both access the TCNR mode and initiate TCNR stimulation with a single button press as will be described in greater detail below. The activation button 340 may be circular and is protected from unintended activation by a raised surrounding border. Finger grips 334 may be provided on the sides of the activator housing 332 near activation button 340 to stabilize the activator 330 during use.

The activator 342 is equipped with a multi-color LED indicator 342. In some embodiments (e.g. that shown in FIG. 18A), the stimulation button 340 and the LED indicator 342 are two distinct components. In other embodiments (e.g. that shown in FIG. 18B), the LED indicator 342 is integrated into the stimulation button 340. LED indicator 342 provides feedback to the user of various states of operation of the TCNR modality. By way of example only, LED indicator 342 will illuminate when the timer has expired, when the stimulator button 340 has been pressed and when the system 10 is delivering stimulation.

TABLE 7

| LED Visual Feedback | Indication or Assessment |
| --- | --- |
| Off | Timer not elapsed, stimulation is inactive, or modality not selected |
| Blinking Green 1 Hz rat | Primary timer (default 5 min) has elapsed since last stimulation |
| Blinking Green 2 Hz rate | Secondary timer (default 10 min) has elapsed since last stimulation |
| Blinking Amber 4 Hz rate | Stimulation is active |
| Solid Green | Previous result- no significant change from baseline |
| Steady Yellow | Previous result- noteworthy change from baseline |
| Steady Red | Previous result- significant change from baseline |

Figure 20:
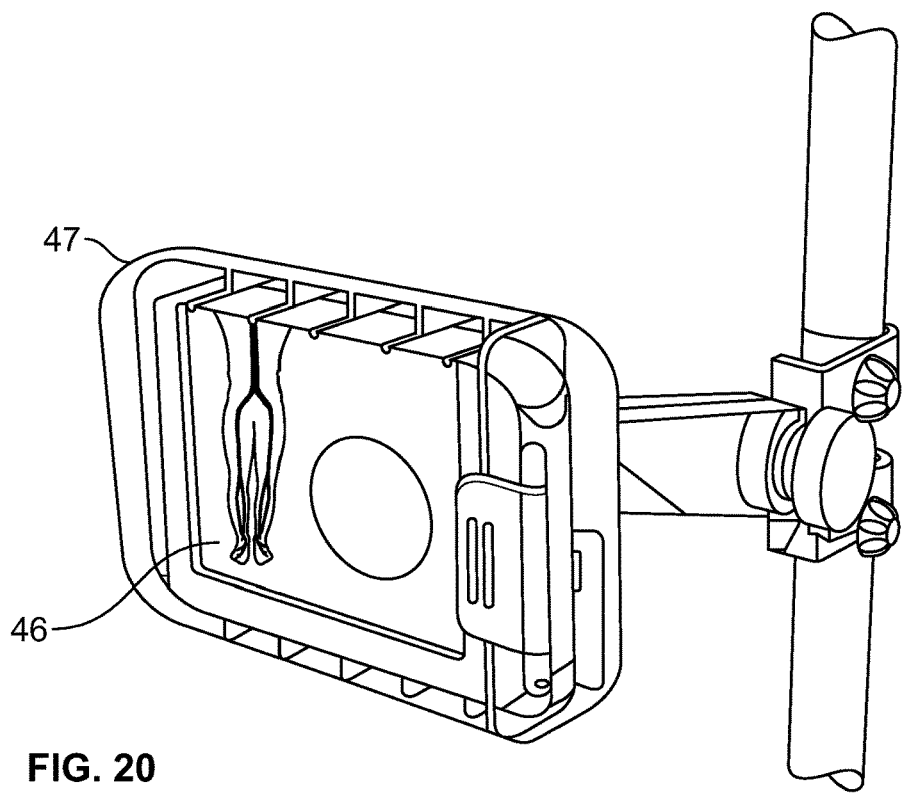
FIGS. 20-21 are perspective views of an example of a secondary display forming part of the system of FIG. 1.
Figure 21:
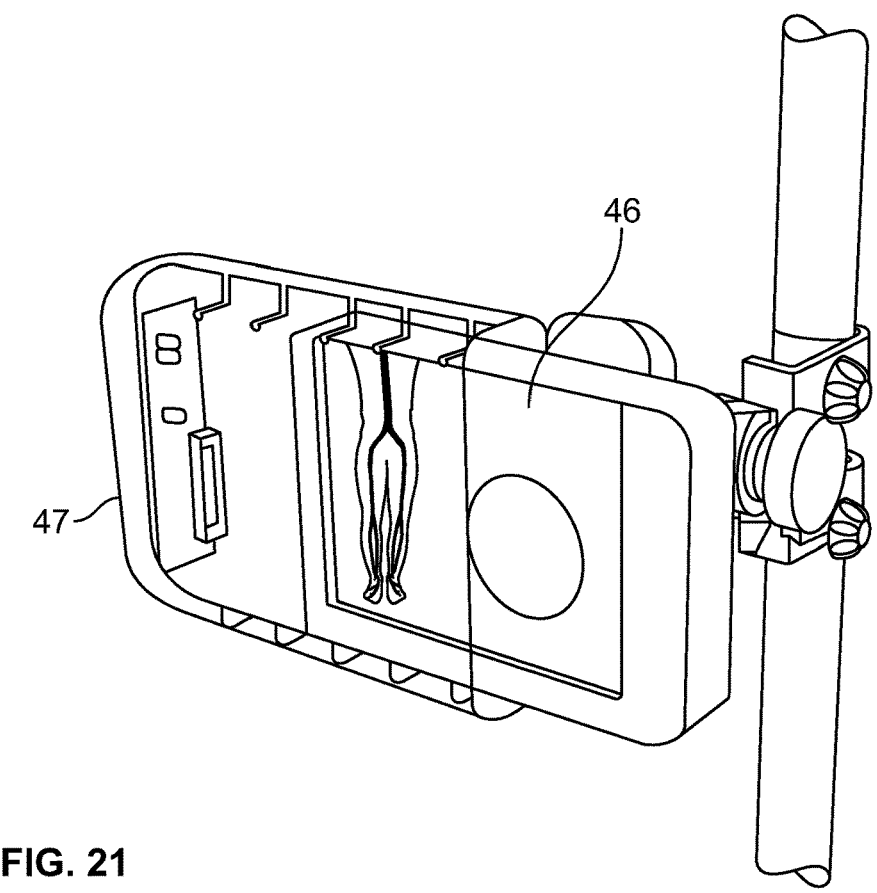

As mentioned above, the system 10 may include a secondary display, such as for example only, the secondary display 46 illustrated in FIGS. 20-21. The secondary display 46 may be configured to display some or all of the information provided on main display 34. The information displayed to the user on the secondary display 34 may include, but is not necessarily limited to, alpha-numeric and/or graphical information regarding any of the selected function modes (e.g. Twitch Test, Free-Run EMG, Basic Stimulated EMG, Dynamic Stimulated EMG, XLIF, MEP Manual, MEP Automatic, TCNR Alert, TCNR Threshold, SSEP Manual, SSEP Automatic, and surgical correction planning and assessment), attached accessories (e.g. stimulation probe 16, stimulation clip 18, tilt sensor 54), electrode harness or harnesses attached, impedance test results, myotome/EMG levels, stimulation levels, history reports, selected parameters, test results, etc. . . . In one embodiment, secondary display 46 may be configured to receive user input in addition to its display function. The secondary display 46 can thus be used as an alternate control point for the system 10. The control unit 12 and secondary display 46 may be linked such that input may be received on from one display without changing the output shown on the other display. This would allow the surgeon to maintain focus on the patient and test results while still allowing other members of the OR staff to manipulate the system 10 for various purposes (e.g. inputting annotations, viewing history, etc. . . . ). The secondary display 46 may be battery powered. Advantageously, the secondary display 46 may be positioned inside the sterile field as well as outside the sterile field. For positioning within the sterile field a disposable sterile case 47 may be provided to house the display. Alternatively, the display 46 may be sterile bagged. Both the sterile case 47 and the secondary display 46 may be mounted to a pole, bed frame, light fixture, or other apparatus found near and/or in the surgical field. It is further contemplated that multiple secondary displays 46 may be linked to the control unit 12. This may effectively distribute neurophysiology information and control throughout the operating room. By way of example, a secondary display 46 may also be provided for the anesthesiologist. This may be particularly useful in providing the anesthesiologist with results from the Twitch Test and providing reminders about the use of paralytics, which may adversely affect the accuracy of the system 10. Wired or wireless technology may be utilized to link the secondary display 46 to the control unit 12.

Having described an example embodiment of the system 10 and the hardware components that comprise it, the neurophysiological functionality and methodology of the system 10 will now be described in further detail. Various parameters and configurations of the system 10 may depend upon the target location (i.e. spinal region) of the surgical procedure and/or user preference. In one embodiment, upon starting the system 10 the software will open to a startup screen, illustrated by way of example only, in FIG. 33. The startup screen includes a profile selection window 160 from which the user may select from one of the standard profiles (e.g. "Standard Cervical," "Standard Thoracolumbar," and "Standard Lumbar") or any custom profiles that have been previously saved to the system. Profiles may be arranged for selection, alphabetically, by spinal region, or by other suitable criteria. Profiles may be saved to the control unit hard drive or to a portable memory device, such as for example, a USB memory drive, or on a web server.

Selecting a profile configures the system 10 to the parameters assigned for the selected profile (standard or custom). The availability of different function modes may depend upon the profile selected. By way of example only, selecting the cervical and thoracolumbar spinal regions may automatically configure the options to allow selection of the Twitch Test, SSEP Manual, SSEP Automatic, Basic Stimulated EMG, Dynamic Stimulated EMG, XLIF, MEP Manual, MEP Automatic, Free-Run EMG modes, while selecting the lumbar region may automatically configure the options to allow selection of the Twitch Test, Basic, Difference, and Dynamic Stimulated EMG Tests, XLIF®, and Nerve Retractor modes. Default parameters associated with the various function modes may also depend on the profile selected, for example, the characteristics of the stimulation signal delivered by the system 10 may vary depending on the profile. By way of example, the stimulation signal utilized for the Stimulated EMG modes may be configured differently when a lumbar profile is selected versus when one of a thoracolumbar profile and a cervical profile.

As previously described above, each of the hardware components includes an identification tag that allows the control unit 12 to determine which devices are hooked up and ready for operation. In one embodiment, profiles may only be available for selection if the appropriate devices (e.g. proper electrode harness 80 and stimulation accessories) are connected and/or ready for operation. Alternatively, the software could bypass the startup screen and jump straight to one of the functional modes based on the accessories and/or harnesses it knows are plugged in. The ability to select a profile based on standard parameters, and especially on customized preferences, may save significant time at the beginning of a procedure and provides for monitoring availability right from the start. Moving on from the startup screen, the software advances directly to an electrode test screen and impedance tests, which are performed on every electrode as discussed above. When an acceptable impedance test has been completed, the system 10 is ready to begin monitoring and the software advances to a monitoring screen from which the neurophysiological monitoring functions of the system 10 are performed.

The information displayed on the monitoring screen may include, but is not necessarily limited to, alpha-numeric and/or graphical information regarding any of the functional modes (e.g. Twitch Test, Free-Run EMG, Basic Stimulated EMG, Dynamic Stimulated EMG, XLIF, MEP Manual, MEP Automatic, TCNR Alert, TCNR Threshold, SSEP Manual, SSEP Automatic, and surgical correction planning and assessment), attached accessories (e.g. stimulation probe 16, stimulation clip 18, tilt sensor 54), electrode harness or harnesses attached, impedance test results, myotome/EMG levels, stimulation levels, history reports, selected parameters, test results, etc. . . . In one embodiment, set forth by way of example only, this information displayed on a main monitoring screen may include, but is not necessarily limited to, the following components as set forth in Table 8:

TABLE 8

| Screen Component | Description |
| --- | --- |
| Patient Image/ Electrode layout | An image of the human body or relevant portion thereof showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Test Menu | A hideable menu bar for selecting between the available functional modes. |
| Device Bar | A hideable bar displaying icons and/or names of devices connected to the patient module. |
| Display Area | Shows procedure-specific information including stimulation results. |
| Color Indication | Enhances stimulation results with a color display of green, yellow, or red corresponding to the relative safety level determined by the system. |
| Stimulation Bar | A graphical stimulation indicator depicting the present stimulation status (i.e. on or off and stimulation current level), as well as providing for starting and stopping stimulation |
| Event Bar | A hideable bar that shows the last up to a selected number of previous stimulation results, provides for annotation of results, and a chat dialogue box for communicating with remote participants. |
| EMG waveforms | EMG waveforms may be optionally displayed on screen along with the stimulation results. |

Figure 22:
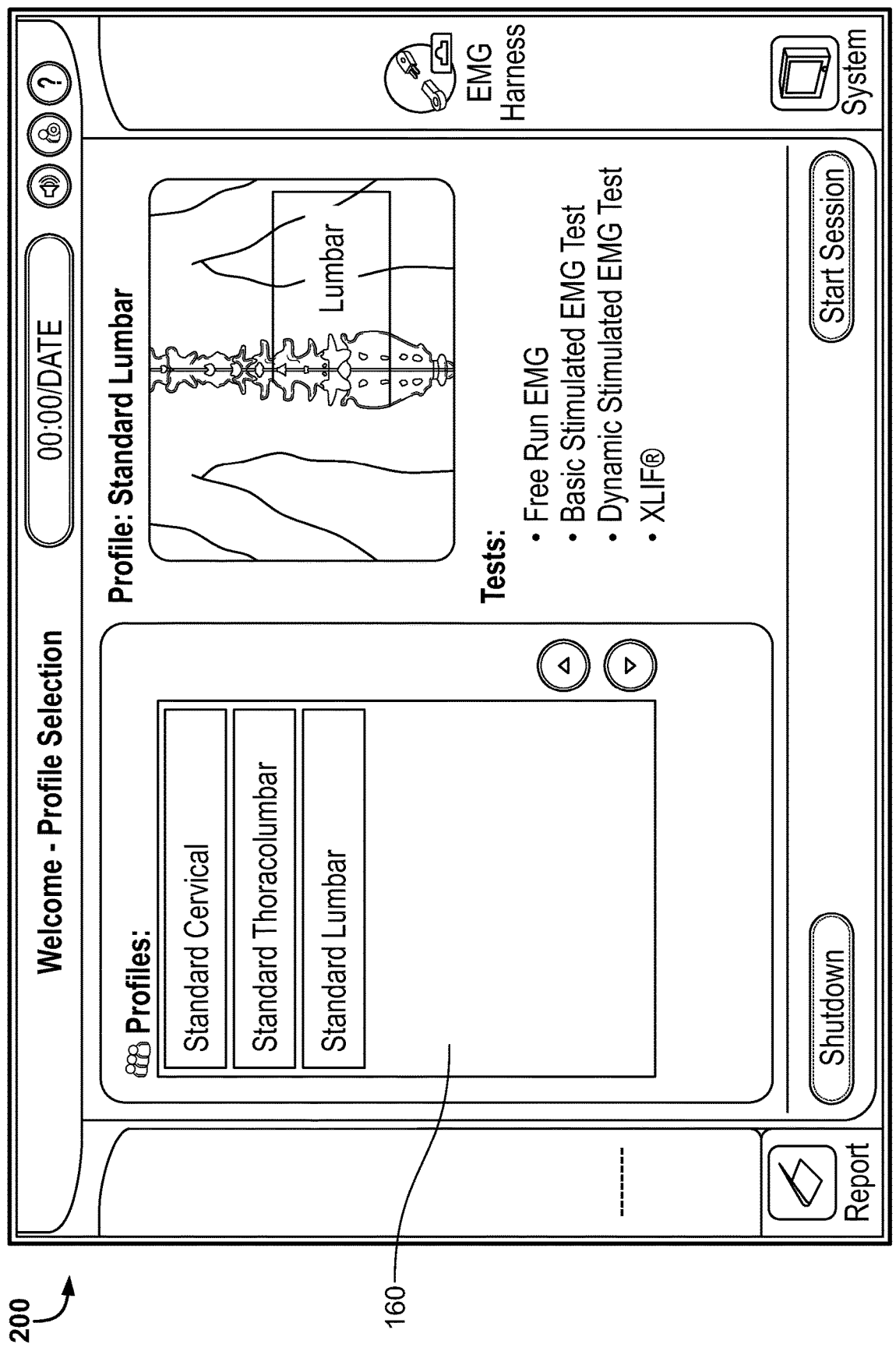
FIG. 22 is a first screenshot of an example embodiment of a TCNR Alert monitoring screen forming part of the neurophysiology system of FIG. 1.

From a profile setting window 160, custom profiles can be created and saved. Beginning with one of the standard profiles, parameters may be altered by selecting one of the various buttons and making the changes until the desired parameters are set. By way of example only, profiles may be generated and saved for particular procedures (e.g. ACDF, XLIF, and decompression), particular individuals, and combinations thereof. Clicking on each button will display the parameter options specific to the selected button in a parameter window. The parameter options for the Test Selection Window are illustrated by way of example in FIG. 22. By way of example only, by selecting the Test Selection button, session tests may be added and viewing options may be changed. From within the test selection area, function specific parameters for all available test functions (based on site selection, available devices, etc. . . . ) may be accessed and set according to need. One option (not shown) that is available for multiple functions under the test selection button is the ability to select from three different viewing options. The user may choose to see results displayed in numeric form, on a body panel, and on a label that reflects the labels associated with each electrode, or any combination of the three. FIGS. 23-38 illustrate examples of the test selection tab 204 for each of the test functions (e.g. Twitch Test, Basic Stimulated EMG, Dynamic Stimulated EMG, XLIF, TCNR Alert, TCNR Threshold, Free-Run, MEP Manual, MEP Automatic, SSEP Manual, SSEP Automatic). Profiles may be saved directly on the control unit 12, saved to a portable memory device, or uploaded onto a web-server.

The functions performed by the system 10 may include, but are not necessarily limited to, Twitch Test, Basic Stimulated EMG, Dynamic Stimulated EMG, XLIF®, Nerve Retractor, TCNR Alert, TCNR Threshold, Free-run EMG, MEP Manual, MEP Automatic, SSEP Manual, SSEP Automatic, and surgical correction planning and assessment modes, all of which will be described below. The Twitch Test mode is designed to assess the neuromuscular pathway via the so-called "train-of-four-test" to ensure the neuromuscular pathway is free from muscle relaxants prior to performing neurophysiology-based testing, such as bone integrity (e.g. pedicle) testing, nerve detection, and nerve retraction. This is described in greater detail within PCT Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The Basic Stimulated EMG Dynamic Stimulated EMG tests are designed to assess the integrity of bone (e.g. pedicle) during all aspects of pilot hole formation (e.g., via an awl), pilot hole preparation (e.g. via a tap), and screw introduction (during and after). These modes are described in greater detail in PCT Patent App. No. PCT/US02/35047 entitled "System and Methods for Performing Percutaneous Pedicle Integrity Assessments," filed on Oct. 30, 2002, and PCT Patent App. No. PCT/US2004/025550, entitled "System and Methods for Performing Dynamic Pedicle Integrity Assessments," filed on Aug. 5, 2004 the entire contents of which are both hereby incorporated by reference as if set forth fully herein. The XLIF mode is designed to detect the presence of nerves during the use of the various surgical access instruments of the system 10, including the pedicle access needle 26, k-wire 42, dilator 44, and retractor assembly 70. This mode is described in greater detail within PCT Patent App. No. PCT/US2002/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within PCT Patent App. No. PCT/US2002/30617, entitled "System and Methods for Performing Surgical Procedures and Assessments," filed on Sep. 25, 2002, the entire contents of which are hereby incorporated by reference as if set forth fully herein. The MEP Manual and Automatic modes are designed to test the motor pathway to detect potential damage to the spinal cord by stimulating the motor cortex in the brain and recording the resulting EMG response of various muscles in the upper and lower extremities. The MEP Manual and Automatic modes are described in greater detail within PCT Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein. The SSEP Manual and SSEP Automatic modes are designed to test the sensory pathway to detect potential damage to the spinal cord by stimulating peripheral nerves inferior to the target spinal level and recording the action potentials superior to the spinal level. The SSEP Manual and SSEP Automatic modes are described in greater detail within PCT Patent App. No. PCT/US2009/05650, entitled "Neurophysiologic Monitoring System and Related Methods," filed on Oct. 15, 2009, the entire contents of which is hereby incorporated by reference as if set forth fully herein. The surgical correction planning and assessment modes are described in greater detail within PCT Patent Application No. PCT/US2014/059974, entitled "Systems for Planning, Performing, and Assessing Spinal Correction during Spine Surgery", the entire contents of which is hereby incorporated by reference as if set forth fully herein. These functions will be explained now in brief detail.

Figure 23:
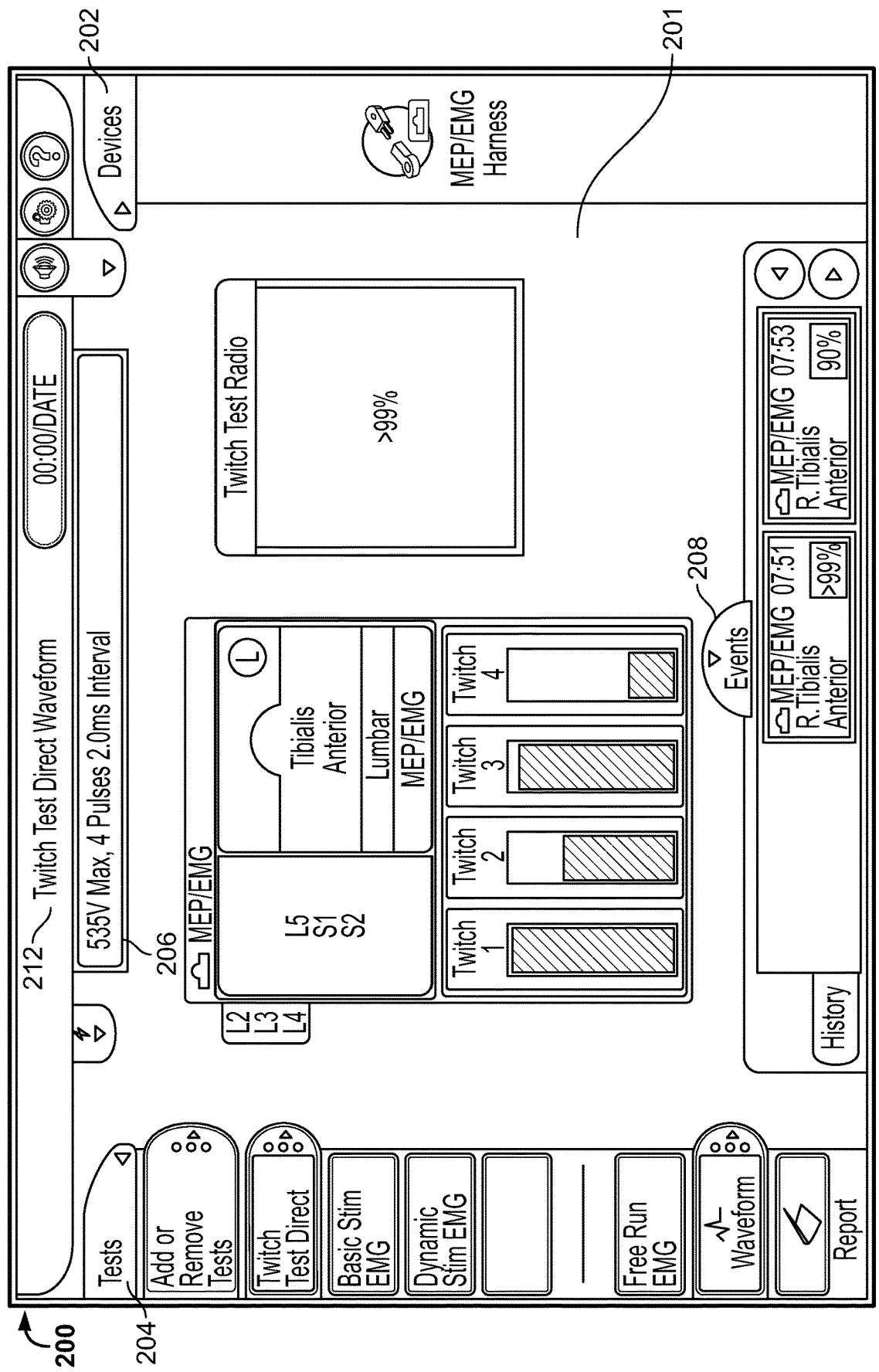
FIG. 23 is a screenshot of an example of a Twitch Test monitoring screen forming part of the system of FIG. 1.

The system 10 performs neuromuscular pathway (NMP) assessments, via Twitch Test mode, by electrically stimulating a peripheral nerve (preferably the Peroneal Nerve for lumbar and thoracolumbar applications and the Median Nerve for cervical applications) via stimulation electrodes 22 contained in the applicable electrode harness and placed on the skin over the nerve or by direct stimulation of a spinal nerve using a surgical accessory such as the probe 116. Evoked responses from the muscles innervated by the stimulated nerve are detected and recorded, the results of which are analyzed and a relationship between at least two responses or a stimulation signal and a response is identified. The identified relationship provides an indication of the current state of the NMP. The identified relationship may include, but is not necessarily limited to, one or more of magnitude ratios between multiple evoked responses and the presence or absence of an evoked response relative to a given stimulation signal or signals. With reference to FIG. 23, details of the test indicating the state of the NMP and the relative safety of continuing on with nerve testing are conveyed to the surgeon via GUI display 34. On the monitoring screen 200 utilized by the various functions performed by the system 10, function specific data is displayed in a center result area 201. The results may be shown as a numeric value 210, a highlighted label corresponding to the electrode labels 86, or (in the case of twitch test only) a bar graph of the stimulation results. On one side of center result area 201 is a collapsible device menu 202. The device menu displays a graphic representation of each device connected to the patient module 14. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure. Clicking on a particular event will open a note box and annotations may be entered and saved with the response for later inclusion in a procedure report. The event bar 208 also houses a chat box feature when the system 10 is connected to a remote monitoring system as described above. Within the result area 202 the twitch test specific results may be displayed.

It should be appreciated that while FIG. 23 depicts the monitoring screen 200 while the selected function is the Twitch Test, the features of monitoring screen 200 apply equally to all the functions. Result-specific data is displayed in a center result area 201. A large color saturated numeric value (not shown) is used to show the threshold result. Three different options are provided for showing the stimulation response level. First, the user can view the waveform. Second, a likeness of the color coded electrode harness label 86 may be shown on the display. Third, the color coded label 212 may be integrated with a body image. On one side of center result area 201 there is a collapsible device menu 202. The device menu displays a graphic representation of each device connected to the patient module 14. If a device is selected from the device menu 202, an impedance test may be initiated. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure so that the user may review the entire case history from the monitoring screen. Clicking on a particular event will open a note box and annotations may be entered and saved with the response for later inclusion in a procedure report chronicling all nerve monitoring functions conducted during the procedure as well as the results of nerve monitoring. In one embodiment the report may be printed immediately from one or more printers located in the operating room or copied to any of a variety of memory devices known in the prior art, such as, by way of example only, a floppy disk, and/or USB memory stick. The system 10 may generate either a full report or a summary report depending on the particular needs of the user. In one embodiment, the identifiers used to identify the surgical accessories to the patient module may also be encoded to identify their lot number or other identifying information. As soon as the accessory is identified, the lot number may be automatically added to the report. Alternatively, hand held scanners can be provided and linked to the control unit 12 or patient module 14. The accessory packaging may be scanned and again the information may go directly to the procedure report. The event bar 208 also houses a chat box feature when the system 10 is connected to a remote monitoring system to allow a user in the operating room to contemporaneously communicate with a person performing the associated neuromonitoring in a remote location.

The system 10 may also conduct free-run EMG monitoring while the system is in any of the modes described herein. Free-run EMG monitoring continuously listens for spontaneous muscle activity that might be indicative of potential danger. The system 10 may automatically cycle into free-run monitoring after 5 seconds of inactivity. Initiating a stimulation signal in the selected mode will interrupt the free-run monitoring until the system 10 has again been inactive for five seconds, at which time the free-run begins again.

The system 10 may test the integrity of pedicle holes (during and/or after formation) and/or screws (during and/or after introduction) via the Basic Stimulation EMG and Dynamic Stimulation EMG tests. To perform the Basic Stimulation EMG a test probe 116 is placed in the screw hole prior to screw insertion or placed on the installed screw head and a stimulation signal is applied. The insulating character of bone will prevent the stimulation current, up to a certain amplitude, from communicating with the nerve, thus resulting in a relatively high $I_{thresh}$, as determined via the basic threshold hunting algorithm described below. However, in the event the pedicle wall has been breached by the screw or tap, the current density in the breach area will increase to the point that the stimulation current will pass through to the adjacent nerve roots and they will depolarize at a lower stimulation current, thus $I_{thresh}$ will be relatively low. The system described herein may exploit this knowledge to inform the practitioner of the current $I_{thresh}$ of the tested screw to determine if the pilot hole or screw has breached the pedicle wall.

In Dynamic Stim EMG mode, test probe 116 may be replaced with a clip 18 which may be utilized to couple a surgical tool, such as for example, a tap member 28 or a pedicle access needle 26, to the system 10. In this manner, a stimulation signal may be passed through the surgical tool and pedicle integrity testing can be performed while the tool is in use. Thus, testing may be performed during pilot hole formation by coupling the access needle 26 to the system 10, and during pilot hole preparation by coupling the tap 28 to the system 10. Likewise, by coupling a pedicle screw to the system 10 (such as via pedicle screw instrumentation), integrity testing may be performed during screw introduction.

In both Basic Stimulation EMG mode and Dynamic Stimulation EMG mode, the signal characteristics used for testing in the lumbar testing may not be effective when monitoring in the thoracic and/or cervical levels because of the proximity of the spinal cord to thoracic and cervical pedicles. Whereas a breach formed in a pedicle of the lumbar spine results in stimulation being applied to a nerve root, a breach in a thoracic or cervical pedicle may result in stimulation of the spinal cord instead, but the spinal cord may not respond to a stimulation signal the same way the nerve root would. To account for this, the surgical system 10 is equipped to deliver stimulation signals having different characteristics based on the region selected. By way of example only, when the lumbar region is selected, stimulation signals for the stimulated EMG modes comprise single pulse signals. On the other hand, when the thoracic and cervical regions are selected the stimulation signals may be configured as multipulse signals.

Figure 24:
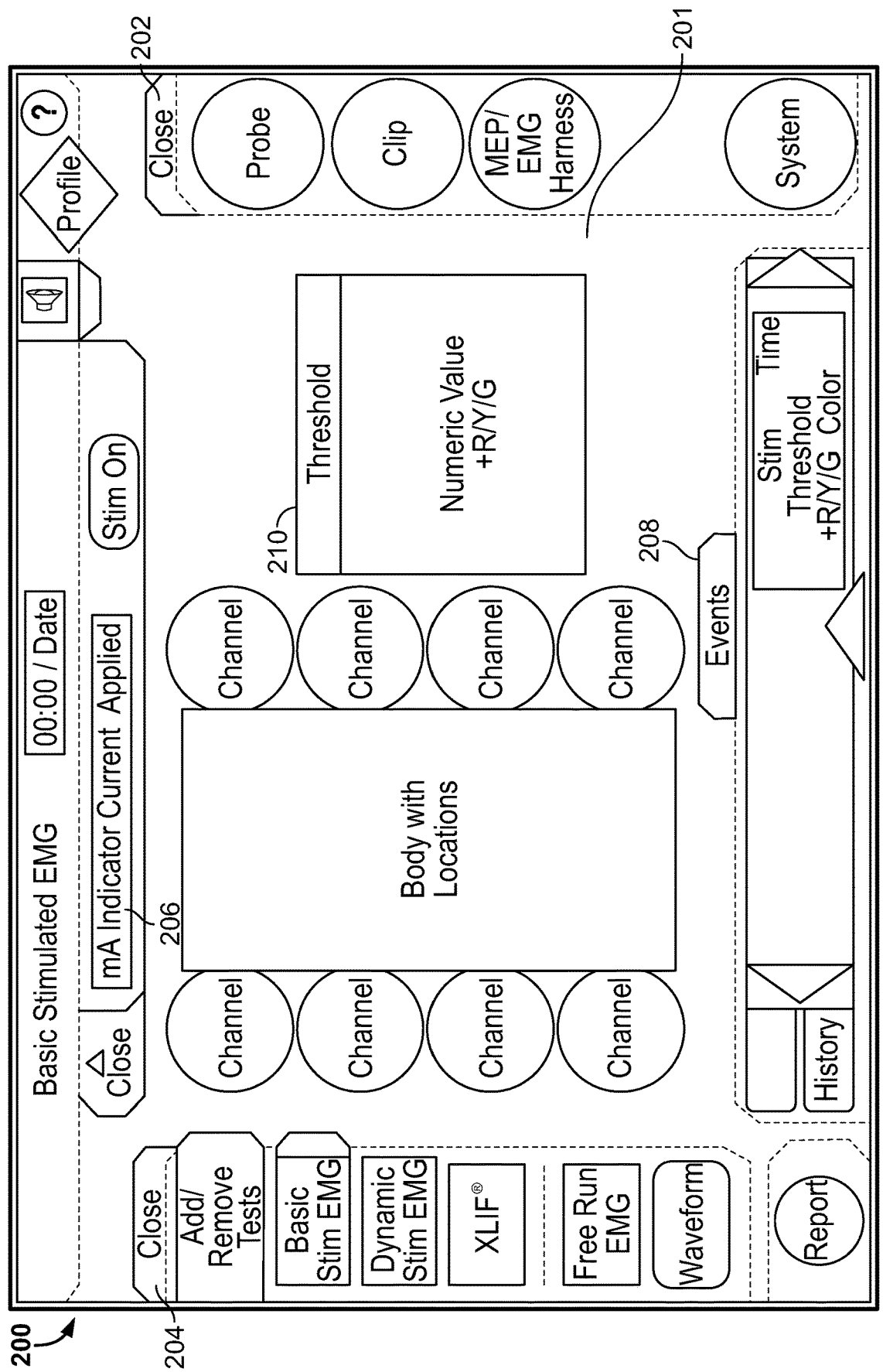
FIG. 24 is a screenshot of an example embodiment of a Basic Stimulation EMG monitoring screen forming part of the system of FIG. 1.
Figure 25:
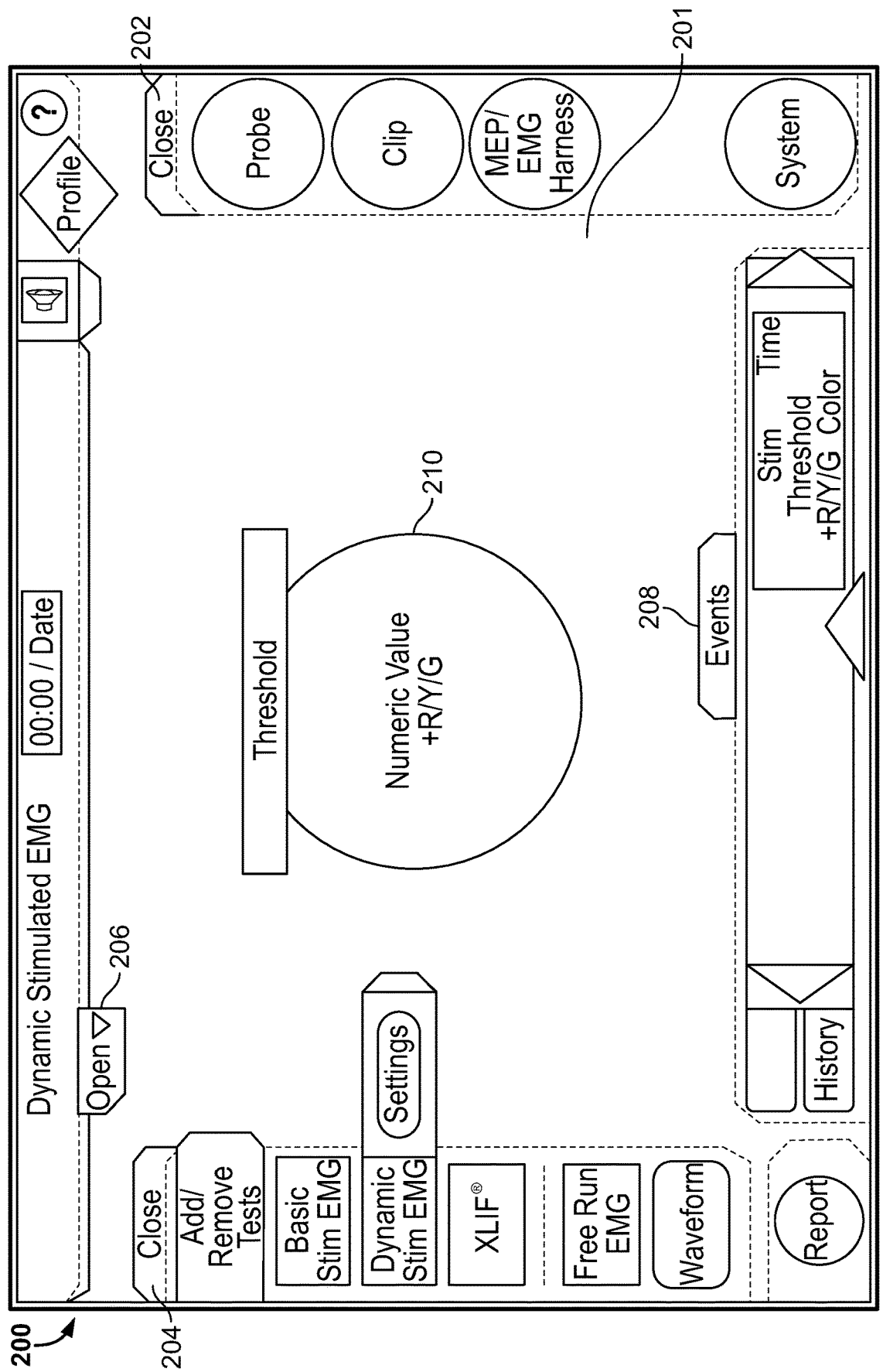
FIG. 25 is a screenshot of an example embodiment of a Dynamic Stimulation EMG monitoring screen forming part of the system of FIG. 1.

Stimulation results (including but not necessarily limited to at least one of the numerical $I_{thresh}$ value and color coded safety level indication) and other relevant data are conveyed to the user on at least main display 34, as illustrated in FIGS. 24 and 25. FIG. 24 illustrates the monitoring screen 200 with the Basic Stimulation EMG test selected. FIG. 25 illustrates the monitoring screen 200 with the Dynamic Stimulation EMG test selected. In one embodiment of the various screw test functions (e.g. Basic and Dynamic), green corresponds to a threshold range of greater than 10 milliamps (mA), a yellow corresponds to a stimulation threshold range of 7-10 mA, and a red corresponds to a stimulation threshold range of 6 mA or below. EMG channel tabs may be selected via the touch screen display 26 to show the $I_{thresh}$ of the corresponding nerves. Additionally, the EMG channel possessing the lowest $I_{thresh}$ may be automatically highlighted and/or colored to clearly indicate this fact to the user.

Figure 26:
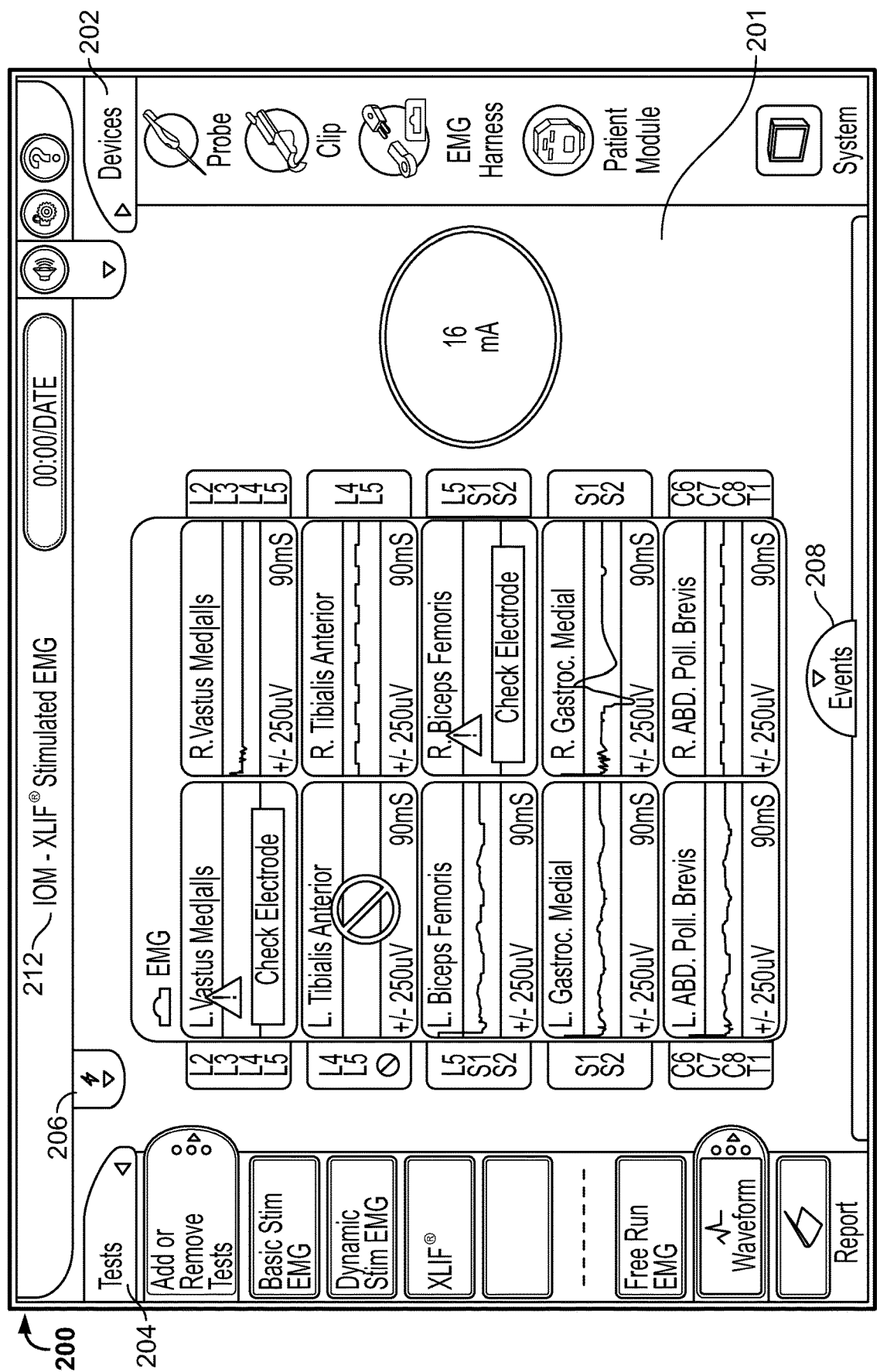
FIG. 26 is a screenshot of an example embodiment of a Nerve Surveillance EMG monitoring screen forming part of the system of FIG. 1.

The system 10 may perform nerve proximity testing, via the XLIF mode, to ensure safe and reproducible access to surgical target sites. Using the surgical access components 26-32, the system 10 detects the existence of neural structures before, during, and after the establishment of an operative corridor through (or near) any of a variety of tissues having such neural structures which, if contacted or impinged, may otherwise result in neural impairment for the patient. The surgical access components 26-32 are designed to bluntly dissect the tissue between the patient's skin and the surgical target site. Dilators of increasing diameter, which are equipped with one or more stimulating electrodes, are advanced towards the target site until a sufficient operating corridor is established to advance retractor 32 to the target site. As the dilators are advanced to the target site electrical stimulation signals are emitted via the stimulation electrodes. The stimulation signal will stimulate nerves in close proximity to the stimulation electrode and the corresponding EMG response is monitored. As a nerve gets closer to the stimulation electrode, the stimulation current required to evoke a muscle response decreases because the resistance caused by human tissue will decrease, and it will take less current to cause nervous tissue to depolarize. $I_{thresh}$ is calculated, using the basic threshold hunting algorithm described below, providing a measure of the communication between the stimulation signal and the nerve and thus giving a relative indication of the proximity between access components and nerves. An example of the monitoring screen 200 with XLIF mode active is depicted in FIG. 26. In a preferred embodiment, a green or safe level corresponds to a stimulation threshold range of 10 milliamps (mA) or greater, a yellow level denotes a stimulation threshold range of 5-9 mA, and a red level denotes a stimulation threshold range of 4 mA or below.

Figure 27:
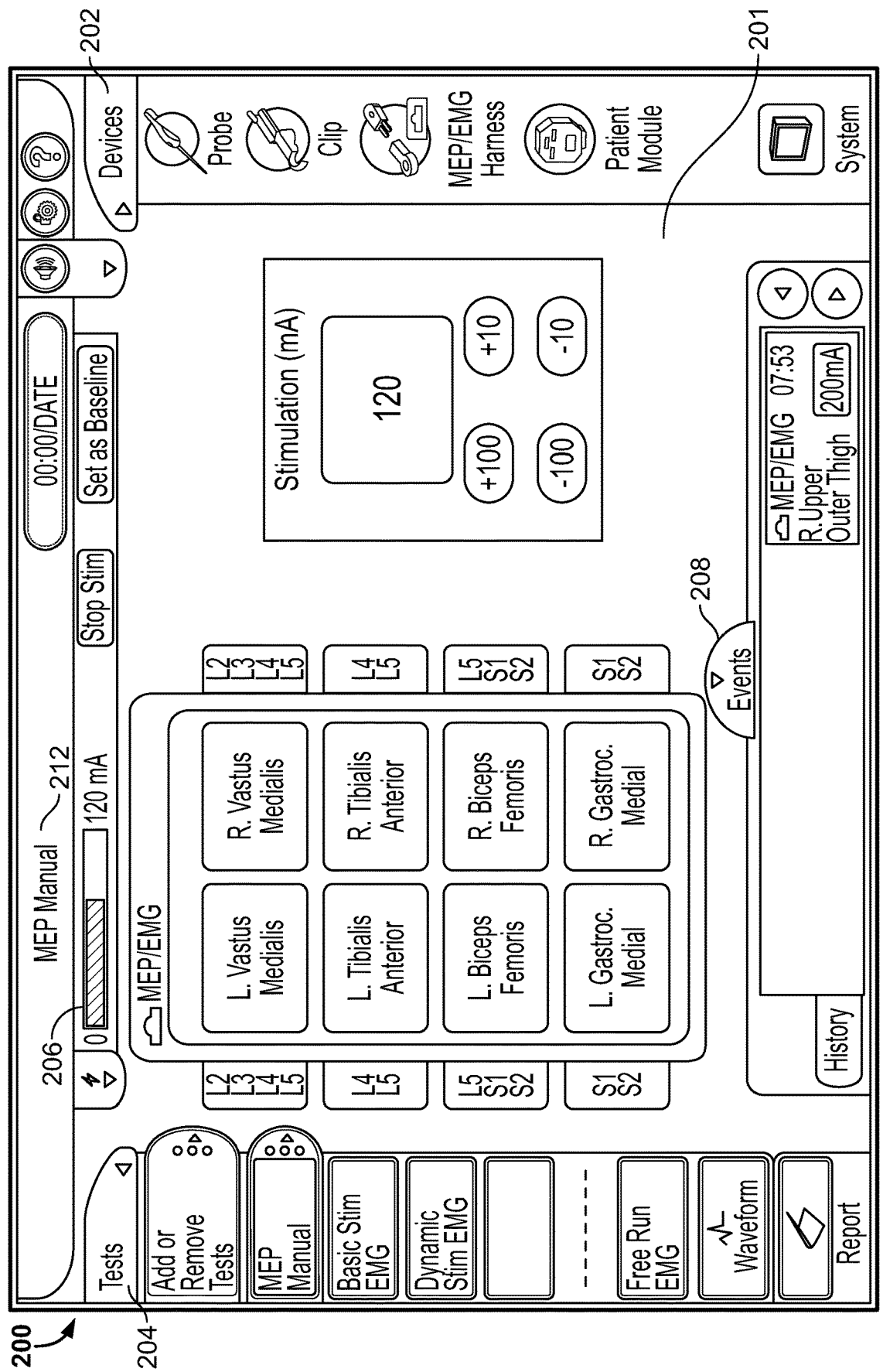
FIG. 27 is a screenshot of an example embodiment of a Manual MEP monitoring screen forming part of the system of FIG. 1.
Figure 28:
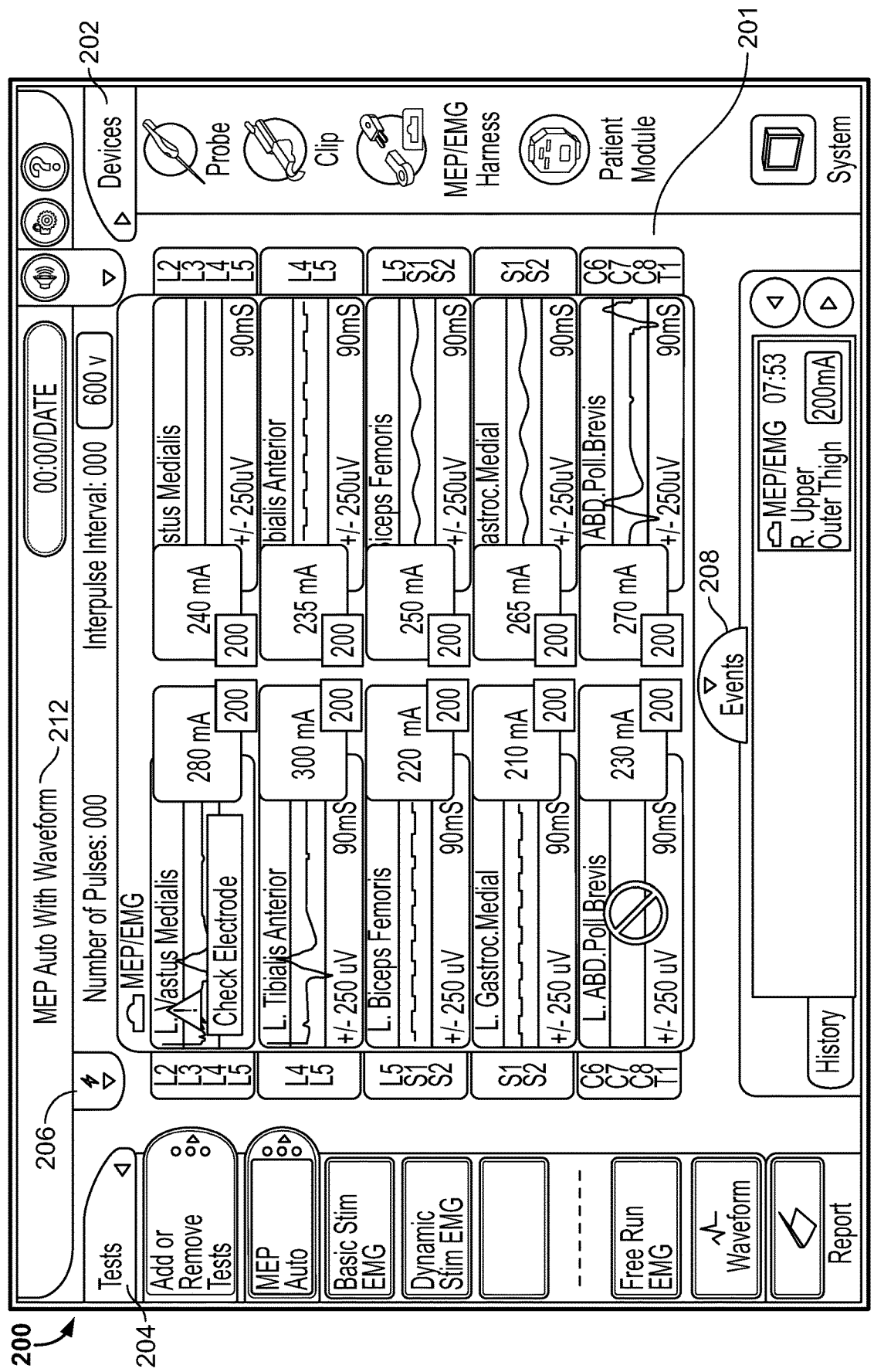
FIG. 28 is a screenshot of an example embodiment of an Automatic MEP monitoring screen forming part of the system of FIG. 1.

In MEP modes, stimulation signals are delivered to the motor cortex via patient module 14 and resulting responses are detected from various muscles in the upper and lower extremities. An increase in $I_{thresh}$ from an earlier test to a later test may indicate a degradation of spinal cord function. Likewise, the absence of a significant EMG response to a given $I_{stim}$ on a channel that had previously reported a significant response to the same or lesser $I_{stim}$ is also indicative of a degradation in spinal cord function. These indicators are detected by the system in the MEP modes and reported to the surgeon. In MEP Manual mode, the user selects the stimulation current level and the system reports whether or not the stimulation signal evokes a significant response on each channel. Stimulation results may be shown on the display 34 in the form of "YES" and "NO" responses, or other equivalent indicia, as depicted in FIG. 27. In MEP Automatic mode the system determines the $I_{thresh}$ baseline for each channel corresponding to the various monitored muscles, preferably early in the procedure, using the multichannel algorithm described. Throughout the procedure subsequent tests may be conducted to again determine $I_{thresh}$ for each channel. The difference between the resulting $I_{thresh}$ values and the corresponding baseline are computed by the system 10 and compared against predetermined "safe" and "unsafe" difference values. The $I_{thresh}$, baseline and difference values are displayed to the user, along with any other indicia of the safety level determined (such as a red, yellow, green color code), on the display 34, as illustrated in FIG. 28. Using either mode the surgeon may thus be alerted to potential complications with the spinal cord and any corrective actions deemed necessary may be undertaken at the discretion of the surgeon.

In Transcutaneous Nerve Root Stimulation modes, the system 10 is capable of ascertaining the health and/or status of at-risk nerves along the motor neural pathway superior and inferior to the surgical site before, during, and/or after the creation of the operative corridor to the surgical target site. To accomplish this, stimulation electrodes 22 may be placed on the skin over the desired spinal nerve roots (such as by way of example only, the L1 and L2 nerve roots and/or the location of the conus medullaris of the patient) and recording electrodes 24 are positioned on the recording sites (such as, by way of example only, the recording sites set forth above in Table 5). The control unit 12 and patient module 14 cooperate to transmit electrical stimulation signals to a stimulating cathode placed posteriorly on the patient's back. These stimulation signals cause nerves deep to the stimulating electrode to depolarize, evoking activity from muscles innervated by the nerves below. The system 10 detects and records the neuromuscular responses and optionally analyzes their relationship to the stimulation signal (discussed below). Resulting recording and/or assessment data is conveyed to the user on screen 200 and/or activator 330 as discussed herein. The TCNR testing described herein provides the ability to verify that the patient is positioned in a neutral way and that no neural structures have been impinged upon after the operative corridor has been established. In spinal surgery, for example, this is particularly advantageous in that the system 10 may be particularly suited for establishing an operative corridor to an intervertebral target site in a posterolateral, trans-psoas fashion so as to avoid the bony posterior elements of the spinal column.

In one implementation, a stimulating cathode is placed posteriorly and an anode is placed anteriorly at locations superior to the surgical target site and neuromuscular responses (transcutaneous nerve root "TCNR" responses) are evoked in response to transcutaneous, trans-abdominal motor pathway stimulation. By way of example only, the stimulating cathode may be a single cathode adhesive surface electrode placed over the conus medullaris at spinal level L1-2, preferably with the electrode pair oriented side to side and symmetrically over the neural foramen. The anode electrode may be an adhesive surface electrode placed at the anterior abdominal midline below the umbilicus, preferably with the electrode pair oriented side to side, symmetrically across the midline. Implementing a stimulation montage in this way is beneficial for at least two reasons. First, stimulating trans-abdominally does not evoke muscle twitching of the head, upper extremities, or upper torso which leads to less patient movement than transcranial MEP testing. Second, using a surface electrode with a larger surface electrode anteriorly and a smaller surface electrode posteriorly may decrease the current density travelling trans-abdominally, reducing the depolarization of the abdominal muscles and thus, further decreasing the amount of patient movement. Third, stimulating nerve roots with the TCNR techniques described herein can activate the specific area of the motor neural pathway of interest and elicit significant neuromuscular responses with a fixed polarity, single pulse stimulation whereas MEP testing requires multi-pulse trains of stimuli (oftentimes dual polarity stimulation as well) to activate the motor cortex and the entire corticospinal pathway to elicit clinically significant neuromuscular responses. This leads to greater specificity, less patient movement, and less power delivered to the patient. Recording electrodes may be placed on or in muscles innervated by one or more nerves of the lumbar plexus. The electrode harness 80 may be designed such that the various electrodes may be positioned about the patient as described in Table 5.

The steps of performing transcutaneous, trans-abdominal stimulation and recording the resultant evoked potentials is preferably first performed prior to establishing the lateral access corridor and subsequently performed periodically during the surgical procedure. In this way, the system 10 is capable of detecting changes to the stimulation threshold intensities of these nerves over time which may be indicative of changes to the health/status of these nerves (e.g. by compression or patient positioning). According to one embodiment, the system 10 may perform TCNR in either of two modes: Alert mode and Threshold mode. In Alert mode, the system 10 evaluates the neuromuscular responses for the presence/absence of a response. In Threshold mode, the system 10 detects changes to the stimulus intensity required to elicit a significant response. By way of example only, a change in the health or status of a nerve may be deemed significant once the stimulus intensity required to elicit a neuromuscular response from a muscle exceeds pre-determined criteria (e.g. 200 A greater than the baseline stimulation threshold). The system 10 may quickly and accurately determine this data and convey the useful information in a simple and easily comprehensible manner for interpretation by a surgeon, neurophysiologist, or other medical personnel. It is contemplated that the control unit 12 of the system 10 may automatically ascertain this information and/or communicate any of numerical, graphic, audio, and visual feedback corresponding to one or more of these findings. Armed with this useful information, the surgeon may detect a problem or potential problem early and then act to avoid and/or mitigate the problem.

Figure 29:
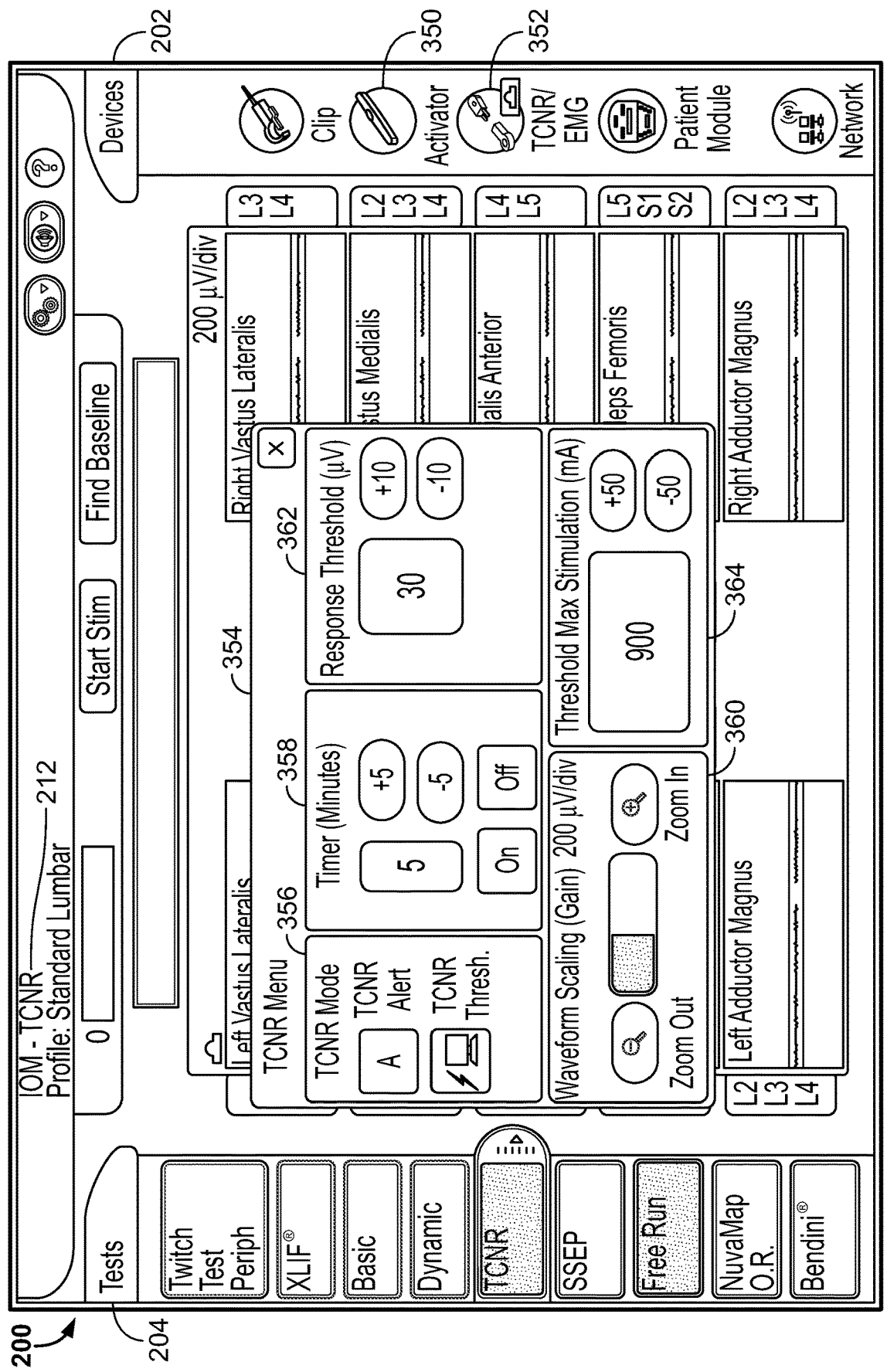
FIG. 29 is a screenshot of an example embodiment of a TCNR setup screen forming part of the system of FIG. 1.

FIGS. 29-34 are example screen displays of the TCNR mode according to one embodiment of the system 10. FIG. 29 illustrates an intraoperative monitoring (IOM) setup screen from which various features and parameters of the TCNR mode may be controlled and/or adjusted by the user as desired. It is contemplated that there are any number of ways that the TCNR mode and TCNR testing may be activated by the user. For example, the user may select the TCNR mode from the test selection tab 204. The user may plug the activator 330 into accessory port 133 as described above. The user may press stimulation button 340 on activator 330 which will automatically toggle the system 10 from the mode it was performing prior to TCNR mode selection to TCNR mode (e.g. XLIF mode). According to some implementations, pressing stimulation button 340 in this manner 340 not only toggles the system 10 to TCNR mode, but also immediately initiates a TCNR stimulation test as well giving the user rapid flexibility in assessing the health and status of various aspects of the lower motor neural pathway. As shown in FIG. 29, the devices tab 202 indicates to the user an activator icon 350 and a TCNR/EMG icon 350 indicating that the activator 330 and TCNR/EMG harness 80 are properly connected to the system 10.

Selecting the TCNR button from the test selection tab 204 brings up a TCNR Menu window 354. The user may toggle between Alert mode and Threshold mode in TCNR Mode field 356, and change one or more profile settings (e.g. timer, waveform scaling, response threshold maximum stimulation). As will be explained in detail below, in some implementations, a user may wish to know when a predetermined period of time has elapsed between TCNR stimulations. According to one or more embodiments, there is provided a timer to address such a need. The timer setting may be adjusted in timer field 358. The timer may be turned on or off and the time may be selected from a range between 0 and 30 minutes, with a default value of 5 minutes. The timer setting may be increased or decreased in increments of 5 minutes using the timer selection buttons labeled (by way of example only) "+5" and "−5". Waveform scaling may be accomplished by increasing or decreasing the gain by using the buttons labeled (by way of example only) "Zoom In" and "Zoom Out" in waveform scaling field 360. According to one example, the gain has a range of 10 µV and 10,000 µV with a default gain setting is 200 µV. Each adjustment increases or decreases the gain by a fixed increment (e.g. 10 µV). The minimum threshold setting for which a given response qualifies as a response may be displayed and adjusted in response threshold field 362. The selected response threshold setting may be increased or decreased in increments of 10 µV using the buttons labeled "+10" and "−10". According to one example, the threshold setting may be selected from a range of 10 µV to 300 µV with a default value of 30 µV. The maximum stimulation intensity that may be delivered in TCNR Threshold mode may also be selected in Threshold maximum stimulation field 364. According to one example, the maximum threshold may be selected from a range between 50 mA and 1500 mA with a starting value of 100 mA. The threshold setting may be increased or decreased in increments of 50 A using buttons labeled (by way of example only) "+50" and "−50". As shown by way of example in FIG. 29, the maximum threshold is shown at 900 mA, that is to say the maximum threshold that may be delivered to the patient is 900 mA.

Figure 30:
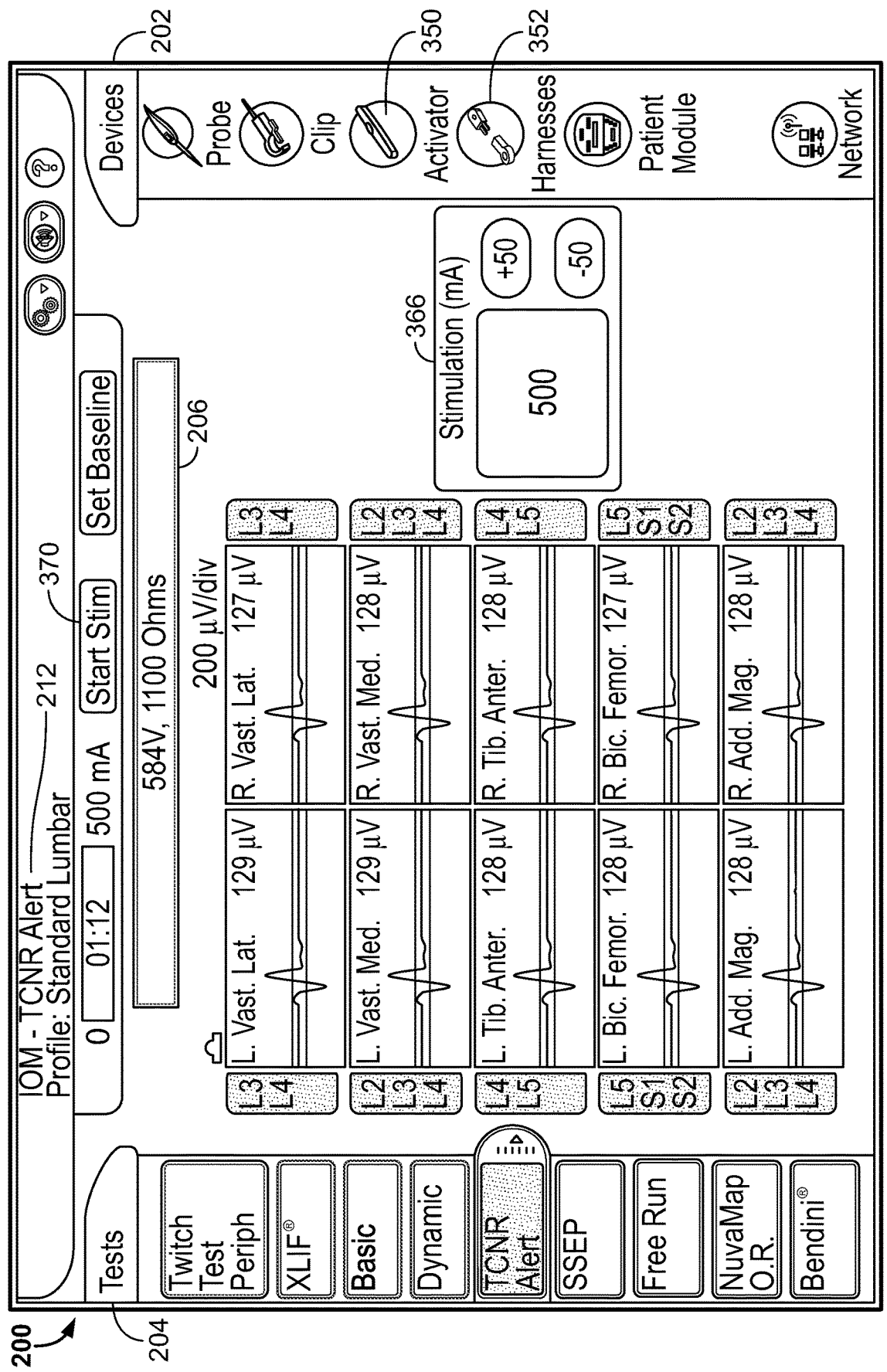
FIG. 30 is a first screenshot of an example embodiment of a TCNR Alert monitoring screen forming part of the system of FIG. 1.
Figure 31:
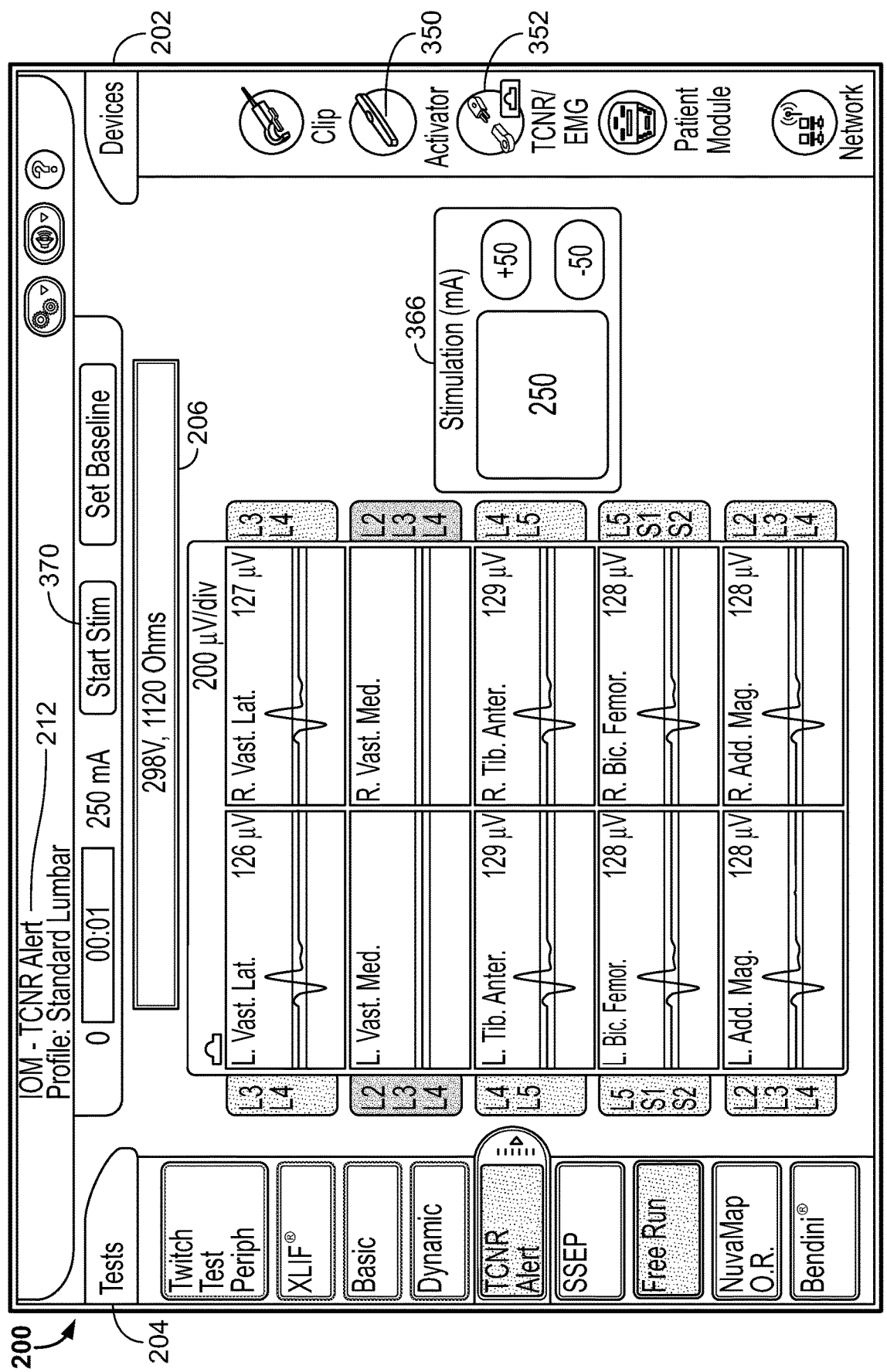
FIG. 31 is a second screenshot of the TCNR Alert monitoring screen of FIG. 30.

FIGS. 30-31 depict example screen displays for the Alert mode of the TCNR monitoring function. These screen displays are intended to communicate information to the surgeon or other personnel in an easy-to-interpret fashion. This information may include, but is not necessarily limited to, a display of the test mode 212, channels 10 for each myotome [indicating]: spinal levels monitored (e.g. L. Add. Mag.); waveforms of the evoked responses, voltages of the evoked responses; a stimulation bar 206 to display particulars of the stimulation (e.g. stimulation parameters, the stimulation intensity required to elicit a response, and the stimulation intensity required to elicit a response. This information may be communicated in any number of suitable fashions, including but not limited to, the use of visual indicia (such as alpha-numeric characters, light-emitting elements, and/or graphics) and audio communication (such as a speaker element).

In TCNR Alert mode, the underlying neurophysiologic principle of operation is to assess the health and status of the lower motor neural pathway via the presence/absence of evoked neuromuscular responses for each muscle monitored. To perform TCNR monitoring in Alert mode, the user first manually selects the stimulation intensity to be delivered to the stimulation electrodes. The stimulation intensity that may be delivered in TCNR Alert mode may also be selected in Alert stimulation field 366. According to one example, the simulation intensity may be selected from a range between 50 mA and 1500 mA with a starting value of 100 mA. The setting may be increased or decreased in increments of 50 mA with a starting value of 100 mA. The setting may be increased or decreased in increments of 50 mA using buttons labeled (by way of example only) "+50" and "−50". As shown by way of example in FIG. 30, the stimulation intensity to be delivered is 500 mA.

According to one or more implementations, for a given stimulation intensity (mA) the presence of a significant EMG response for a particular muscle is presented to the user via a green color indicator and the absence of a significant EMG response for a particular muscle is presented to the user via a red color indicator. As shown in FIG. 30, responses were obtained in all 10 channels for all muscles with 500 mA stimulation. As such, a green color indicator is shown in each channel 110. Referring now to FIG. 31, responses were obtained in all channels except the left and right vastus medialis channels with 250 mA stimulation. As such, red color indicators are shown in the left and right vastus medialis channels and green color indicators are shown in the remaining channels in which a significant response was recorded. According to some embodiments, the system 10 provides visual and audible alerts when the responses are absent. By way of example, the system 10 may flash a warning on screen 200, or an audible tone.

In TCNR Alert mode, periodic testing for the presence/absence of TCNR responses are made to monitor the health and status of the lower motor neural pathways. As indicated above, a user may which to know when a predetermined period of time has elapsed between TCNR tests. Armed with such information, the user may perform another TCNR test or wait until a later time in the surgical procedure to do so. The timer interval may be set as described above. After each TCNR test, the system 10 will initiate a timer corresponding to the selected time interval and, when the time has elapsed, the system 10 will activate a reminder alert. The reminder alert may include, by way of example only, any one of, or combination of, an audible tone, voice recording, screen flash, pop up window, scrolling message, or any other such alert to remind the user to perform a TCNR test again. The alerts may be displayed on screen 200 (for example, in the stimulation bar), on the activator (for example via LED indicator 342), or both screen 200 and activator 330 simultaneously.

For optimal consistency of TCNR testing and the information it provides, the TCNR stimulations are preferably conducted at a set time interval throughout the surgical procedure (e.g., every 5 minutes). According to one embodiment, after 5 minutes have elapsed, the LED indicator 342 and/or the on-screen stimulator bar 206 blinks green at a 1 Hz rate. The user may decide to perform another TCNR test either by pressing button 340 or "Start Stim" button 370 or the user may decide to wait until a later time in the surgical procedure. After 10 minutes have elapsed, LED indicator 342 (and/or the on-screen stimulator bar 206) continues to blink green but at a 2 Hz rate. When the user decides to stimulate, he/she presses the activator stimulator button 340 or the "Start Stim" button 370 to run the TCNR test and the timer function restarts. While described herein with respect to the TCNR Alert mode, it is contemplated that the timer function may be implemented in TCNR Threshold mode as well.

Figure 32:
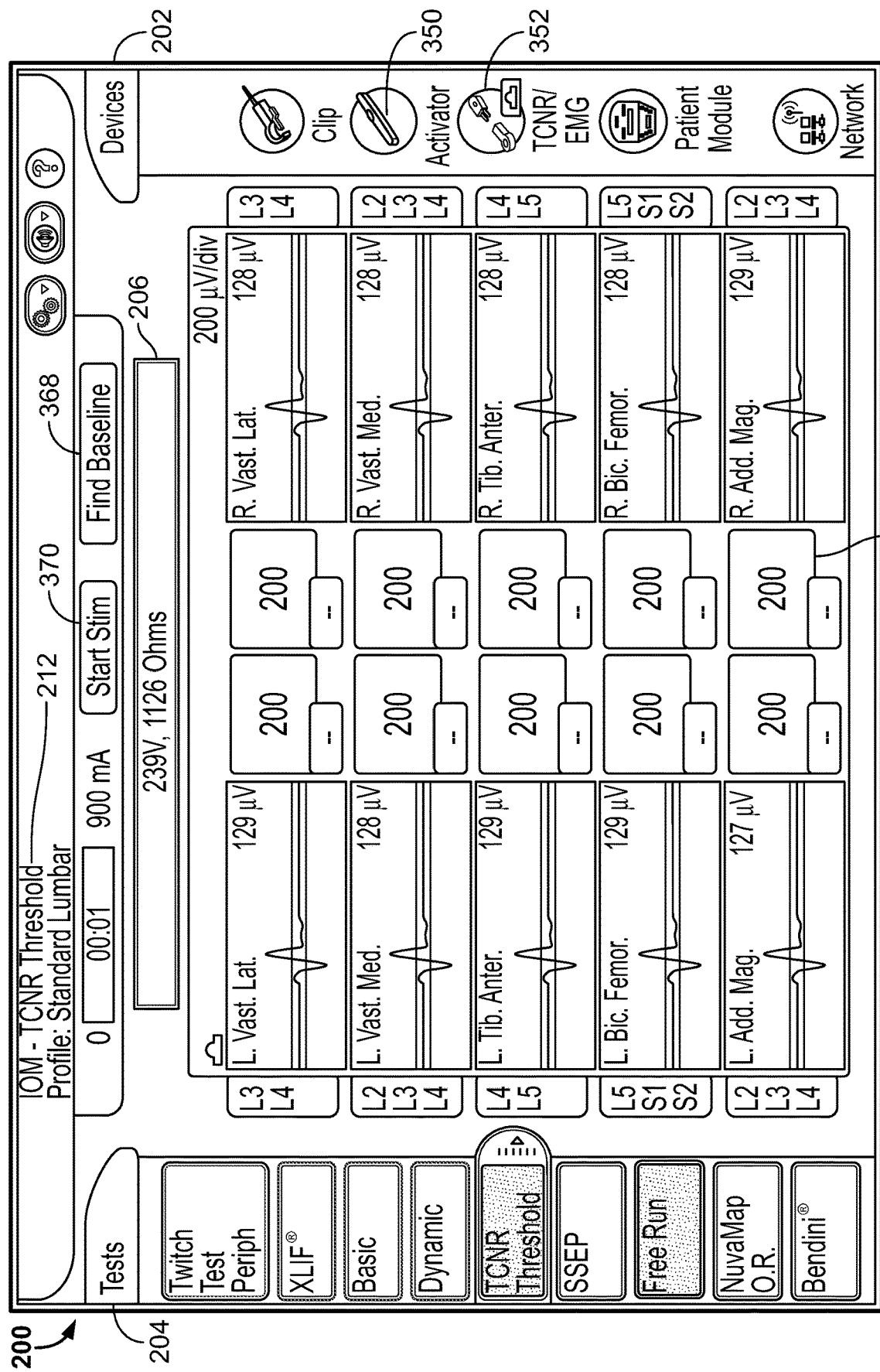
FIG. 32 is a first screenshot of an example embodiment of a TCNR Threshold monitoring screen forming part of the system of FIG. 1.
Figure 33:
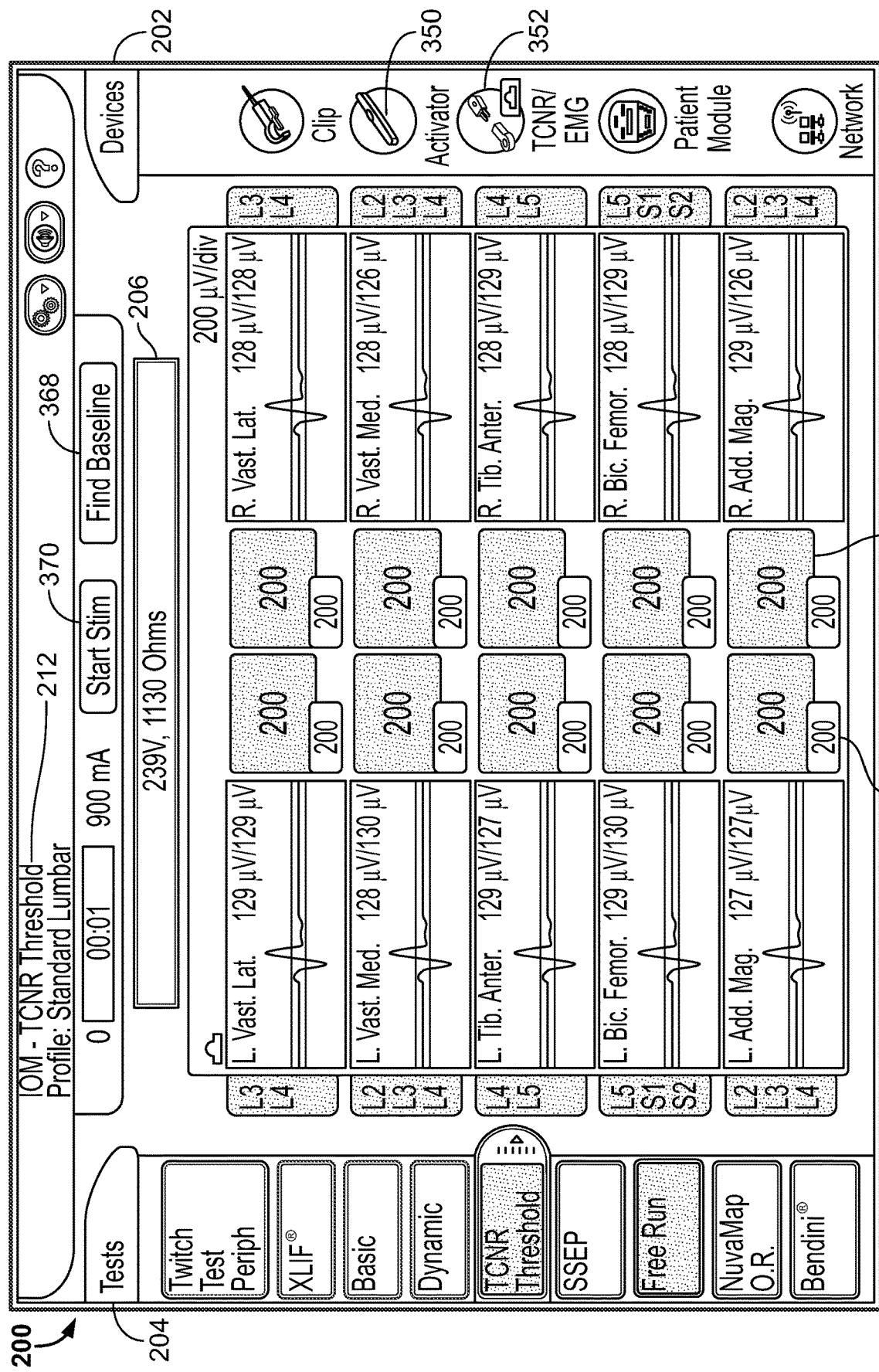
FIG. 33 is a second screenshot of the TCNR Threshold monitoring screen of FIG. 32.
Figure 34:
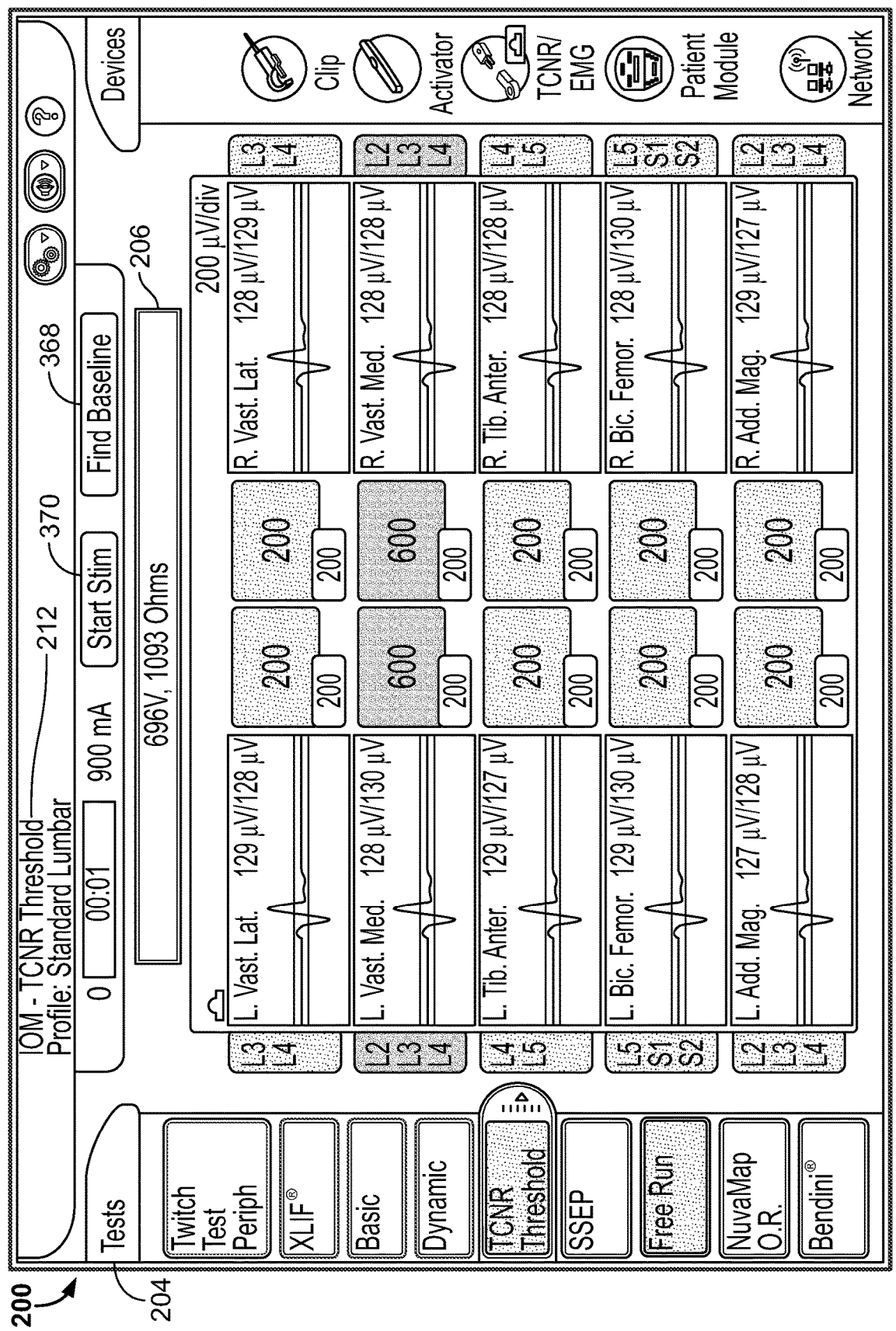
FIG. 34 is a third screenshot of the TCNR Threshold monitoring screen of FIG. 32.

FIGS. 32-34 depict example screen displays for the Threshold mode of the TCNR monitoring function. In TCNR Threshold mode, the underlying neurophysiologic principle is that, in order to monitor the health of the lumbar motor neural pathway, the user must be able to determine if the evoked responses are changing with respect to the stimulation signal. To monitor for this change, baseline TCNR responses are established for all muscles of interest (preferably prior to surgical manipulation) and then compared to subsequent TCNR responses periodically throughout the procedure.

The baseline feature of the TCNR Threshold mode will now be described with respect to FIG. 32. Selecting the "Find Baseline" button 368 on the screen 200 or pressing the stimulation button 340 on the activator 330 starts the baseline stimulation sequence. The system 10 then delivers one or more stimulation pulses and/or trains of pulses until a baseline TCNR response is evoked in one or all muscle channels. By way of example only, the system 10 may be configured to determine the stimulus response threshold ($I_{thresh}$) via one or more of the threshold hunting and thresholding algorithms described below. FIG. 32 depicts an example set of responses in which baseline TCNR responses and baseline response thresholds ($I_{Thresh-Base}$) were found in all 10 muscle channels (shown for each channel as 200 mA in results field 372). According to some embodiments, baseline TCNR response waveforms remain in the waveform windows for comparison to subsequent stimulation trials. This allows for more detailed comparison of the response waveform amplitudes and morphologies. The peak to peak amplitude measurements (in microvolts) of both the baseline and subsequent results are displayed in the waveform window. In some implementations, the baseline waveforms and subsequent waveforms bay be indicated differently, by way of example the baseline waveform may be depicted as purple and the current waveform may be depicted as white.

In the event the system detects a significant increase in the amount of stimulus intensity required to elicit a neuromuscular response ($I_{Thresh}$), or if no neuromuscular response is obtained at the maximum stimulus intensity permitted, the associated window may preferably be highlighted with a predetermined color (e.g. red) to indicate the potential danger to the surgeon. Preferably, the stimulation results are displayed to the surgeon along with a color code so that he/she may easily comprehend the danger, diagnose, and take corrective measures to avoid or mitigate such danger. This may, for example, more readily permit TCNR monitoring results to be interpreted by the surgeon or assistant without necessarily requiring dedicated monitoring personnel. By way of example only, red is used when the increase in threshold stimulus intensity is within a predetermined safe level. Yellow is used when the increase in threshold stimulus intensity is between the predetermined safe and unsafe levels. By way of example only, the system 10 may also notify the user of potential danger through the use of a warning which may be communicated to the user by any one of, or combination of, a pop-up window, an audible tone, voice recording, screen flash, scrolling message, or any other such alert to notify the user of potential danger. According to one embodiment, the system 10 may notify the user according to the following scenario:

TABLE 9

| Change in $I_{Thresh}$ from Baseline | Color | Audio Feedback | Neurophysiologic Assessment |
|---|---|---|---|
| 0-100 mA | Green | Slow, Low Pitch | No significant change from baseline |
| >100 mA to <200 mA | Yellow | Faster, Higher Pitch | Noteworthy change from baseline |
| 200 mA or more | Red | Fastest, Highest Pitch | Significant change from baseline |

FIGS. 33-34 depict example TCNR responses obtained subsequent to the baseline TCNR responses of FIG. 32. The baseline $I_{thresh}$ response results move from results field 372 to baseline field 374. As shown in FIG. 33, responses in a subsequent test were obtained in all channels 110 with 200 mA stimulation ($I_{thresh-subsequent}$), indicating no significant changes in neurophysiologic recordings from baseline. These results are displayed in results field 372. As such, green color indicators shown for each of these channels in accordance with the embodiment shown and described above in Table 9. Referring now to FIG. 34, responses in another subsequent trial were obtained in all channels, 200 mA of stimulation intensity was required to elicit a significant neuromuscular response in the bilateral vastus lateralis, tibialis anterior, biceps femoris, and adductor magnus channels indicating no significant changes in neurophysiologic recordings from baseline. Green color indicators are shown for each channel. However, 600 mA of stimulation intensity was required to elicit a significant neuromuscular response in the bilateral vastus medialis channels which is a 400 mA increase from the baseline requirement of 200 mA. Red color indicators are shown for each of these channels. It is to be appreciated that the predetermined safety levels, colors, audio feedback, and neurophysiologic interpretation set forth above are merely for illustrative purposes only and are not meant to be limiting in any way.

In some surgical procedures, it may be advantageous to perform more than one type of neurophysiologic testing during a surgical procedure. Oftentimes, it is advantageous to perform multiple types of neurophysiologic testing and monitoring modes intermittently during a procedure. Constantly switching between modes and initiating/re-initiating testing in each mode can be cumbersome, time-consuming, and frustrating for users. They may become impatient with the system 10. In accordance with the present invention, the system 10 includes functionality to toggle or switch between two or more neurophysiologic monitoring modes quickly and seamlessly as will be discussed below.

For illustrative purposes only, in a minimally-invasive lateral approach spine procedure (e.g., XLIF®), it may be desirable to perform both nerve proximity testing and transcutaneous nerve root testing intermittently, but at different times from one another throughout the surgical procedure. The control unit 12 possesses the requisite functionality to toggle or switch between XLIF and TCNR modes as directed by the user. In some embodiments, the toggling or switching is effectuated by the stimulation clip 18/activator 330 assembly described above. According to some implementations, if the user has selected XLIF mode, the system 10 will stay in XLIF mode until an indication from the user. This indication may be pressing the stimulation button 340 on the activator 330. Pressing the stimulation button 340 one time will simultaneously toggle to the appropriate TCNR mode screen and perform a stimulation trial in TCNR mode. To toggle or switch back to XLIF mode, the user may press activation button 131 on button module 129 to simultaneously toggle to the XLIF mode screen and perform a stimulation trial in XLIF mode or, if a stimulation trial in XLIF mode is not desired at that time, the user can do nothing. The TCNR screen may time out (for example, 1 minute after the last TCNR stimulation trial) and the system 10 will toggle or switch back to the XLIF mode screen 200. However, the TCNR timer function will still be active and will remind the user to perform another stimulation when the timer has lapsed as set forth above. Thus, according to such embodiments, the user is able to perform more than one neurophysiologic monitoring modes intermittently without having to does not need to make/or instruct hospital personnel to make changes on the screen 200 to switch between modes.

Figure 35:
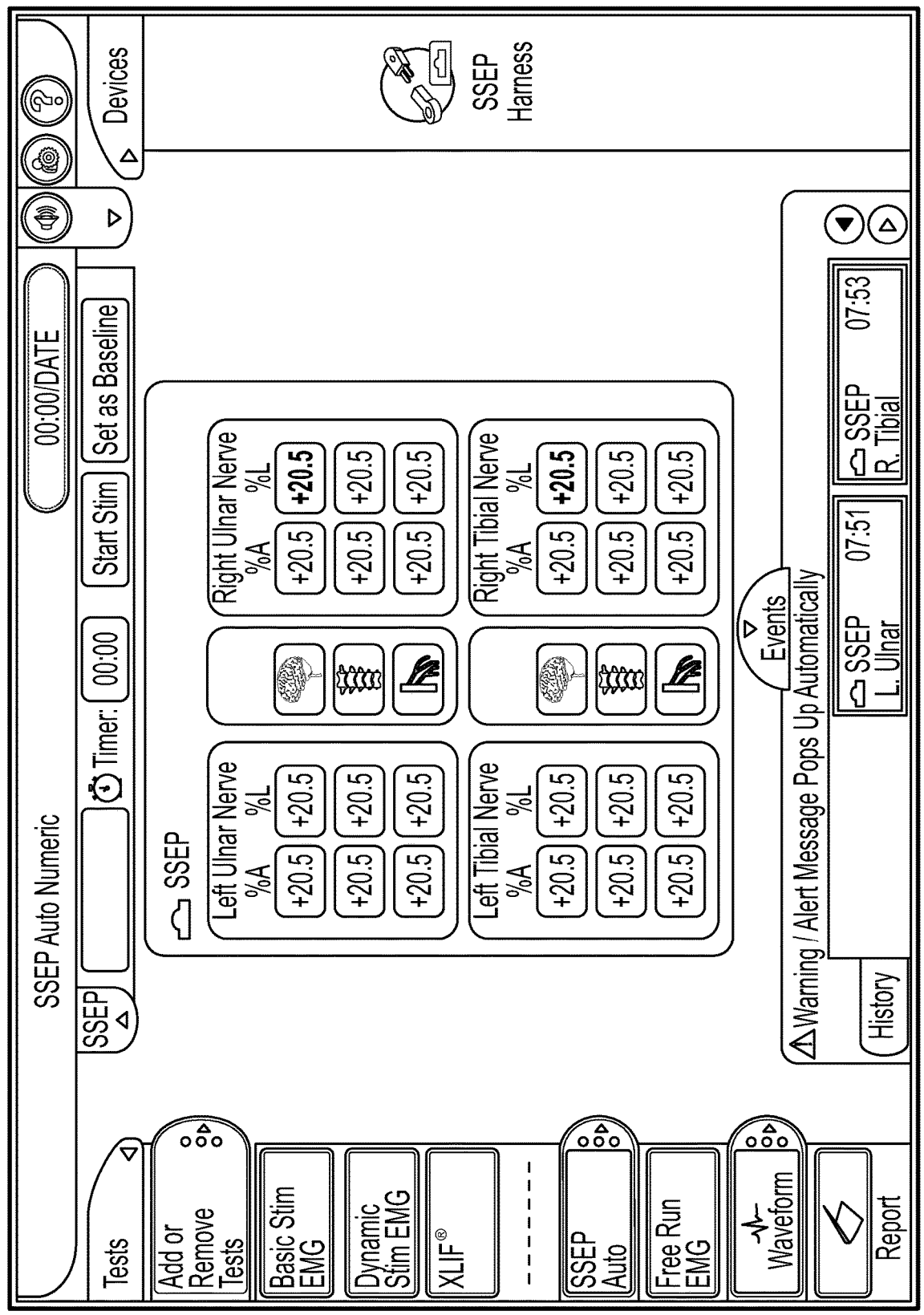
FIG. 35 is a screenshot of an example embodiment of an SSEP Manual monitoring screen forming part of the system of FIG. 1.
Figure 36:
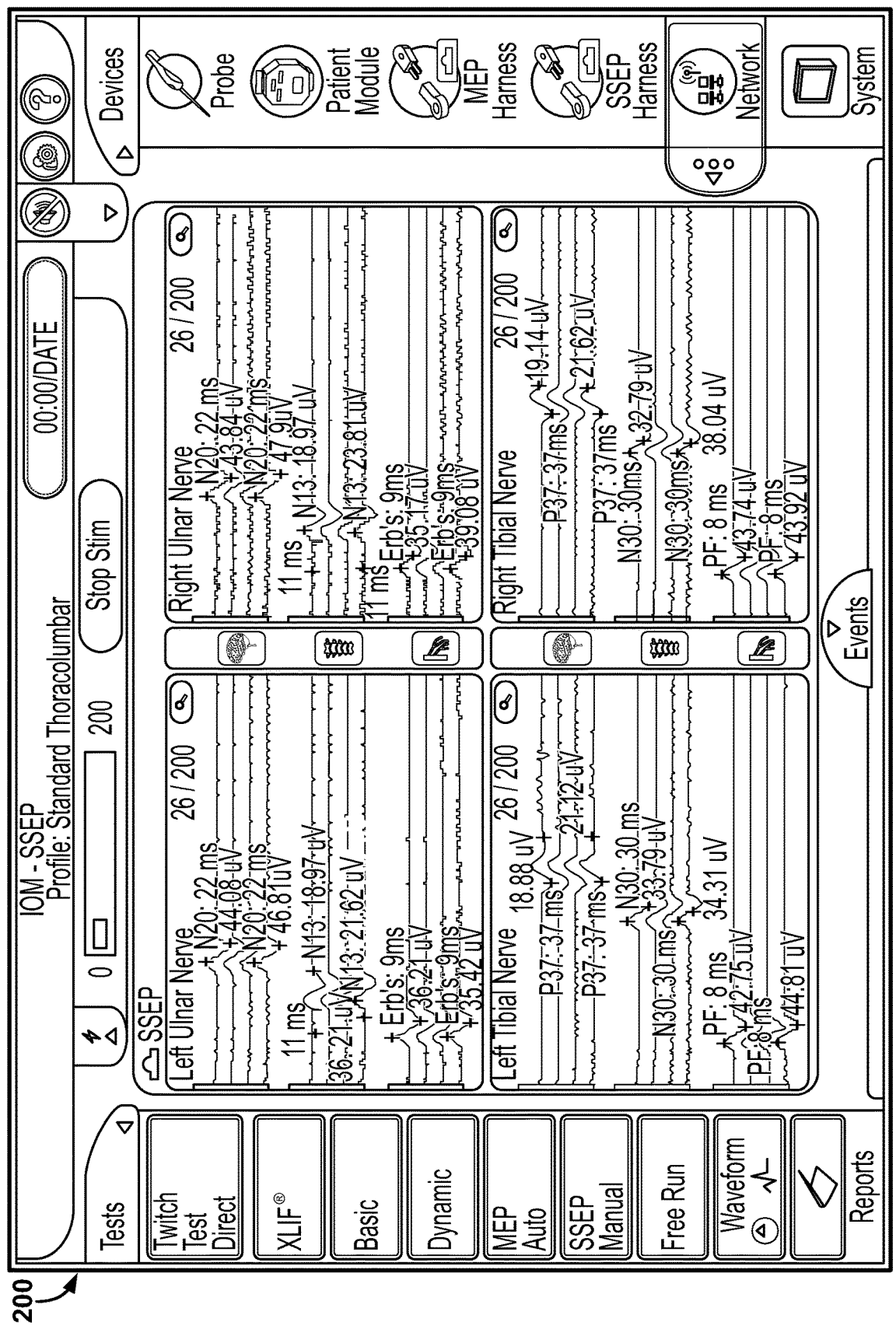
FIG. 36 is a screenshot of an example embodiment of an SSEP Automatic monitoring screen form part of the system of FIG. 1.
Figure 37:
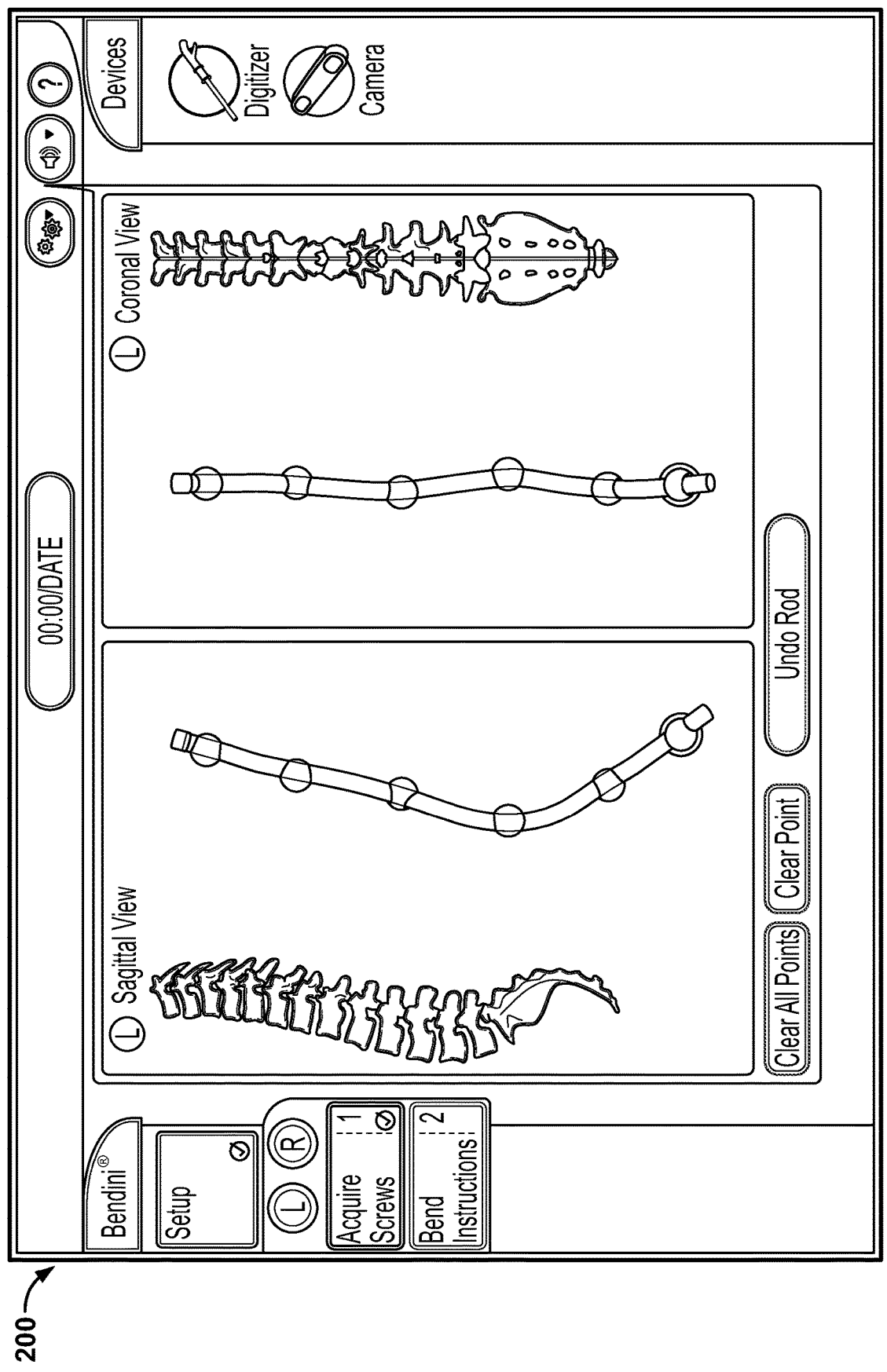
FIG. 37 is a screenshot of an example embodiment of a first surgical correction planning and assessment screen forming part of the system of FIG. 1.

In the SSEP Manual and Automatic modes, stimulation signals are delivered to peripheral sensory electrodes placed over the desired peripheral nerve (such as, by way of example only, the Posterior Tibial nerve and/or the Ulnar nerve) and recording electrodes 23 are positioned on or over the recording sites (such as, by way of example only, over the C2 vertebra, scalp, Erb's Point, and Popliteal Fossa), and stimulation signals are delivered from the patient module 14. Damage in the spinal cord may disrupt the transmission of the signal up the spinal cord resulting in a weakened or delayed signal at the recording site. In SSEP Manual mode, the signal response waveforms and latency values associated with those waveforms are displayed for the user. The user then makes a comparison between a baseline signal response and a signal response, as depicted in FIG. 35. In SSEP Automatic mode, the system 10 compares the difference between the amplitude and latency of the signal response vs. the amplitude and latency of a baseline signal response. These differences are compared against the predetermined "safe" and "unsafe" levels and the results are displayed on display 34. The results are displayed to the user along with any other indicia of the safety level determined (such as a red, yellow, green color code), on the display 34, as illustrated in FIG. 36). According to some embodiments, the system 10 may employ one or more algorithms to quickly select the optimal stimulus parameters for conducting SSEP testing on each active stimulation channel. This can be done according to any number of algorithms that automatically adjust various parameters until a combination resulting in the most desirable result is achieved.

Figure 38:
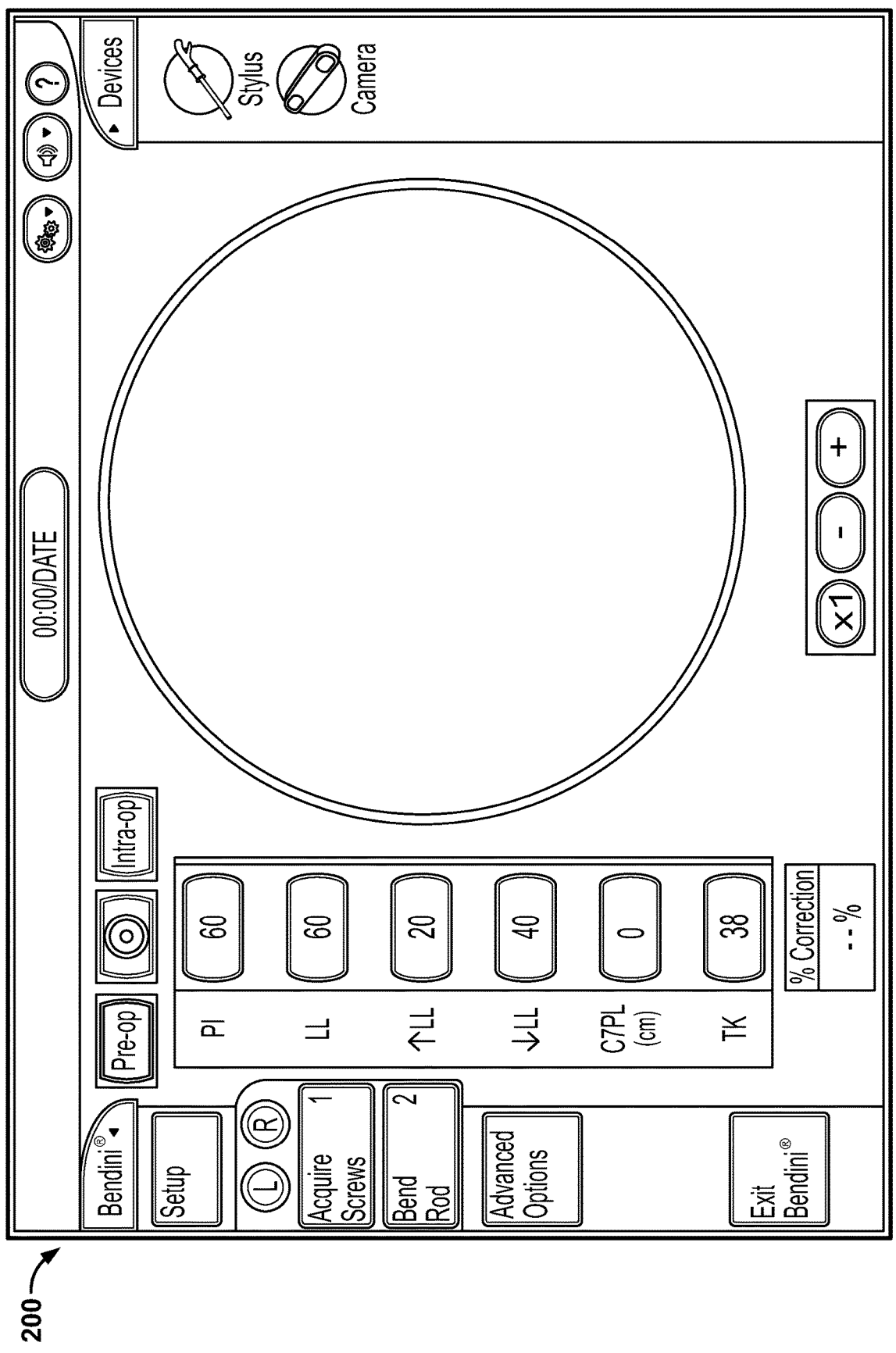
FIG. 38 is a screenshot of an example embodiment of second surgical correction planning and assessment screen forming part of the system of FIG. 1.
Figure 39A:
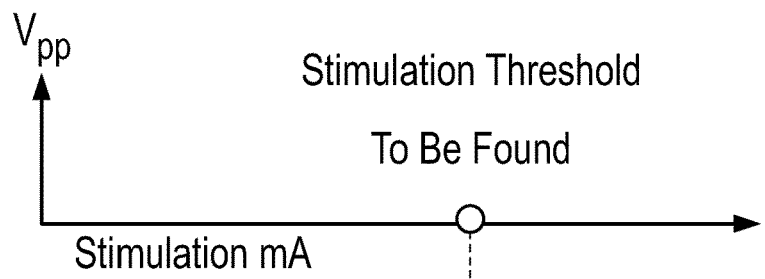
FIGS. 39A-D are graphs illustrating the fundamental steps of a rapid current threshold-hunting algorithm according to one embodiment of the present invention.
Figure 39B:
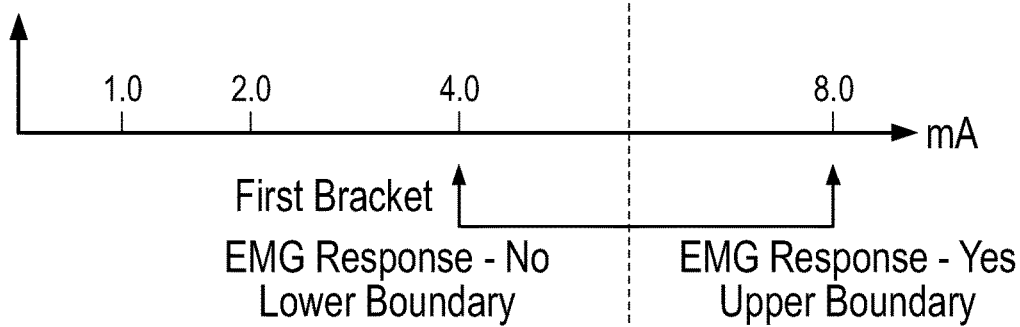
Figure 39C:
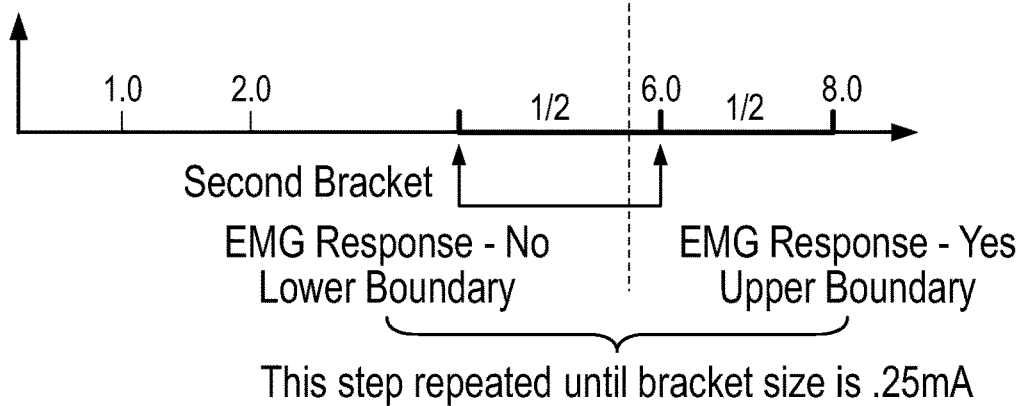
Figure 39D:
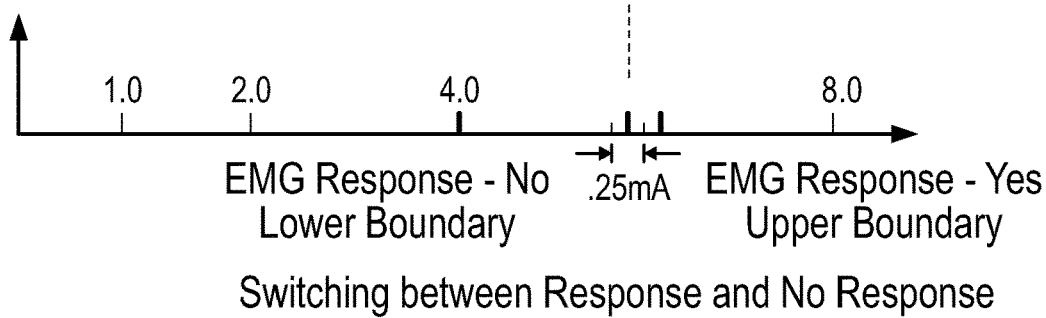

In the surgical correction planning and assessment mode, the system 10 aids the user in planning and assessing the degree to which he/she has achieved the surgical goals during a spinal procedure. As illustrated, by way of example only, in FIG. 37, there may be included a feature in which the system 10 is capable of digitizing implanted screw positions, outputting bend instructions for a rod, and previewing the shape of the rod on screen 200. In some implementations, the rod bending instructions are for a rod shaped to custom-fit within the implanted screw locations. In other implementations, the system 10 is further capable of accepting correction inputs via one or more advanced option features for viewing bend instructions for a rod shaped to fit at locations apart from those implanted screw locations. Installing a rod shaped in this manner could correct a curvature deformity in the patient's spine according to a user's prescribed surgical plan. In some spinal procedures, restoring a patient's spine to a balanced position may be a desired surgical outcome. As shown in FIG. 38, there may also be included a feature in which the system 10 is configured to receive and assess 1) preoperative spinal parameter inputs; 2) target spinal parameter inputs; 3) intraoperative spinal parameter inputs; and/or postoperative spine parameter inputs via screen 200. Spinal parameters may comprise the patient's Pelvic Incidence (PI), Pelvic Tilt (PT), Sacral Slope (SS), Lumbar Lordosis (LL), Superior Lumbar Lordosis (↑LL), Inferior Lumbar Lordosis (↓LL), C7 Plumb Line Offset (C7PL), Thoracic Kyphosis (TK), T1 Tilt, and Sagittal, Vertical Axis (SVA) measurements. One or more of these inputs may be tracked and/or compared against other inputs to assess how the surgical correction is progressing toward a surgical plan and utilized to develop/refine an operative plan to achieve the desired surgical correction.

To obtain $I_{thresh}$ and take advantage of the useful information it provides, the system 10 identifies and measures the peak-to-peak voltage ($V_{pp}$) of each EMG response corresponding to a given stimulation current ($I_{Stim}$). Identifying the true $V_{pp}$ of a response may be complicated by the existence of stimulation and/or noise artifacts which may create an erroneous $V_{pp}$ measurement. To overcome this challenge, the system 10 of the present invention may employ any number of suitable artifact rejection techniques such as those shown and described in full in the above referenced co-pending and commonly assigned PCT App. Ser. No. PCT/US2004/025550, entitled "System and Methods for Performing Dynamic Pedicle Integrity Assessments," filed on Aug. 5, 2004, the entire contents of which are incorporated by reference into this disclosure as if set forth fully herein. Upon measuring $V_{pp}$ for each EMG response, the $V_{pp}$ information is analyzed relative to the corresponding stimulation current ($I_{stim}$) in order to identify the minimum stimulation current ($I_{Thresh}$) capable of resulting in a predetermined $V_{pp}$ EMG response. According to the present invention, the determination of $I_{Thresh}$ may be accomplished via any of a variety of suitable algorithms or techniques.

FIGS. 39 A-D illustrate, by way of example only, the principles of a threshold hunting algorithm of the present invention used to quickly find $I_{thresh}$. The method for finding $I_{thresh}$ utilizes a bracketing method and a bisection method. The bracketing method quickly finds a range (bracket) of stimulation currents that must contain $I_{thresh}$ and the bisection method narrows the bracket until $I_{thresh}$ is known within a specified accuracy. If the stimulation current threshold, $I_{thresh}$, of a channel exceeds a maximum stimulation current, that threshold is considered out of range.

FIGS. 39 A-D illustrate the bracketing feature of the threshold hunting algorithm of the present invention. Stimulation begins at a minimum stimulation current, such as (by way of example only) 1 mA. It will be appreciated that the relevant current values depend in part on the function performed (e.g. high currents are used for MEP and low currents are generally used for other functions) and the current values described here are for purposes of example only and may in actuality be adjusted to any scale. The level of each subsequent stimulation is doubled from the preceding stimulation level until a stimulation current recruits (i.e. results in an EMG response with a $V_{pp}$ greater or equal to $V_{thresh}$). The first stimulation current to recruit (8 mA in FIG. 39 B), together with the last stimulation current to have not recruited (4 mA in FIG. 39 B), forms the initial bracket.

FIGS. 39 C-D illustrate the bisection feature of the threshold hunting algorithm of the present invention. After the threshold current $I_{thresh}$ has been bracketed (FIG. 39 B), the initial bracket is successively reduced via bisection to a predetermined width, such as (by way of example only) 0.25 mA. This is accomplished by applying a first bisection stimulation current that bisects (i.e. forms the midpoint of) the initial bracket (6 mA in FIG. 39 C). If this first bisection stimulation current recruits, the bracket is reduced to the lower half of the initial bracket (e.g. 4 mA and 6 mA in FIG. 39 C). If this first bisection stimulation current does not recruit, the bracket is reduced to the upper half of the initial bracket (e.g. 6 mA and 8 mA in FIG. 39 C). This process is continued for each successive bracket until $I_{thresh}$ is bracketed by stimulation currents separated by the predetermined width (which, in this case, is 0.25 mA). In this example shown, this would be accomplished by applying a second bisection stimulation current (forming the midpoint of the second bracket, or 5 mA in this example). Because this second bisection stimulation current is below $I_{thresh}$, it will not recruit. As such, the second bracket will be reduced to the upper half thereof (5 mA to 6 mA), forming a third bracket. A third bisection stimulation current forming the mid-point of the third bracket (5.50 mA in this case) will then be applied. Because this third bisection stimulation current is below $I_{thresh}$, it will not recruit. As such, the third bracket will be reduced to the upper half thereof (5.50 mA to 6 mA), forming a fourth bracket. A fourth bisection stimulation current forming the mid-point of the fourth bracket (5.75 mA in this case) will then be applied. Because the fourth bisection stimulation current is above $I_{thresh}$, it will recruit. The final bracket is therefore between 5.50 mA and 5.75 mA. Due to the "response" or recruitment at 5.50 mA and "no response" or lack of recruitment at 5.75 mA, it can be inferred that $I_{thresh}$ is within this range. In one embodiment, the midpoint of this final bracket may be defined as $I_{thresh}$, however, any value falling within the final bracket may be selected as $I_{thresh}$ without departing from the scope of the present invention. Depending on the active mode, the algorithm may stop after finding $I_{thresh}$ for the first responding channel (i.e. the channel with the lowest $I_{thresh}$) or the bracketing and bisection steps may be repeated for each channel to determine $I_{thresh}$ for each channel. In one embodiment, this multiple channel $I_{thresh}$ determination may be accomplished by employing the additional steps of the multi-channel threshold detection algorithm, described below.

Additionally, in the "dynamic" functional modes, including, but not necessarily limited to Dynamic Stimulation EMG and XLIF, the system may continuously update the stimulation threshold level and indicate that level to the user. To do so, the threshold hunting algorithm does not repeatedly determine the $I_{thresh}$ level anew, but rather, it determines whether stimulation current thresholds are changing. This is accomplished, as illustrated in FIG. 39 D, by a monitoring phase that involves switching between stimulations at lower and upper ends of the final bracket. If the threshold has not changed then the lower stimulation current should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm transitions back to the bracketing state in order to reestablish the bracket. In the event a change in $I_{thresh}$ is detected during the monitoring phase, the user may be alerted immediately via the screen display and/or audio feedback. By way of example only, the color shown on the display corresponding to the previous $I_{thresh}$ can be altered to a neutral color (e.g. black, grey, etc. . . . ) as soon as the change in $I_{thresh}$ is detected but before the new $I_{thresh}$ value is determined. If an audio tone is used to represent a particular safety level, the tone can ceased as soon as the change in detected. Once the new $I_{thresh}$ value is determined the color and/or audio tone can be altered again to signify the value.

Figure 40:
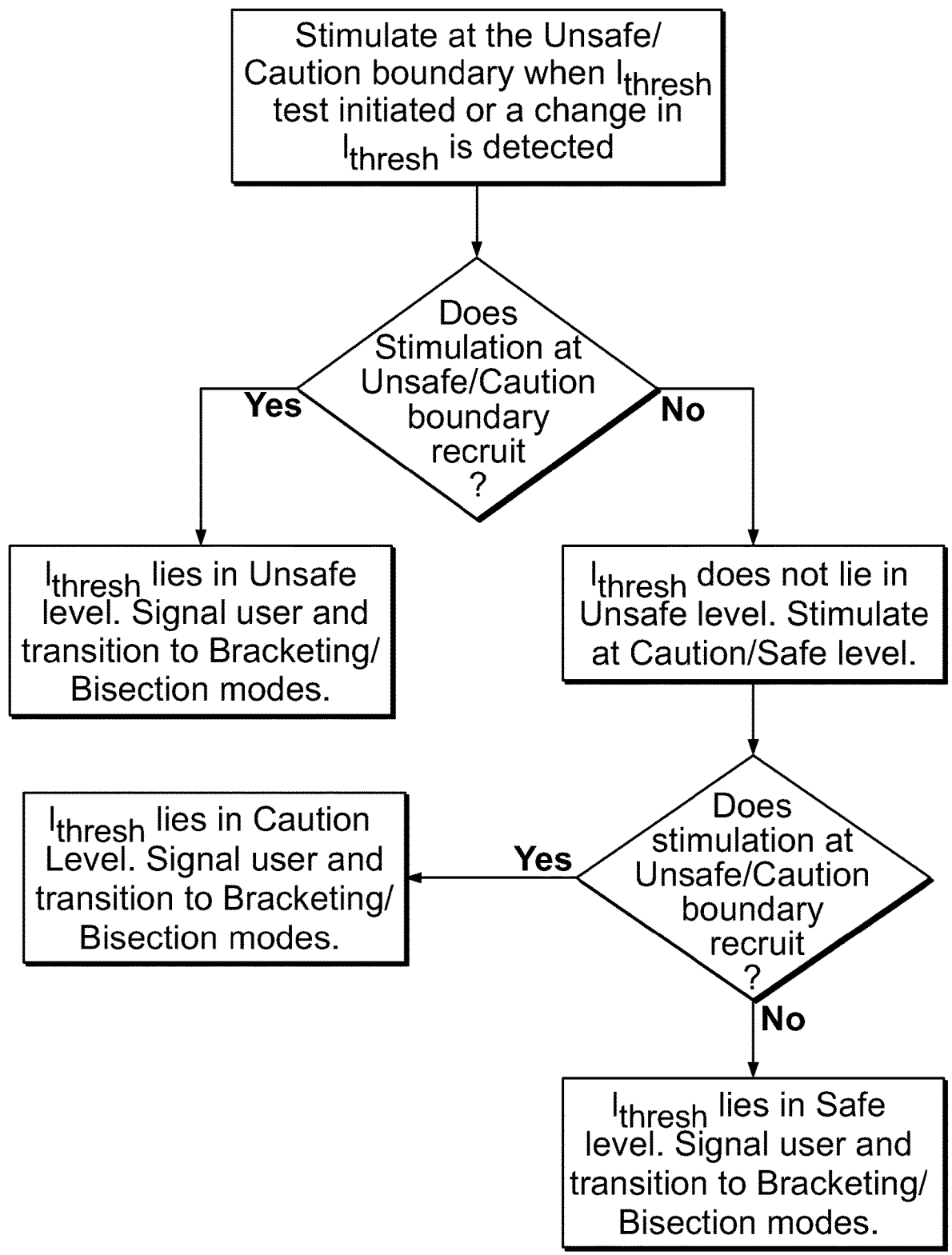
FIG. 40 is a block diagram illustrating the steps of an initiation sequence for determining a relevant safety level prior to determining a precise threshold value according to an alternate embodiment of the threshold hunting algorithm of FIGS. 39A-D.

In an alternative embodiment, rather than beginning by entering the bracketing phase at the minimum stimulation current and bracketing upwards until $I_{thresh}$ is bracketed, the threshold hunting algorithm may begin by immediately determining the appropriate safety level and then entering the bracketing phase. The algorithm may accomplish this by initiating stimulation at one or more of the boundary current levels. By way of example only, and with reference to FIG. 40, the algorithm may begin by delivering a stimulation signal at the boundary between the unsafe (e.g. red) and caution (e.g. yellow) levels. If the safety level is not apparent after the first stimulation, the algorithm may stimulate again at the boundary between the caution (e.g. yellow) and safe (e.g. green) levels. Once the safety level is known (i.e. after the first stimulation if the safety level is red, or, after the second stimulation if the safety level is yellow or green) the screen display may be updated to the appropriate color and/or coded audio signals may be emitted. As the screen display is updated, the algorithm may transition to the bracketing and bisection phases to determine the actual $I_{thresh}$ value. When the $I_{thresh}$ value is determined the display may be updated again to reflect the additional information. In dynamic modes, if the monitoring phase detects a change in $I_{thresh}$, the algorithm will again stimulate at the boundary level(s) as necessary and update the color and/or audio signals before transitioning to the bracketing and bisection phases to determine the new $I_{thresh}$.

For some functions, such as (by way of example) MEP, it may be desirable to obtain $I_{thresh}$ for each active channel each time the function is performed. This is particularly advantageous when assessing changes in $I_{thresh}$ over time as a means to detect potential problems (as opposed to detecting an $I_{thresh}$ below a predetermined level determined to be safe, such as in the Stimulated EMG modes). While $I_{thresh}$ can be found for each active channel using the algorithm as described above, it requires a potentially large number of stimulations, each of which is associated with a specific time delay, which can add significantly to the response time. Done repeatedly, it could also add significantly to the overall time required to complete the surgical procedure, which may present added risk to the patient and added costs. To overcome this drawback, a preferred embodiment of the system 10 boasts a multi-channel threshold hunting algorithm so as to quickly determine $I_{thresh}$ for each channel while minimizing the number of stimulations and thus reduce the time required to perform such determinations.

The multi-channel threshold hunting algorithm reduces the number stimulations required to complete the bracketing and bisection steps when $I_{thresh}$ is being found for multiple channels. The multi-channel algorithm does so by omitting stimulations for which the result is predictable from the data already acquired. When a stimulation signal is omitted, the algorithm proceeds as if the stimulation had taken place. However, instead of reporting an actual recruitment result, the reported result is inferred from previous data. This permits the algorithm to proceed to the next step immediately, without the time delay associated with a stimulation signal.

Regardless of what channel is being processed for $I_{thresh}$, each stimulation signal elicits a response from all active channels. That is to say, every channel either recruits or does not recruit in response to a stimulation signal (again, a channel is said to have recruited if a stimulation signal evokes an EMG response deemed to be significant on that channel, such as $V_{pp}$ of approximately 100 uV). These recruitment results are recorded and saved for each channel. Later, when a different channel is processed for $I_{thresh}$, the saved data can be accessed and, based on that data, the algorithm may omit a stimulation signal and infer whether or not the channel would recruit at the given stimulation current.

There are two reasons the algorithm may omit a stimulation signal and report previous recruitment results. A stimulation signal may be omitted if the selected stimulation current would be a repeat of a previous stimulation. By way of example only, if a stimulation current of 1 mA was applied to determine $I_{thresh}$ for one channel, and a stimulation at 1 mA is later required to determine $I_{thresh}$ for another channel, the algorithm may omit the stimulation and report the previous results. If the specific stimulation current required has not previously been used, a stimulation signal may still be omitted if the results are already clear from the previous data. By way of example only, if a stimulation current of 2 mA was applied to determine $I_{thresh}$ for a previous channel and the present channel did not recruit, when a stimulation at 1 mA is later required to determine $I_{thresh}$ for the present channel, the algorithm may infer from the previous stimulation that the present channel will not recruit at 1 mA because it did not recruit at 2 mA. The algorithm may therefore omit the stimulation and report the previous result.

Figure 41:
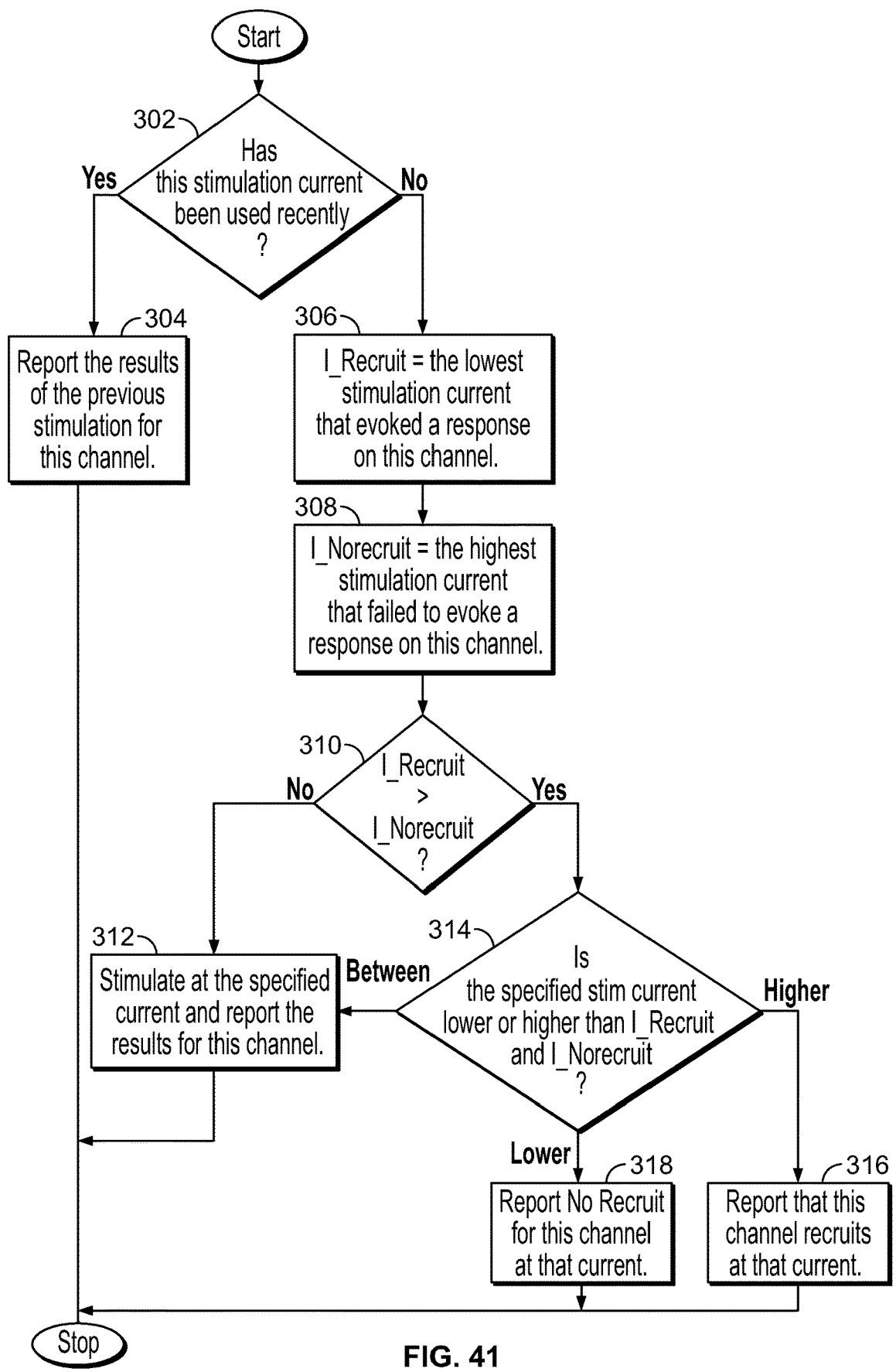
FIG. 41 is a flowchart illustrating the method by which a multi-channel hunting algorithm determines whether to perform or omit a stimulation.

FIG. 41 illustrates (in flowchart form) a method by which the multi-channel threshold hunting algorithm determines whether to stimulate, or not stimulate and simply report previous results. The algorithm first determines if the selected stimulation current has already been used (step 302). If the stimulation current has been used, the stimulation is omitted and the results of the previous stimulation are reported for the present channel (step 304). If the stimulation current has not been used, the algorithm determines $I_{recruit}$ (step 306) and $I_{norecruit}$ (step 308) for the present channel. $I_{recruit}$ is the lowest stimulation current that has recruited on the present channel. $I_{norecruit}$ is the highest stimulation current that has failed to recruit on the present channel. The algorithm next determines whether $I_{recruit}$ is greater than $I_{norecruit}$ (step 310). An $I_{recruit}$ that is not greater than $I_{norecruit}$ is an indication that changes have occurred to $I_{thresh}$ on that channel. Thus, previous results may not be reflective of the present threshold state and the algorithm will not use them to infer the response to a given stimulation current. The algorithm will stimulate at the selected current and report the results for the present channel (step 312). If $I_{recruit}$ is greater than $I_{norecruit}$, the algorithm determines whether the selected stimulation current is higher than $I_{recruit}$, lower than $I_{norecruit}$, or between $I_{recruit}$ and $I_{norecruit}$ (step 314). If the selected stimulation current is higher than $I_{recruit}$, the algorithm omits the stimulation and reports that the present channel recruits at the specified current (step 316). If the selected stimulation current is lower than $I_{norecruit}$, the algorithm infers that the present channel will not recruit at the selected current and reports that result (step 318). If the selected stimulation current falls between $I_{recruit}$ and $I_{norecruit}$, the result of the stimulation cannot be inferred and the algorithm stimulates at the selected current and reports the results for the present channel (step 312). This method may be repeated until $I_{thresh}$ has been determined for every active channel.

Figure 42A:
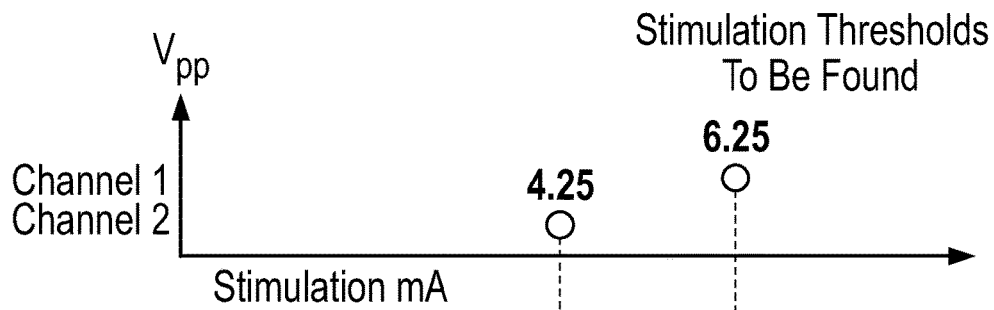
FIGS. 42A-C are graphs illustrating use of the threshold hunting algorithm of FIG. 41 and further omitting stimulations when the likely result is already clear from previous data.
Figure 42B:
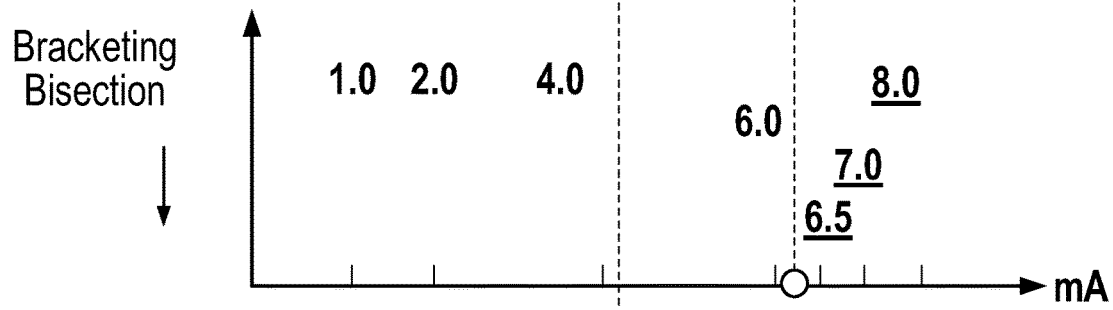
Figure 42C:
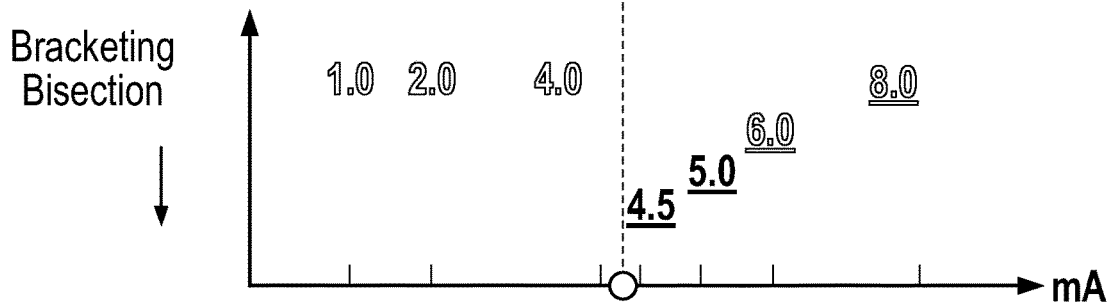

In the interest of clarity, FIGS. 42 A-C demonstrate use of the multi-channel threshold hunting algorithm to determine $I_{thresh}$ on only two channels. It should be appreciated, however, that the multi-channel algorithm is not limited to finding $I_{thresh}$ for two channels, but rather it may be used to find $I_{thresh}$ for any number of channels, such as (for example) eight channels according to a preferred embodiment of the system 10. With reference to FIG. 42 A, channel 1 has an $I_{thresh}$ to be found of 6.25 mA and channel 2 has an $I_{thresh}$ to be found of 4.25 mA. $I_{thresh}$ for channel 1 is found first as illustrated in FIG. 38 B, using the bracketing and bisection methods discussed above. Bracketing begins at the minimum stimulation current (for the purposes of example only) of 1 mA. As this is the first channel processed and no previous recruitment results exist, no stimulations are omitted. The stimulation current is doubled with each successive stimulation until a significant EMG response is evoked at 8 mA. The initial bracket of 4-8 mA is bisected, using the bisection method described above, until the stimulation threshold, $I_{thresh}$, is contained within a final bracket separated by the selected width or resolution (again 0.25 mA). In this example, the final bracket is 6 mA-6.25 mA. $I_{thresh}$ may be defined as any point within the final bracket or as the midpoint of the final bracket (6.125 mA in this case). In either event, $I_{thresh}$ is selected and reported as $I_{thresh}$ for channel 1.

Once $I_{thresh}$ is found for channel 1, the algorithm turns to channel 2, as illustrated in FIG. 42 C. The algorithm begins to process channel 2 by determining the initial bracket, which is again 4-8 mA. All the stimulation currents required in the bracketing state were used in determining $I_{thresh}$ for channel 1. The algorithm refers back to the saved data to determine how channel 1 responded to the previous stimulations. From the saved data, the algorithm may infer that channel 2 will not recruit at stimulation currents of 1, 2, and 4 mA, and will recruit at 8 mA. These stimulations are omitted and the inferred results are displayed. The first bisection stimulation current selected in the bisection process (6 mA in this case), was previously used and, as such, the algorithm may omit the stimulation and report that channel 2 recruits at that stimulation current. The next bisection stimulation current selected (5 mA in this case) has not been previously used and, as such, the algorithm must determine whether the result of a stimulation at 5 mA may still be inferred. In the example shown, $I_{recruit}$ and $I_{norecruit}$ are determined to be 6 mA and 4 mA, respectively. Because 5 mA falls in between $I_{recruit}$ and $I_{norecruit}$, the algorithm may not infer the result from the previous data and, as such, the stimulation may not be omitted. The algorithm then stimulates at 5 mA and reports that the channel recruits. The bracket is reduced to the lower half (making 4.50 mA the next bisection stimulation current). A stimulation current of 4.5 mA has not previously been used and, as such, the algorithm again determines $I_{recruit}$ and $I_{norecruit}$ (5 mA and 4 mA in this case). The selected stimulation current (4.5 mA) falls in between $I_{recruit}$ an $I_{norecruit}$ and, as such, the algorithm stimulates at 4.5 mA and reports the results. The bracket now stands at its final width of 0.25 mA (for the purposes of example only). $I_{thresh}$ may be defined as any point within the final bracket or as the midpoint of the final bracket (4.125 mA in this case). In either event, $I_{thresh}$ is selected and reported as $I_{thresh}$ for channel 2.

Although the multi-channel threshold hunting algorithm is described above as processing channels in numerical order, it will be understood that the actual order in which channels are processed is immaterial. The channel processing order may be biased to yield the highest or lowest threshold first (discussed below) or an arbitrary processing order may be used. Furthermore, it will be understood that it is not necessary to complete the algorithm for one channel before beginning to process the next channel, provided that the intermediate state of the algorithm is retained for each channel. Channels are still processed one at a time. However, the algorithm may cycle between one or more channels, processing as few as one stimulation current for that channel before moving on to the next channel. By way of example only, the algorithm may stimulate at 10 mA while processing a first channel for $I_{thresh}$. Before stimulating at 20 mA (the next stimulation current in the bracketing phase), the algorithm may cycle to any other channel and process it for the 10 mA stimulation current (omitting the stimulation if applicable). Any or all of the channels may be processed this way before returning to the first channel to apply the next stimulation. Likewise, the algorithm need not return to the first channel to stimulate at 20 mA, but instead may select a different channel to process first at the 20 mA level. In this manner, the algorithm may advance all channels essentially together and bias the order to find the lower threshold channels first or the higher threshold channels first. By way of example only, the algorithm may stimulate at one current level and process each channel in turn at that level before advancing to the next stimulation current level. The algorithm may continue in this pattern until the channel with the lowest $I_{thresh}$ is bracketed. The algorithm may then process that channel exclusively until $I_{thresh}$ is determined, and then return to processing the other channels one stimulation current level at a time until the channel with the next lowest $I_{thresh}$ is bracketed. This process may be repeated until $I_{thresh}$ is determined for each channel in order of lowest to highest $I_{thresh}$. If $I_{thresh}$ for more than one channel falls within the same bracket, the bracket may be bisected, processing each channel within that bracket in turn until it becomes clear which one has the lowest $I_{thresh}$. If it becomes more advantageous to determine the highest $I_{thresh}$ first, the algorithm may continue in the bracketing state until the bracket is found for every channel and then bisect each channel in descending order.

Figure 43A:
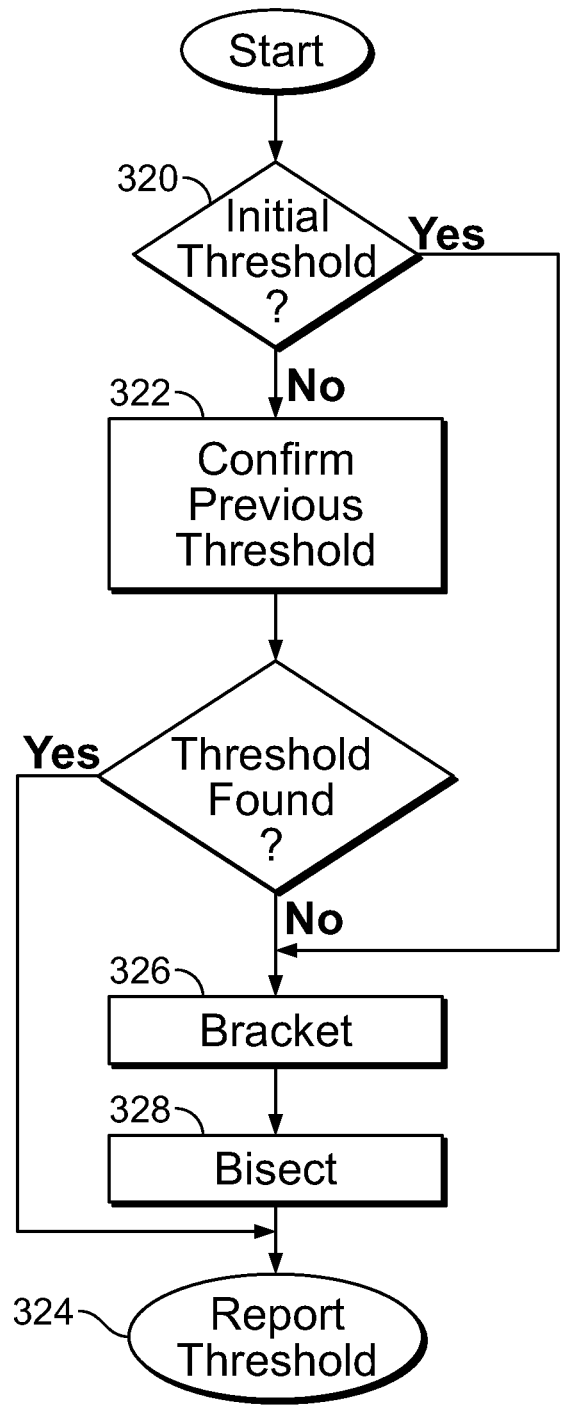
FIG. 43A is a flowchart illustrating the sequence employed by the algorithm to determine and monitor $I_{thresh}$.
Figure 43B:
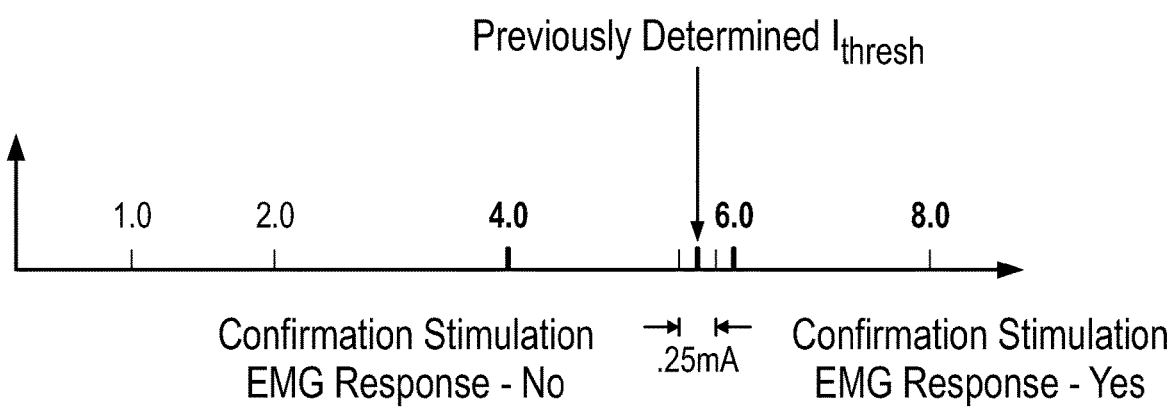
FIG. 43B is a graph illustrating the confirmation step employed by the algorithm to determine whether $I_{thresh}$ has changed from a previous determination.

FIGS. 43 A-B illustrates a further feature of the threshold hunting algorithm of the present invention, which advantageously provides the ability to further reduce the number of stimulations required to find $I_{thresh}$ when an $I_{thresh}$ value has previously been determined for a specific channel. In the event that a previous $I_{thresh}$ determination exists for a specific channel, the algorithm may begin by merely confirming the previous $I_{thresh}$ rather than beginning anew with the bracketing and bisection methods. The algorithm first determines whether it is conducting the initial threshold determination for the channel or whether there is a previous $I_{thresh}$ determination (step 320). If it is not the initial determination, the algorithm confirms the previous determination (step 322) as described below. If the previous threshold is confirmed, the algorithm reports that value as the present $I_{thresh}$ (step 324). If it is the initial $I_{thresh}$ determination, or if the previous threshold cannot be confirmed, then the algorithm performs the bracketing function (step 326) and bisection function (step 328) to determine $I_{thresh}$ and then reports the value (step 324).

Although the hunting algorithm is discussed herein in terms of finding $I_{thresh}$ (the lowest stimulation current that evokes a predetermined EMG response), it is contemplated that alternative stimulation thresholds may be useful in assessing the health of the spinal cord or nerve monitoring functions and may be determined by the hunting algorithm. By way of example only, the hunting algorithm may be employed by the system 10 to determine a stimulation voltage threshold. This is the lowest stimulation voltage necessary to evoke a significant EMG response. Bracketing, bisection and monitoring states are conducted as described above for each active channel, with brackets based on voltage being substituted for the current based brackets previously described. Moreover, although described above within the context of MEP monitoring, it will be appreciated that the algorithms described herein may also be used for determining the stimulation threshold (current or voltage) for any other EMG related functions, including but not limited to pedicle integrity (screw test), nerve detection, and nerve root retraction.

Figure 44A:
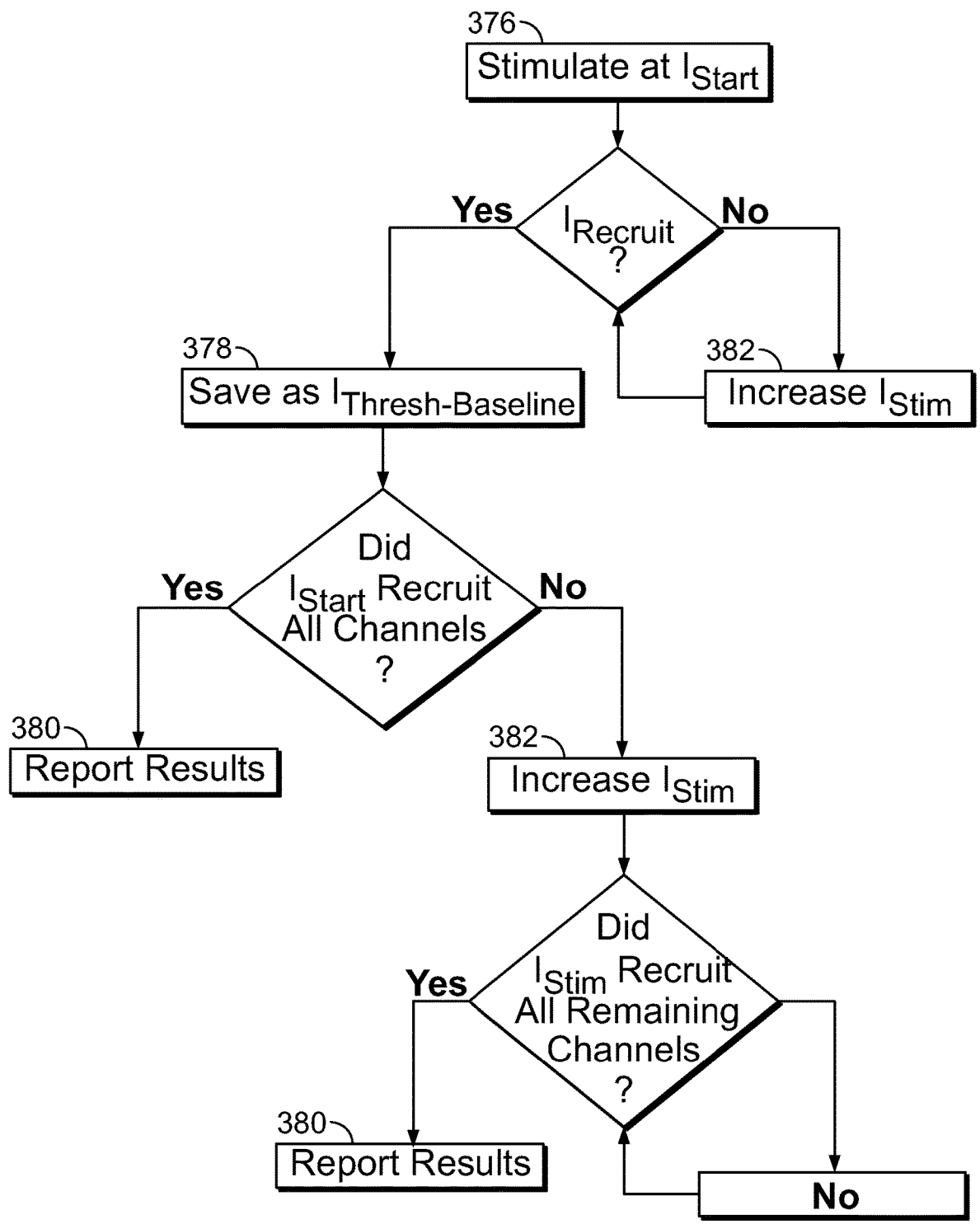
FIGS. 44A-44B are flowcharts illustrating the sequence of a rapid thresholding algorithm according to one first embodiment.

FIGS. 44 A-B depict, by way of example only, the principles of a focused linear thresholding algorithm of the present invention used to quickly elicit a significant evoked neuromuscular response. The method for finding the evoked neuromuscular response utilizes a baseline ramping method and a subsequent ramping method to find $I_{thresh}$. The baseline ramping method quickly finds stimulation intensity that generates a significant evoked neuromuscular response in each channel within a specified accuracy. The subsequent ramping method uses the baseline ramping results to find the minimum stimulation current threshold intensity that generates a significant neuromuscular response in each channel within a specified accuracy.

The baseline linear ramping method quickly finds a minimum stimulation intensity that generates responses by increasing $I_{stim}$ in a linear fashion until $I_{thresh}$ is known within a specified accuracy for each channel. Stimulation begins at a starting stimulation current, such as (by way of example only) 100 mA (step 376). It will be appreciated that the relevant current values depend in part on the function performed (e.g. high currents are used for TCNR and MEP and low currents are generally used for other functions) and the current values described here are for purposes of example only and may in actuality be adjusted to any scale.

The algorithm will increment each stimulation [level] from the preceding stimulation level by a fixed amount (e.g. 50 mA) until a stimulation level recruits a baseline neuromuscular response ($I_{thresh-baseline}$) for each channel (step 382). The lowest stimulation level to recruit a baseline neuromuscular response in at least one channel is saved for recall in the subsequent focused linear ramping algorithm (step 378). Once baseline $I_{thresh}$ values for all channels have been defined, the results are reported (step 380) to the control unit 12.

According to some neurophysiologic monitoring modalities (e.g. MEP), it may be desirable to obtain baseline response in dual polarity stimulation configurations. In some implementations, the baseline linear ramping method includes the optional step of switching the polarity of stimulation at each stimulation intensity level and reporting the results of $I_{thresh}$ and the associated polarity at step 380.

While $I_{thresh}$ can be found for each channel as described above with respect to the linear ramping method every time, it requires a potentially large number of stimulations, each of which is associated with a specific time delay, which can add significantly to the response time. Done repeatedly, it could also add significantly to the overall time required to compete the surgical procedure, which may present added risk to the patient and added costs. To overcome this drawback, the focused linear thresholding algorithm includes a subsequent focused ramping method so as to quickly determine $I_{thresh}$ for each channel while minimizing the total number of stimulations, lowering the total energy delivered, and reducing the time required to perform such determinations.

The subsequent focused linear ramping method may reduce the number of stimulations required to find $I_{thresh}$ during subsequent stimulations after baseline, particularly when $I_{thresh}$ is being found for multiple channels. The algorithm does so by omitting stimulations for which the result is predictable from the baseline data already acquired. This permits the algorithm to proceed to the next step immediately, without the time delay associated with an unnecessary stimulation signal. The algorithm may then quickly find $I_{thresh-subsequent}$ by using the lowest $I_{thresh-baseline}$ (i.e. threshold stimulus intensity of the first channel to recruit at baseline) and increasing the stimulus intensity in a linear fashion until $I_{thresh-subsequent}$ is known within a specified accuracy for each channel.

Figure 44B:
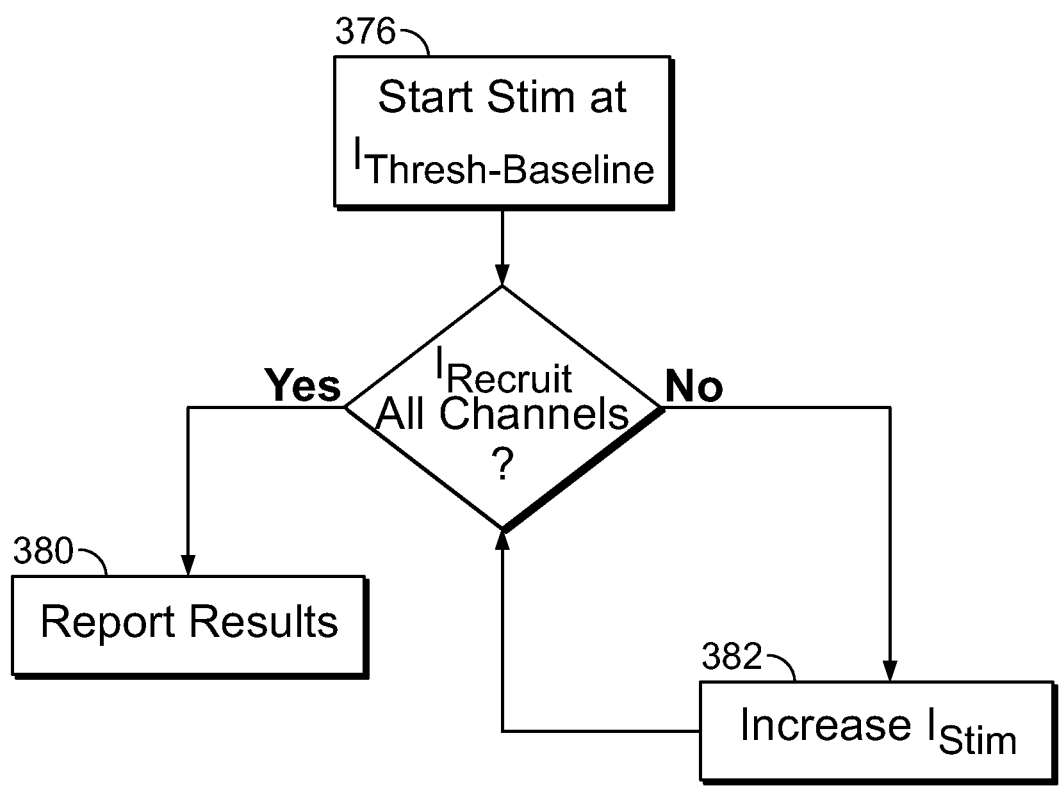

Referring back to the flowchart of FIG. 44B, in a subsequent TCNR test, the algorithm confirms the lowest baseline $I_{thresh}$ to recruit a response in at least one channel by stimulating at that $I_{stim}$ (step 376). In those implementations including a switching of polarity, the algorithm confirms the baseline at polarity in which the lowest $I_{thresh}$ was obtained. If the $I_{stim}$ at step 376 results in a response in all channels, the sequence stops and the results are reported to the control unit 12 (step 380). If the $I_{stim}$ at step 380 does not result in a response in all channels, the stimulation is increased a predetermined amount (step 382) and the sequence is repeated until a response is repeated in each channel. Once subsequent $I_{thresh}$ values for all channels have been defined, the results are reported (step 380) to the control unit 12.

Although the focused linear thresholding algorithm is discussed herein in terms of finding $I_{thresh}$ (the lowest threshold stimulation intensity that evokes a predetermined EMG response), it is contemplated that alternative thresholds may be useful in assessing the health of the lumbar motor neural pathways, spinal cord, or nerve monitoring functions and may be determined by the algorithm. By way of example only, the algorithm may be employed by the system 10 do determined a stimulation voltage threshold $Vstim_{thresh}$. This is the lowest stimulation voltage (as opposed to the lowest stimulation current) necessary to evoke a significant EMG response, $V_{thresh}$.

It will be appreciated that the focused linear thresholding algorithms described herein may also be used for determining the stimulation threshold (current or voltage) for any EMG-related functions, including but not limited to TCNR testing and MEP monitoring. Furthermore, it is to be understood that each neurophysiologic testing mode may include its own optimized stimulation profile, such that the term "stimulation" may comprise multiple meanings. By way of example only, TCNR stimulation may be a single pulse, such that the term "stimulation" may refer to a single pulse of stimulation energy whereas MEP stimulation may be a train of three to eight stimulation pulses such that the term "stimulation" may refer to a multiple train stimulation.

According to another broad aspect of the present disclosure, there is provided a method for monitoring the status of the motor neural pathway that includes the steps of: (a) stimulating the motor pathways in a transcutaneous and trans-abdominal fashion from a location superior (caudal, above) to the surgical site; (b) recording neurophysiologic responses evoked by that transcutaneous, trans-abdominal stimulation from one or more locations inferior (caudal, below) to the surgical site; and (c) comparing evoked responses over time to assess the health and status of the lower motor neural pathway. This particular method is useful in lumbar (as well as thoracic and thoracolumbar) spinal surgeries, where motor function may be at risk, to monitor and verify lumbar motor neural function throughout the procedure.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

Any combination of the nerve monitoring methods described herein may be employed at any one time without departing from the scope of the present disclosure. For example, the transcutaneous, trans-abdominal nerve root stimulation method described herein may be used in conjunction with the monitoring method described above during surgical access with a surgical access system.

What is claimed is:

1. A method during a spinal surgical procedure, said method comprising the steps of:
   adhering a cathode surface electrode to skin of a patient at a posterior location of the patient that is over the patient's conus medullaris at spinal level L1-2 and superior to a surgical target site;
   adhering an anode surface electrode to skin of the patient at an anterior location of the patient proximate the patient's anterior abdominal midline and that is superior to the surgical target site, wherein after the cathode surface electrode and the anode surface electrode have been adhered, the anode surface electrode has a larger surface area in contact with the patient's skin than the cathode surface electrode;
   delivering, periodically during the spinal surgical procedure, a first transcutaneous, transabdominal stimulation signal to lumbar motor neural pathways from the cathode electrode to the anode electrode;
   processing response signals received by one or more electrodes located inferior to the surgical target site in response to the first transcutaneous, transabdominal stimulation signal, thereby determining a first neuromuscular response data set;

after determining the first neuromuscular response data set, establishing an operative corridor to the surgical target site along a lateral, trans-psoas path; and monitoring changes to health of one or more nerves during the spinal surgical procedure by detecting changes to stimulation threshold intensities of the one or more nerves using the first neuromuscular response data set.

2. The method of claim 1, further comprising the steps of:

delivering a second transcutaneous, trans-abdominal stimulation signal to the lumbar motor neural pathways superior and inferior to the surgical target site; and determining a second neuromuscular response data set based on transmission of said second transcutaneous, trans-abdominal stimulation signal.

3. The method of claim 1, wherein the first transcutaneous, transabdominal stimulation signal is a single pulse signal.

4. The method of claim 1, further comprising the steps of:

delivering a second transcutaneous, trans-abdominal stimulation signal to the lumbar motor neural pathways superior and inferior to said surgical target site of said spinal surgical procedure;

determining a second neuromuscular response data set, based on transmission of said second transcutaneous, trans-abdominal stimulation signal, wherein the first and second transcutaneous, trans-abdominal stimulation signals are directed by a control unit, said control unit toggleable between a user-selected alert testing mode and a user-selected threshold testing mode and operating in the user-selected alert testing mode;

receiving said first and second neuromuscular response data sets in the control unit, evaluating automatically, by the control unit in said user-selected alert testing mode, said second neuromuscular response data set for a presence or absence of a response in said second neuromuscular response data set based on said second transcutaneous, trans-abdominal stimulation signal; and automatically displaying results indicative of the health or status of the one or more nerves during the spinal surgical procedure based on the evaluation by the control unit operating in the user-selected alert testing mode.

5. The method of claim 4, wherein the steps of delivering said second transcutaneous, trans-abdominal stimulation signal, determining said second neuromuscular response data set, receiving said first and second neuromuscular response data sets in the control unit, and evaluating said second neuromuscular response data set are performed periodically.

6. The method of claim 1, further comprising the steps of:

delivering a second transcutaneous, trans-abdominal stimulation signal to the lumbar motor neural pathways superior and inferior to said surgical target site of said spinal surgical procedure;

determining a second neuromuscular response data set, based on transmission of said second transcutaneous, trans-abdominal stimulation signal, wherein the first and second transcutaneous, trans-abdominal stimulation signals are directed by a control unit, said control unit toggleable between a user-selected alert testing mode and user-selected threshold testing mode and operating in the user-selected threshold testing mode, and wherein the intensity of the first and second transcutaneous, trans-abdominal stimulation signals are determined by the control unit;

receiving said first and second neuromuscular response data sets in the control unit, comparing automatically, by the control unit in said user-selected threshold testing mode, said intensities of said first and second transcutaneous, trans-abdominal stimulation signals to determine if the difference between said intensities of said first and second transcutaneous, trans-abdominal stimulation signals exceed a pre-determined threshold; and automatically displaying results indicative of the health or status of the one or more nerves during the spinal surgical procedure based on the comparison by the control unit operating in the user-selected threshold testing mode.

7. The method of claim 6, further comprising automatically providing a warning based on the comparing step, wherein the warning is at least one of a color code or an audio feedback.

8. The method of claim 6, further comprising establishing baseline responses for all muscles of interest.

9. The method of claim 1, further comprising:

via a control unit configured to cause said transcutaneous, trans-abdominal stimulation via the cathode electrode:

activating a first timer corresponding to a first predetermined time interval responsive to delivering said trans-abdominal stimulation;

responsive to the first timer indicating that the first predetermined time interval elapsed:

activating a first reminder alert configured to remind a user to perform a transcutaneous nerve root test; and;

activating a second timer corresponding to a second predetermined time interval responsive to the second timer indicating that the second predetermined time interval elapsed, activating a second reminder alert configured to remind the user to perform a transcutaneous nerve root test; and responsive to detecting actuation of a start stimulation button after activating the second reminder alert, restarting the first timer and silencing the second reminder alert.

10. The method of claim 1, wherein establishing the operative corridor to the surgical target site along the lateral, trans-psoas path includes:

inserting a retractor into the patient; and causing electrical stimulation to be provided with an electrode coupled to the retractor to perform nerve proximity testing.

11. The method of claim 1, further comprising:

anesthetizing the patient, wherein the patient is not anesthetized with total intravenous anesthesia.

12. A non-transitory computer-readable medium for use during a spinal surgical procedure of a patient, comprising instructions stored thereon, that when executed on a processor, perform the steps of:

providing, at a display, graphical information regarding a transcutaneous nerve root stimulation functional mode showing an image of a human body showing electrode placement on the human body with:

a first electrode at the back of the human body at spinal level L1-2 superior to a target surgical site; and a second electrode at a front of the human body over the human body's anterior abdominal midline;

periodically during the spinal surgical procedure, causing delivery, from a cathode electrode corresponding to the first electrode to an anode electrode corresponding to the second electrode, a first and second transcutaneous, trans-abdominal stimulation signals to lumbar motor neural pathways prior to establishing an operative corridor to a surgical target site of the patient along a lateral, trans-psoas path;

processing response signals received by at least one electrode located inferior to the surgical target site in response to the first transcutaneous, transabdominal stimulation signal, thereby determining a first neuromuscular response data set;

monitoring changes to health of one or more nerves during the spinal surgical procedure by detecting changes to stimulation threshold intensities of the one or more nerves using the first neuromuscular response data set;

recording, by the at least one electrode located inferior to the surgical target site, first and second responses to said first and second stimulation signals of a muscle located inferior to said surgical target site;

receiving said first and second responses in a control unit, said control unit toggleable between an alert testing mode and a threshold testing mode;

automatically evaluating, by the control unit, the recorded first and second responses for at least one of:

a presence and absence of said second response while operating in said alert testing mode; and changes, over time, to stimulation signal intensity of said first and second transcutaneous, trans-abdominal stimulation signals required to elicit said first and second responses while operating in said threshold testing mode; and converting said evaluated first and second responses to a health status of neural structures of the patient for display to a user, wherein said health status, when operating in said alert testing mode, provides a first display view when said presence of said second response is found and a second display view when said absence of said second response is found, and wherein said health status, when operating in said threshold testing mode, provides a third display view when the difference between said stimulation signal intensity of said first and second transcutaneous, trans-abdominal stimulation signals are within a pre-determined amount, and a fourth display view when the difference between said stimulation signal intensity of said first and second transcutaneous, trans-abdominal stimulation signals are not within said pre-determined amount.

13. The medium of claim 12, wherein each of the first stimulation signal and the second stimulation signal are a monophasic single pulse signal.

14. The medium of claim 12, wherein the second display view uses a color indicator to alert a user of said absence of said second response.

15. The medium of claim 12, further comprising delivering a plurality of transcutaneous, trans-abdominal stimulation signals at timed intervals.

16. The medium of claim 12, further comprising establishing a baseline response for the muscle.

17. A method of neurophysiologic assessment during a spinal surgical procedure, said method comprising the steps of:

establishing an operative corridor to a surgical target site inferior to spinal level L1-2 along a lateral, trans-psoas path of a patient;

before establishing the operative corridor, delivering a first transcutaneous, transabdominal stimulation signal by a neurophysiologic monitoring system, via a single cathode electrode adhered to the midline of the back of the patient at spinal level L1-2 and a single anode electrode adhered to the patient's anterior abdominal midline, wherein said first transcutaneous, trans-abdominal stimulation signal is of sufficient intensity to evoke a response in a muscle located inferior to said surgical target site; and recording a first neuromuscular response data set of said muscle located inferior to said surgical target site based on the delivery of said first transcutaneous, trans-abdominal stimulation signal, wherein said first neuromuscular response data set includes a stimulation intensity of the delivered first transcutaneous, trans-abdominal stimulation signal and a stimulation intensity of the signal received at said muscle in response to said first transcutaneous, transabdominal stimulation signal, wherein the stimulation intensity of the first delivered signal and the first received signal are recorded in said neurophysiologic monitoring system via one or more electrodes inferior to the surgical site;

delivering, periodically during the spinal surgical procedure, a second transcutaneous, trans-abdominal stimulation signal by the neurophysiologic monitoring system, via the cathode electrode and the anode electrode, to the lumbar motor neural pathways superior and inferior to the surgical target site of said spinal surgical procedure during establishment of the operative corridor to the surgical target site;

recording a second neuromuscular response data set of said muscle located inferior to said surgical target site based on the delivery of said second transcutaneous, trans-abdominal stimulation signal, wherein said second neuromuscular response data set includes a stimulation intensity of the delivered second transcutaneous, trans-abdominal stimulation signal and a stimulation intensity of the signal received at said muscle in response to said second transcutaneous, trans-abdominal stimulation signal, and wherein the stimulation intensity of the second delivered signal and the second received signal are recorded in said neurophysiologic monitoring system via the one or more electrodes;

wherein the neurophysiologic monitoring system has a selectable alert testing mode and a selectable threshold testing mode, wherein a control unit in alert testing mode evaluates the second neuromuscular response data for the presence of a response to said second transcutaneous, trans-abdominal stimulation signal, and wherein the control unit in the threshold testing mode detects changes in stimulation intensity between the first and second neuromuscular response data sets;

monitoring changes to health or status of one or more nerves during the spinal surgical procedure by detecting changes in stimulation intensity of the one or more nerves using the first and second neuromuscular response data sets; and automatically determining, by the neurophysiologic monitoring system, the health or status of the one or more nerves during the spinal surgical procedure based on at least one of the alert testing mode and threshold testing mode, wherein an alert is provided in the alert testing mode if no response is detected to said second transcutaneous, trans-abdominal stimulation signal, and wherein an alert is provided in the threshold testing mode if the difference between said stimulation intensity of said first and second responses are not within a pre-determined amount.

18. The method of claim 17, wherein each of the first and second transcutaneous, trans-abdominal stimulation signals are a monophasic single pulse signal.

19. The method of claim 17, further comprising providing an alert when a predetermined period of time has elapsed since delivering the second transcutaneous, trans-abdominal stimulation signal.

20. The method of claim 17, further comprising:
  anesthetizing the patient, wherein the patient is not anesthetized with total intravenous anesthesia.

* * * * *